US010799572B2

(12) United States Patent
Weiner et al.

(10) Patent No.: US 10,799,572 B2
(45) Date of Patent: Oct. 13, 2020

(54) CONSENSUS ANTIGEN CONSTRUCTS AND VACCINES MADE THEREFROM, AND METHODS OF USING THE SAME TO TREAT MALARIA

(75) Inventors: David B. Weiner, Merion, PA (US); Bernadette Ferraro, Philadelphia, PA (US); Jian Yan, Havertown, PA (US); Niranjan Y. Sardesai, Blue Bell, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 764 days.

(21) Appl. No.: 13/876,148

(22) PCT Filed: Sep. 27, 2011

(86) PCT No.: PCT/US2011/053541

§ 371 (c)(1),
(2), (4) Date: Jun. 27, 2013

(87) PCT Pub. No.: WO2012/047679

PCT Pub. Date: Apr. 12, 2012

(65) Prior Publication Data

US 2013/0273112 A1 Oct. 17, 2013

Related U.S. Application Data

(60) Provisional application No. 61/386,973, filed on Sep. 27, 2010.

(51) Int. Cl.

| | |
|---|---|
| ***A61K 39/015*** | (2006.01) |
| ***C07K 14/445*** | (2006.01) |
| ***A61K 38/19*** | (2006.01) |
| ***A61K 38/20*** | (2006.01) |
| ***A61K 39/00*** | (2006.01) |

(52) U.S. Cl.

CPC .......... *A61K 39/015* (2013.01); *A61K 38/195* (2013.01); *A61K 38/20* (2013.01); *A61K 38/208* (2013.01); *A61K 38/2086* (2013.01); *C07K 14/445* (2013.01); *A61K 2039/53* (2013.01); *A61K 2039/54* (2013.01); *A61K 2039/55527* (2013.01); *A61K 2039/70* (2013.01); *Y02A 50/412* (2018.01)

(58) Field of Classification Search

None

See application file for complete search history.

(56) References Cited

U.S. PATENT DOCUMENTS

| | | | |
|---|---|---|---|
| 4,554,101 | A | 11/1985 | Hopp |
| 5,273,525 | A | 12/1993 | Hofmann |
| 6,110,161 | A | 8/2000 | Mathiesen et al. |
| 6,261,281 | B1 | 7/2001 | Mathiesen et al. |
| 6,697,669 | B2 | 2/2004 | Dev et al. |
| 6,939,862 | B2 | 9/2005 | Bureau et al. |
| 6,958,060 | B2 | 10/2005 | Mathiesen et al. |
| 7,238,522 | B2 | 7/2007 | Hebel et al. |
| 7,245,963 | B2 | 7/2007 | Draghia-Akli et al. |
| 7,328,064 | B2 | 2/2008 | Mathiesen et al. |
| 2005/0052630 | A1 | 3/2005 | Smith et al. |
| 2005/0265974 | A1 | 12/2005 | Pau et al. |
| 2009/0148477 | A1 | 6/2009 | Bruder et al. |
| 2011/0033502 | A1 | 2/2011 | Kappe et al. |
| 2011/0229514 | A1 | 9/2011 | Doolan et al. |

FOREIGN PATENT DOCUMENTS

| | | |
|---|---|---|
| EP | 1661999 A1 | 5/2006 |
| WO | 93/024640 | 12/1993 |
| WO | 94/016737 | 8/1994 |
| WO | 2007027860 | 3/2007 |
| WO | 2009021931 | 2/2009 |
| WO | 2009/124309 | 10/2009 |
| WO | 10/062859 | 6/2010 |

OTHER PUBLICATIONS

Greenspan et al, (Nature Biotechnology 17:936-937, 1999).*

Harlow et al (Antibodies A Laboratory Manual, Cold Spring Harbor Laboratory Press Inc., 1988).*

Colman et al. (Research in Immunology 145: 33-36, 1994).*

Houghten et al. (New Approaches to Immunization, Vaccines 86, Cold Spring Harbor Laboratory, p. 21-25, 1986).*

Bowie et al (Science, 1990, 257:1306-1310).*

Ko, H.J. et al., "Optimization of Codon Usage Enhances the Immunogenicity of a DNA Vaccine Encoding Mycoacterial Antigen Ag85B", Infection and Immunity, 2005, 73(9):5666-5674.

Yan, J. et al., "Enhanced cellular immune responses elicited by an engineered HIV-1 sybtype B consensus-based envelope DNA vaccine", Molecular Therapy, 2007, 15(2):411-421.

Ferraro, B. et al., "Inducing Humoral and Cellular Responses to Multiple Sporozoite and Liver-Stage Malaria Antigens Using Exogenous Plasmid DNA", Infection and Immunity, 2013, 81(10):3709-3720.

Gardner et al., "Genome sequence of the human malaria parasite *Plasmodium falciparum*," 2002, *Nature*, 419:498-511.

Sedegah, M. et al. "Reduced immunogenicity of DNA vaccine plasmids in mixtures", Gene Therapy, 2004, 11 (5):448-566.

Morrow et al., "Comparative ability of IL-12 and IL-28B to regulate Treg populations and enhance adaptive cellular immunity", Blood, 2009, 113(23)5868-5877.

Ferraro et al. "A Novel Multi-Antigen DNA-Based Malaria Vaccine Candidate Delivered by Electroporation Induces Potent Humoral and Cellular Responses" [Retrieved from the Internet Jan. 13, 2012: http://www.nfid.org/pdf/conferences/vaccine10abstracts.pdf>]; p. 118, col. 1 to col. 2.

(Continued)

*Primary Examiner* — Robert A Zeman

(74) *Attorney, Agent, or Firm* — Riverside Law LLP

(57) ABSTRACT

Provided herein is consensus amino acid sequences of *P. falciparum* (P.f.) proteins and their encoding sequences, as well as expression constructs expressing the sequences. Also provided herein are methods for generating an immune response against *P. falciparum* using the expression constructs provided herein.

19 Claims, 36 Drawing Sheets

Specification includes a Sequence Listing.

(56) References Cited

OTHER PUBLICATIONS

Crompton et al. "A prospective analysis of the Ab response to Plasmodium falciparum before and after a malaria season by protein microarray" PNAS USA , Apr. 13, 2010, 107(15):6958-6963; p. 6961, Fig 3.
Cummings et al "Recombinant Liver Stage Antigen-1 (LSA-1) formulated with AS01 and AS02 is safe, elicits high titer antibody and induces IFN-gamma/IL-2 CD4+ T cells but does not protect against experimental Plasmodium falciparum infection" Vaccine, Jul. 12, 2010, (31):5135-5144.
Aly et al. "Malaria Parasite Development in the Mosquito and Infection of the Mammalian Host" Annual Review of Microbiology, 2009, 63:195-221; p. 198, Table 1; p. 199, 203, 208, Fig. 1,2.
Tinjacá Claudia, et al., Informe de Vigilancia Tecnológica: Desarrollo de Vacunas contra la malaria (Technology Watch Inform: vaccine development against Malaria); Bogotá, Colombia, Apr. 2008; 50,50, 52, and 60-61.
English Translation of Official Action from Mexican Patent Office relating to Mexican Patent Application No. MX/a/2013/003470, dated May 8, 2016.
Barry, et al., 2009, Contrasting Population Structures of the Genes Encoding Ten Leading Vaccine-Candidate Antigens of the Human Malaria Parasite, Plasmodium falciparum. PLoS ONE 4(12): e8497.
Thrombospondin-related protein, partial [Plasmodium falciparum]. GenBank :BAA31186.1. 1998.
Thrombospondin related anonymous protein, partial [Plasmodium falciparum] GenBank :AAA29774.1. 2002.
Piper et al., 1999, "Immunocapture Diagnostic Assays for Malaria Using Plasmodium Lactate Dehydrogenase (pLDH)", Am. J. Trop. Med. Hyg., 60(1), pp. 109-118.
Ko et al., "Optimization of Codon Usage Enhances the Immunogenicity of a DNA Vaccine Encoding Mycobacterial Antigen Ag85B", Infection and Immunity, vol. 73, No. 9, pp. 5666-5674 (Sep. 2005).
Girard et al., "A review of human vaccine research and development: Malaria", Vaccine, vol. 25; pp. 1567-1580 (2007).
Kumar et al., "A multilateral effort to develop DNA vaccines against falciparum malaria", Trends in Parasitology, vol. 18, No. 3; pp. 129-135 (2002).
Limbach et al.,"Viral vectors in malaria vaccine development", Parasite Immunology, vol. 31; pp. 501-519 (2009).

* cited by examiner

| Percent Homology of PfConCS to Genbank CS sequences | | | | | |
|---|---|---|---|---|---|
| Accession No. | % Homology | Accession No. | % Homology | Accession No. | % Homology |
| AB116602 | 98.8 | AF540454 | 97.5 | AF540479 | 98.8 |
| AB116603 | 99.3 | AF540458 | 97.2 | AF540480 | 97.6 |
| AB116604 | 99.3 | AF540459 | 97.5 | AF540481 | 99.2 |
| AB116605 | 99.8 | AF540460 | 97.2 | AF540482 | 98.0 |
| AB116606 | 99.8 | AF540461 | 97.4 | AF540483 | 98.1 |
| AB116607 | 99.8 | AF540462 | 97.5 | AF540484 | 98.2 |
| AB121010 | 98.8 | AF540463 | 97.2 | AF540485 | 97.0 |
| AB121015 | 98.8 | AF540464 | 97.7 | AF540486 | 98.1 |
| AB121016 | 99.3 | AF540465 | 98.2 | AF540487 | 98.3 |
| AB121017 | 99.3 | AF540466 | 98.1 | AF540488 | 98.5 |
| AB121018 | 98.3 | AF540467 | 97.6 | AY870439 | 99.5 |
| AB121019 | 98.3 | AF540468 | 97.6 | M15505 | 98.3 |
| AB121021 | 97.9 | AF540469 | 98.2 | M19752 | 99.3 |
| AB121022 | 99.3 | AF540470 | 98.2 | M83149 | 99.0 |
| AB121024 | 98.2 | AF540471 | 98.2 | M83150 | 98.1 |
| AF540442 | 98.5 | AF540472 | 99.0 | M83152 | 99.0 |
| AF540444 | 97.9 | AF540473 | 97.4 | M83155 | 99.0 |
| AF540445 | 98.2 | AF540474 | 98.2 | M83156 | 98.1 |
| AF540446 | 98.2 | AF540475 | 98.0 | M83158 | 99.0 |
| AF540449 | 97.7 | AF540476 | 98.4 | M83161 | 97.6 |
| AF540452 | 97.6 | AF540477 | 98.7 | M83163 | 98.1 |
| AF540453 | 97.6 | AF540478 | 98.8 | M83173 | 98.1 |

Figure 1

| SeqA | Name | Len(aa) | SeqB | Name | Len(aa) | Score |
|---|---|---|---|---|---|---|
| 1 | SEQ ID NO: 14 | 591 | 2 | LSA1 | 1909 | 95 |
| 1 | SEQ ID NO: 14 | 591 | 3 | LSA_NRC | 456 | 96 |

Figure 2

| Percent Homology of PfConTRAP/SSP2 to Genbank TRAP/SSP2 sequences | | | |
|---|---|---|---|
| Accession No. | % Homology | Accession No. | % Homology |
| AAG12328 | 98.7 | AF544209 | 98.7 |
| AB006332 | 97.9 | AF544211 | 98.6 |
| AB006351 | 98.7 | AF544212 | 99.1 |
| AB006352 | 98.2 | AF544213 | 98.7 |
| AB006353 | 98.7 | M96805 | 98.6 |
| AB006354 | 98.2 | M96806 | 97.8 |
| AB006355 | 98.4 | M96807 | 97.3 |
| AB006356 | 98.4 | M96808 | 97.3 |
| AB006357 | 98.7 | M96810 | 97.5 |
| AB006358 | 98 | M96813 | 98.7 |
| AB006359 | 93.7 | M96814 | 98.2 |
| AF249739 | 98.7 | M96815 | 97.7 |
| AF544201 | 97.7 | X13022 | 96.8 |

Figure 3

| SeqA | Name | Len(aa) | SeqB | Name | Len(aa) | Score |
|---|---|---|---|---|---|---|
| 1 | SEQ ID NO: 32 | 208 | 2 | CelTOS_3D7_XP001350569.1 | 182 | 99 |

Figure 4

Figure 7
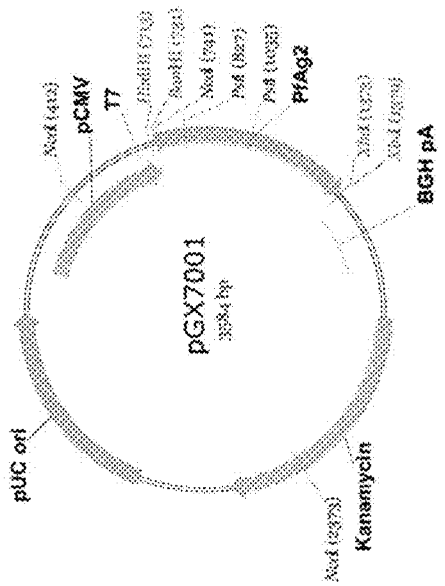
Figure 8
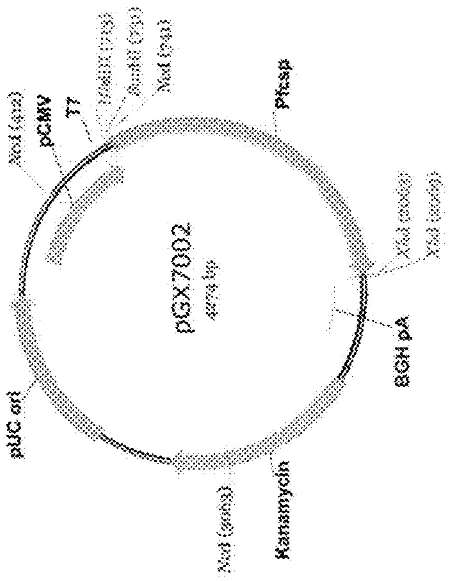
Figures 7 and 8

Figure 9
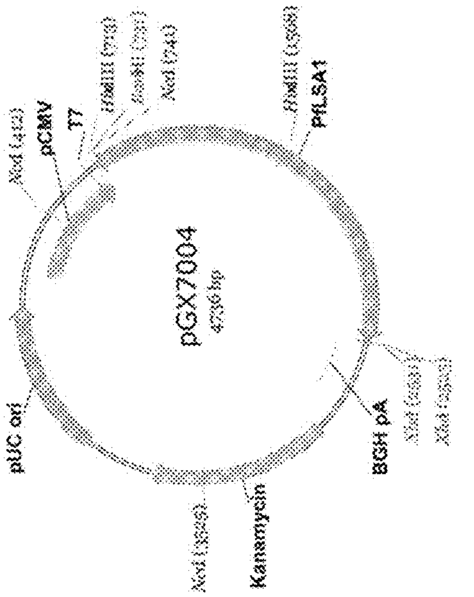
Figure 10
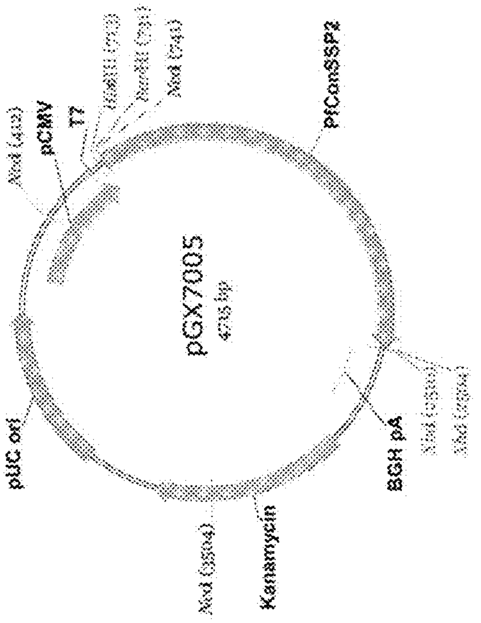
Figures 9 and 10

Figure 22

| | IM | IM+IL-28 | ID |
|---|---|---|---|
| CSP | 241,356 (1-1,581,111) | 54,816 (158-158,111) | 1,044,794 (50-5,000,000) |
| LSA1 | 807,978 (158,111-5,000,000) | 1,173,244 (50,000-5,000,000) | 1,619,826 (15,811-5,000,000) |
| TRAP | 364,169 (15,811-1,581,111) | 29,487 (15,811-50,000) | 114,867 (50,000-158,111) |
| CelTOS | 792,325 (1581-5,000,000) | 176,407 (50,000-500,000) | 511,089 (158,111-500,000) |

CONSENSUS ANTIGEN CONSTRUCTS AND VACCINES MADE THEREFROM, AND METHODS OF USING THE SAME TO TREAT MALARIA

CROSS-REFERENCE TO RELATED APPLICATIONS

This application claims priority to and is a United States National Stage filing under 35 USC § 371 of International PCT Application Serial No. PCT/US2011/053541, filed Sep. 27, 2011, which claims priority to U.S. Provisional Application No. 61/386,973, filed Sep. 27, 2010, each of which is incorporated herein by reference in its entirety.

FIELD OF THE INVENTION

The present invention relates to consensus antigenic malaria proteins and nucleic acid molecules which encode the same; improved malaria vaccines including such proteins and/or nucleic acid molecules; and methods for using the vaccines for inducing immune responses against malaria antigens and methods of preventing malaria infection and/or treating individuals infected with malaria.

BACKGROUND OF THE INVENTION

This application claims priority to U.S. Provisional Ser. No. 61/386,972 filed Sep. 27, 2010, which is incorporated herein by reference.

Malaria is a mosquito-borne infectious disease caused by a eukaryotic protist of the genus *Plasmodium*. It is widespread in tropical and subtropical regions, including parts of the Americas (22 countries), Asia, and Africa. Each year, there are more than 250 million cases of malaria, killing between one and three million people, the majority of whom are young children in sub-Saharan Africa. Despite efforts to reduce transmission and increase treatment, there has been little change in which areas are at risk of this disease since 1992. Indeed, if the prevalence of malaria stays on its present upwards course, the death rate could double in the next twenty years. Precise statistics are unknown because many cases occur in rural areas where people do not have access to hospitals or the means to afford health care. As a consequence, the majority of cases are undocumented.

Five species of the *plasmodium* parasite can infect humans: the most serious forms of the disease are caused by *Plasmodium falciparum* (also referred to herein as *P. falciparum*, P.f. and PF). *P. falciparum* is a protozoan parasite, one of the species of *Plasmodium* that cause malaria in humans. It is transmitted by the female *Anopheles* mosquito. *P. falciparum* is the most dangerous of these infections as *P. falciparum* (or malignant) malaria has the highest rates of complications and mortality. As of 2006 it accounted for 91% of all 247 million human malarial infections (98% in Africa) and 90% of the deaths.

A wide variety of antimalarial drugs are available to treat malaria. In the last 5 years, treatment of *P. falciparum* infections in endemic countries has been transformed by the use of combinations of drugs containing an artemisinin derivative. Severe malaria is treated with intravenous or intramuscular quinine or, increasingly, the artemisinin derivative artesunate. Several drugs are also available to prevent malaria in travellers to malaria-endemic countries (prophylaxis). Resistance has developed to several antimalarial drugs, most notably chloroquine.

Vaccines for malaria are under development, with no completely effective vaccine yet available. The first promising studies demonstrating the potential for a malaria vaccine were performed in 1967 by immunizing mice with live, radiation-attenuated sporozoites, providing protection to about 60% of the mice upon subsequent injection with normal, viable sporozoites. Since the 1970s, there has been a considerable effort to develop similar vaccination strategies within humans. However, the current most advanced malaria vaccine candidate confers only partial protection against clinical disease.

SUMMARY OF THE INVENTION

Nucleic acid molecules such as plasmids are provided which encode one or more of the *P. falciparum* immunogens CS; LSA1; TRAP; CelTOS; and Ama1. The immunogens may be full length or immunogenic fragments of full length proteins. The immunogens comprise consensus sequences and/or modifications for improved expression. Coding sequences are provided which provide high levels of expression when delivered in vivo.

Compositions comprising one or more of these nucleic acid molecules which collectively encode one, two, three, four or all five immunogens are provided. Such compositions may be useful as vaccines against malaria. Methods of immunizing mammals against malaria are provided which comprise administering one of more compositions as disclosed herein.

BRIEF DESCRIPTION OF THE DRAWINGS

FIG. 1 relates to the consensus antigen sequence for *P. falciparum* circumsporozoite protein (PfConCS) (SEQ ID NO:2). FIG. 1 includes a table of homology between PfConCS (SEQ ID NO:2) and selected CS sequences from Genbank.

FIG. 2 relates to the consensus antigen sequence for *P. falciparum* liver stage antigen 1 protein (PfConLSA1) (SEQ ID NO:4). FIG. 2 includes a table of homology between PfConLSA1 and selected LSA1 sequences. The PfConLAS1 sequence shown is SEQ ID NO:28 which is SEQ ID NO:4 plus the IgE signal peptide at the N terminus in place of the LAS1 N terminal Methionione and the HA Tag at the LAS1 C terminal the IgE signal peptide and HA Tag.

FIG. 3 relates to the consensus antigen sequence for *P. falciparum* thrombospondin-related-anonymous protein (PfConTRAP) (SEQ ID NO:6). FIG. 3 includes a table of homology between PfConTRAP (SEQ ID NO:6) and selected TRAP sequences from Genbank.

FIG. 4 relates to the consensus antigen sequence for *P. falciparum* cell-traversal protein for ookinetes and sporozoites (PfConAg2 or PfConCelTOS) (SEQ ID NO:8). FIG. 4 homology between PfConCelTOS (SEQ ID NO:8) and a CelTOS sequence from Genbank. The PfConCelTOS sequence shown is SEQ ID NO:32 which is SEQ ID NO:8 plus the IgE signal peptide at the N terminus in place of the CelTOS N terminal Methionione and the HA Tag at the CelTOS C terminal the IgE signal peptide and HA Tag.

FIG. 6A displays bar graphs that show cellular immunogenicity of the individual antigens (left panel) based on INF-γ ELISpot analysis, and the class of cellular response (CD4 or CD8) for CS and LSA1 (right panel). FIG. 6B includes graphs (CD8 top set; and CD4 bottom set) that show comparison of immunogenicity of reported platforms: PfConLSA1 (right graph) induces stronger cellular responses to dominant CD4+ and CD8+ T cell epitopes than Ad35 or Ad35/protein heterologous prime boost approaches (left 3 graphs). FIG. 6C includes graphs that show comparison of immunogenicity relative to other platforms: PfconCS (right graph) induced antigen specific IFN-γ slightly lower than Ad5 (left pair of graphs), but stronger than Ad35 and RTS,S. FIG. 6D display graphs that show images detailing the flow cytometry gating strategy. FIG. 6E include graphs that show the CD4+ T cell responses against the multiple antigen vaccine, showing that CS-specific responses are the predominant the CD4+ T cell response. FIG. 6F includes graphs that show the CD8+ T cell responses against the multiple antigen vaccine, showing that CS-specific and LSA-specific responses comprise most of the CD8+ T cell response. FIG. 6G displays graphs that show the CD8+ T cell responses of a single antigen vaccine and compares to a multiple antigen vaccine, showing that there is no significant change when delivering multiple antigens. FIG. 6H includes graphs that show humoral responses, which provide that both the single and multiple antigen vaccines induced strong antibody responses (average endpoint titers >100, 000). FIG. 6I includes graphs that show that the LSA1 antibodies are associated with epitopes outside of the repeat region.

FIG. 7 is a plasmid map of expression construct pGX7001 (SEQ ID NO:37), which includes coding sequence of PfConAG2 (CelTOS) including the IgE signal peptide and HA Tag (SEQ ID NO:31 which encodes SEQ ID NO:32).

FIG. 8 displays a plasmid map of expression construct pGX7002 (SEQ ID NO:38), which includes encoding sequence of PfConCS including the IgE signal peptide and HA Tag (SEQ ID NO:25, which encodes SEQ ID NO:26).

FIG. 9 displays a plasmid map of expression construct pGX7004 (SEQ ID NO:39), which includes encoding sequence of PfConLSA1 including the IgE signal peptide and HA Tag (SEQ ID NO:27, which encodes SEQ ID NO:28).

FIG. 10 displays a plasmid map of expression construct pGX7005 (SEQ ID NO:40), which includes encoding sequence of PfConTRAP including the IgE signal peptide and HA Tag (SEQ ID NO:29, which encodes SEQ ID NO:30).

FIGS. 12-25 include data from immunological analyses of immunized animals and their sera. The P.f. consensus immunogen constructs used included nucleic acid sequences encoding CS, LSA1, TRAP, CelTOS and Ama1 each including coding sequences that encode an IgE signal peptide and HA Tag. The nucleic acid sequences that were used which encoded CS, LSA1, TRAP, CelTOS and Ama1 were SEQ ID NOs:25, 27, 29, 31 and 33, respectively, which encode amino acid sequence SEQ ID NOs:26, 28, 30, 32 and 34 respectively. The portion of these nucleic acid sequences that encode full length CS, LSA1, TRAP, CelTOS and Ama1 without the signal peptide or HA Tag correspond to SEQ ID NOs:1, 3, 5, 7 and 9, respectively, which encode amino acid sequences SEQ ID NOs:2, 4, 6, 8 and 10, respectively.

FIG. 12 shows data comparing humoral responses from vaccines comprising single and multi-antigen constructs.

FIG. 13 shows data of CD4+ T cell responses induced by vaccines comprising multi-antigen constructs against each of the antigens encoded by constructs in the vaccine.

FIG. 14 shows data of CD8+ T cell responses induced by vaccines comprising multi-antigen constructs against each of the antigens encoded by constructs in the vaccine.

FIG. 15 shows data comparing immune responses evaluated by IFNγ ELISpot induced by administration of a vaccine encoding CS versus administration of a vaccine encoding CS in combination with a vaccines encoding TRAP, LSA1 and CelTOS.

FIG. 16 shows data comparing CS-specific in IFNγ responses induced by either delivering half of the total volume of the multi-antigen vaccine cocktail to one mouse hind limb and the other half into the contra-lateral mouse hind limb versus delivery of a CS vaccine into one mouse hind limb and a cocktail containing the LSA1, TRAP and CelTOS vaccines into the contra-lateral hind limb.

FIG. 17 shows data evaluating LSA1-specific IFNγ production by CD8+ hepatic lymphocytes in multi-antigen vaccinated mice.

FIG. 18A shows data from evaluation of AMA1-specific T cell responses induced by a vaccine construct encoding the AMA1 protein.

FIG. 18B shows data from evaluation of AMA1-specific seroconversion induced by a vaccine construct encoding the AMA1 protein.

FIG. 19 shows data comparing immune responses evaluated by IFNγ ELISpot induced by administration of multi antigen vaccine with or without a construct encoding the adjuvant IL-28B measured before and after the first and second immunizations. The left panel shows data as a bar graph of combined responses. The right panel shows data for responses against individual antigens separately.

FIG. 20 shows data comparing antigen-specific CD4+ T cell immune responses following the 2nd immunization (week 8) with either a multi-antigen vaccine with or without a construct encoding the adjuvant IL-28B delivered IM or a multi-antigen vaccine delivered ID. The left panel of FIG. 20 shows antigen specific IFNγ production data, the center panel shows antigen specific IL-2 production data and the right panel shows antigen-specific TNFα production data.

FIG. 21 shows data comparing antigen-specific CD8+ T cell immune responses following the 2nd immunization (week 8) with either a multi-antigen vaccine with or without a construct encoding the adjuvant IL-28B delivered IM or a multi-antigen vaccine delivered ID. The top left panel of FIG. 21 shows antigen specific IFNγ production data, the center panel shows antigen specific IL-2 production data and the right panel shows antigen-specific TNFα production data. The lower left panel of FIG. 21, shows data determining antigen specific granzyme B evaluations in CD8+ IFNγ+ T cells.

FIG. 22 shows data comparing antigen-specific seroconversion for all antigens after second immunization with either a multi-antigen vaccine with or without a construct encoding the adjuvant IL-28B delivered IM or a multi-antigen vaccine delivered ID.

FIG. 23 shows data comparing antigen-specific immune responses evaluated by IFNγ ELISpot induced by administration of multi antigen vaccine without or in combination with various amounts of a construct encoding the adjuvant IL-28B. The left panel shows measured before and after the first and second immunizations. The left panel shows antigen-specific immune responses as a bar graph of combined responses; the right panel shows data for CS-specific immune responses.

FIG. 24 shows data comparing populations of CD4+ CD25+FoxP3+ regulatory T cells following administration of multi antigen vaccine without or in combination with various amounts of a construct encoding the adjuvant IL-28B.

FIG. 25 shows data comparing CS-specific serocoversion populations of CD4+CD25+FoxP3+ regulatory T cells following administration of multi antigen vaccine without or in combination with various amounts of a construct encoding the adjuvant IL-28B.

DETAILED DESCRIPTION OF PREFERRED EMBODIMENTS

Figure 5:
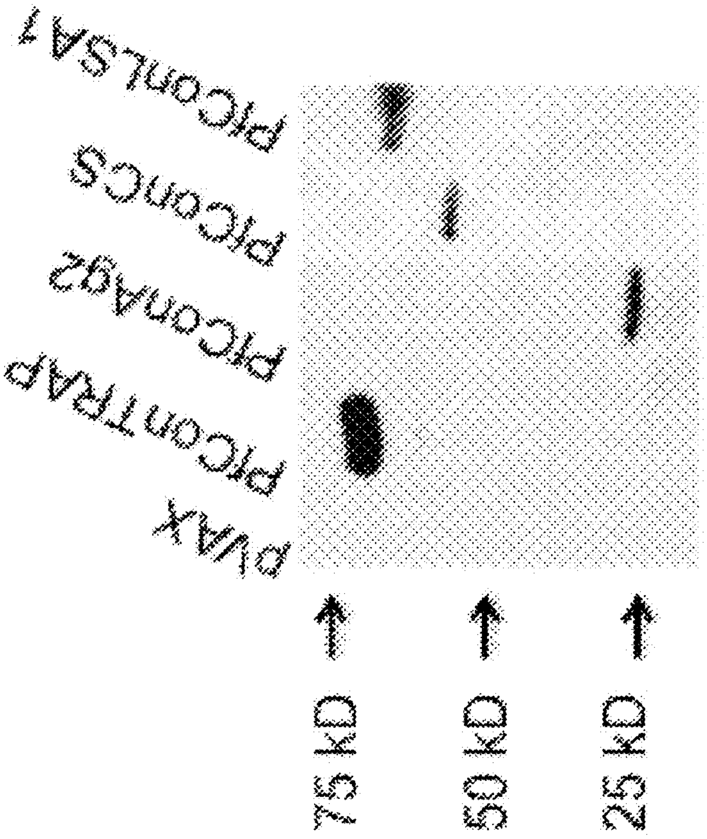
FIG. 5 is an image of a SDS-PAGE gel from a western blot analysis. The synthesized proteins were detected using an anti-HA antibody (the HA tag is contained in the C-terminus of the antigen sequences). pVAX1 was used as a negative control.

In one aspect of the invention, it is desired that the consensus antigen provides for improved transcription and translation, including having one or more of the following: low GC content leader sequence to increase transcription; mRNA stability and codon optimization; eliminating to the extent possible cis-acting sequence motifs (i.e., internal TATA-boxes).

In some aspects of the invention, it is desired to generate a consensus antigen that generates a broad immune response across multiple strains, including having one or more of the following: incorporate all available full-length sequences; computer generate sequences that utilize the most commonly occurring amino acid at each position; and increase cross-reactivity between strains.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein may mean any molecule added to the DNA plasmid vaccines described herein to enhance antigenicity of the malaria (P.f.) antigen encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein may mean a synthetic nucleic acid sequence, or corresponding polypeptide sequence, constructed based on analysis of an alignment of multiple subtypes of a particular malaria antigen, that can be used to induce broad immunity against multiple subtypes or serotypes of a particular malaria antigen. Consensus malaria antigens may include CS, LSA1, TRAP, CelTOS and AMA1 proteins. Nucleotide sequences that encode the consensus amino acid sequences are also provided including those designed for high levels of expression. Also, synthetic antigens such as fusion proteins may include consensus sequences (or consensus antigens).

f. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

h. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

k. Fragment

"Fragment" may mean a polypeptide fragment of a malaria consensus immunogen that is capable of eliciting an immune response in a mammal against malaria by recognizing the particular malaria antigen. A fragment may comprise a fragments of a malaria consensus immunogen linked to a signal peptide such as an immunoglobulin signal peptide for example IgE signal peptide (SEQ ID NO:42) or IgG signal peptide.

A fragment of a PfCon consensus malaria immunogen such as PfConCS consensus malaria immunogen, or a fragment of PfConLAS1 consensus malaria immunogen, or a fragment of PfConTRAP consensus malaria immunogen, or a fragment of PfConCelTOS consensus malaria immunogen, or a fragment of PfConAMA1 consensus malaria immunogen, or a fragment of PfConCS-alt alternative consensus malaria immunogen may 90% or more, 91% or more, 92% or more, 93% or more, 94% or more, 95% or more, 96% or more, 97% or more, 98% or more, 99% or more percent of the length of the full length PfConCS Immunogen sequence (SEQ ID NO:2), the full length PfConLAS1 consensus malaria immunogen (SEQ ID NO:4), or a fragment of the full length PfConTRAP consensus malaria immunogen (SEQ ID NO:6), or a fragment of the full length PfConCelTOS consensus malaria immunogen (SEQ ID NO:8), or a fragment of the full length PfConAMA1 consensus malaria immunogen (SEQ ID NO:10), or a fragment of the full length PfConCS-alt (SEQ ID NO:12), respectively, as set forth herein. When calculating fragment size of P.f. consensus sequences which comprise a signal peptide or other added sequence (for examples proteins comprising P.f. consensus sequences such as SEQ ID NOs:14, 16, 18, 20, 22, 24, 26, 28, 30, 32, 34 and 36), the calculation is full length sequence Pf sequence portion only (SEQ ID NOs; 2, 4, 6, 8, 10 or 12). In some embodiments a fragment of one of the full length PfConCS Immunogen sequence (SEQ ID NO:2), the full length PfConLAS1 consensus malaria immunogen (SEQ ID NO:4), or a fragment of the full length PfConTRAP consensus malaria immunogen (SEQ ID NO:6), or a fragment of the full length PfConCelTOS consensus malaria immunogen (SEQ ID NO:8), or a fragment of the full length PfConAMA1 consensus malaria immunogen (SEQ ID NO:10), or a fragment of the full length PfConCS-alt (SEQ ID NO:12), respectively, comprises all but 1, 2, 3, 4, 5, 6, 7, 8, 9 or 10 amino acid residues of the N terminal sequence or all but 1, 2, 3, 4, 5, 6, 7, 8, 9 or 10 amino acid residues of the C terminal sequence or all but a combination of 1, 2, 3, 4, 5, 6, 7, 8, 9 or 10 amino acid residues of the N terminal sequence and all but 1, 2, 3, 4, 5, 6, 7, 8, 9 or 10 amino acid residues of the C terminal sequence.

Fragments also refer to fragments of homologous variant amino acid sequences which are polypeptides that are 98% or more, or 99% or more homologous to the sequences of one of the full length PfConCS Immunogen sequence (SEQ ID NO:2), the full length PfConLAS1 consensus malaria immunogen (SEQ ID NO:4), or a fragment of the full length PfConTRAP consensus malaria immunogen (SEQ ID NO:6), or a fragment of the full length PfConCelTOS consensus malaria immunogen (SEQ ID NO:8), or a fragment of the full length PfConAMA1 consensus malaria immunogen (SEQ ID NO:10), or a fragment of the full length PfConCS-alt (SEQ ID NO:12), respectively. The fragments of homologous variant amino acid sequences are 90% or more, 91% or more, 92% or more, 93% or more, 94% or more, 95% or more, 96% or more, 97% or more, 98% or more, 99% or more percent of the length of the particular full length homologous variant amino acid sequences (polypeptides that are 98% or more, or 99% or more homologous to the full length PfConCS Immunogen sequence (SEQ ID NO:2), the full length PfConLAS1 consensus malaria immunogen (SEQ ID NO:4), or a fragment of the full length PfConTRAP consensus malaria immunogen (SEQ ID NO:6), or a fragment of the full length PfConCelTOS consensus malaria immunogen (SEQ ID NO:8), or a fragment of the full length PfConAMA1 consensus malaria immunogen (SEQ ID NO:10), or a fragment of the full length PfConCS-alt (SEQ ID NO:12), respectively) When calculating homology of a homologous variant amino acid sequences to a P.f. consensus immunogen sequence (SEQ ID NO:2, 4, 6, 8 or 10), calculations do not include any signal peptide or other added sequence linked to the amino acid sequences of the homologous variant amino acid sequences that correspond to a P.f. consensus immunogen sequence. When calculating the length of a fragment of a homologous variant amino acid sequence, the calculation is based upon the percentage of the full homologous variant amino acid sequences that correspond to a P.f. consensus immunogen sequence. In some embodiments a fragment of the full length homologous variant amino acid sequence comprises all but 1, 2, 3, 4, 5, 6, 7, 8, 9 or 10 amino acid residues of the N terminal sequence or all but 1, 2, 3, 4, 5, 6, 7, 8, 9 or 10 amino acid residues of the C terminal sequence or all but a combination of 1, 2, 3, 4, 5, 6, 7, 8, 9 or 10 amino acid residues of the N terminal sequence and all but 1, 2, 3, 4, 5, 6, 7, 8, 9 or 10 amino acid residues of the C terminal sequence of the full length homologous variant amino acid sequences.

"Fragment" may also be a nucleic acid sequence that encodes a fragment of a full length PF consensus Immunogen as described above, or a nucleic acid sequence that encodes a fragment of a homologous variant amino acid sequences as described above. A fragment may be a nucleic acid sequence that is a fragment of SEQ ID NOs: 1, 3, 5, 7, 9 or 11 and encodes a fragment of a full length PF consensus Immunogen as described above. A fragment may be a nucleic acid sequence that is a fragment of a homologous variant nucleic acid sequence. A homologous variant nucleic acid sequence is a nucleotide sequence that is 98% or more, or 99% or more homologous to SEQ ID NOs: 1, 3, 5, 7, 9 or 11 and encodes a protein that is 98% or more, or 99% or more homologous to SEQ ID NOs: 2, 4, 6, 8, 10 or 12. A fragment of a homologous variant nucleic acid sequence encodes a fragment of a homologous variant amino acid sequence. The fragment of SEQ ID NOs: 1, 3, 5, 7, 9, 11 or a homologous variant nucleic acid sequence may comprise coding sequences that encode a signal peptide, preferably a immunoglobulin signal peptide, preferable an IgE or IgG signal peptide. Calculations of percent homology between homologous variant nucleic acid sequence and consensus PF immunogen coding sequences (SEQ ID NOs: 1, 3, 5, 7, 9 or 11) do not include coding sequences for signal peptides or any other non-consensus full length PF immunogen coding sequences that may be linked to homologous variant nucleic acid sequence. Fragment size as a percentage of full length homologous variant nucleic acid sequence do not include coding sequences for signal peptides or any other non-consensus full length PF immunogen coding sequences that may be linked to homologous variant nucleic acid sequence or fragment thereof.

l. Homologous Variants

"Homologous variant amino acid sequences" may mean polypeptides that are 98% or more, or 99% or more homologous to the sequences of one of the full length PfConCS Immunogen sequence (SEQ ID NO:2), the full length PfConLAS1 consensus malaria immunogen (SEQ ID NO:4), or a fragment of the full length PfConTRAP consensus malaria immunogen (SEQ ID NO:6), or a fragment of the full length PfConCelTOS consensus malaria immunogen (SEQ ID NO:8), or a fragment of the full length PfConAMA1 consensus malaria immunogen (SEQ ID NO:10), or a fragment of the full length PfConCS-alt (SEQ ID NO:12), respectively, and are capable of eliciting an immune response in a mammal against malaria by recognizing the particular malaria antigen. A homologous variant amino acid sequence may comprise be linked to a signal peptide such as an immunoglobulin signal peptide for example IgE signal peptide or IgG signal peptide. When calculating homology of a homologous variant amino acid sequences to a P.f. consensus immunogen sequence (SEQ ID NO:2, 4, 6, 8 or 10), calculations do not include any signal peptide or other added sequence linked to the amino acid sequences of the homologous variant amino acid sequences that correspond to a P.f. consensus immunogen sequence.

"Homologous variant nucleic acid sequence" refers to a nucleotide sequence that is 98% or more, or 99% or more homologous to SEQ ID NOs: 1, 3, 5, 7, 9 or 11 and encodes a protein that is 98% or more, or 99% or more homologous to SEQ ID NOs: 2, 4, 6, 8, 10 or 12 capable of eliciting an immune response in a mammal against malaria by recognizing the particular malaria antigen. A homologous variant nucleic acid sequence may comprise coding sequences that encode a signal peptide, preferably an immunoglobulin signal peptide, preferable an IgE or IgG signal peptide. Calculations of percent homology between homologous variant nucleic acid sequence and consensus PF immunogen coding sequences (SEQ ID NOs: 1, 3, 5, 7, 9 or 11) do not include coding sequences for signal peptides or any other non-consensus full length PF immunogen coding sequences that may be linked to homologous variant nucleic acid sequence. In some embodiments, homologous variant nucleic acid sequence encodes a protein comprising SEQ ID NOs: 2, 4, 6, 8, 10 or 12.

l. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

m. Impedance

"Impedance" as used herein may be used when discussing the feedback mechanism and can be converted to a current value according to Ohm's law, thus enabling comparisons with the preset current.

n. Immune Response

"Immune response" as used herein may mean the activation of a host's immune system, e.g., that of a mammal, in response to the introduction of malaria consensus antigen via the provided DNA plasmid vaccines. The immune response can be in the form of a cellular or humoral response, or both.

o. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

p. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

q. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

r. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

s. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

t. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

u. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

v. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. P.f. Consensus Immunogens

Provided herein are consensus PF proteins, also referred to herein as "consensus PF immunogens", which are consensus antigens capable of eliciting an immune response against PF. A total of six consensus sequences were prepared. Consensus PF proteins may comprising SEQ ID NOs: 2, 4, 6, 8, 10 or 12, a fragment thereof as described herein, a homologous variant amino acid sequence thereof as described herein, of a fragment of a homologous variant amino acid sequence as described herein. Consensus PF proteins may comprise a signal peptide such as an immunoglobulin signal peptide such as an IgE or IgG signal peptide. Embodiments in which a consensus PF proteins SEQ ID NOs: 2, 4, 6, 8, 10 or 12 further comprises an IgE signal peptide include SEQ ID NOs:14, 16, 18, 20, 22, 24, 26, 28, 30, 32, 34 and 36. Preferred embodiments include a signal peptide such as an IgE signal peptide. In each protein, the N terminal methionine of the PF consensus sequences is replaced with the signal peptide. In some embodiments, consensus PF proteins comprise other amino acid sequences such as an HA Tag. Embodiments in which a consensus PF proteins SEQ ID NOs: 2, 4, 6, 8, 10 or 12 further comprises an IgE signal peptide and an HA Tag include SEQ ID NOs: 26, 28, 30, 32, 34 and 36.

The Consensus CS consensus sequence was designed from a compilation of all full-length Circumsporozoite Protein sequences in the GenBank database (66 sequences total). The protein sequence for full length PfConCS leader sequence is SEQ ID NO:2. The percent homology of SEQ ID NO:2 to each of the contributing sequences is reported in FIG. 1. The median homology of SEQ ID NO:2 with all 66 Genbank sequences is 98.2% (97.0-99.8). “Consensus CS immunogens” refer to proteins comprise SEQ ID NO:2, fragments thereof as described herein, homologous amino acid sequences to SEQ ID NO:2 as described herein, and fragments thereof as described herein. Consensus CS immunogens may comprise a signal peptide such as an immunoglobulin signal peptide such as an IgE or IgG signal peptide and in some embodiments, may comprise an HA Tag. Consensus CS immunogens that comprise an IgE signal peptide include SEQ ID NOs: 14 and 26. SEQ ID NO:26 is a consensus CS immunogens that comprise an IgE signal peptide and an HA Tag.

LSA1 is a highly conserved antigen. The consensus sequence PfConLSA1 was designed based on the full-length Pf LSA1 sequence in the GenBank database. The protein sequence for full length PfConLSA is SEQ ID NO:4. FIG. 2 shows homology of SEQ ID NO:4 to full-length Pf LSA1 sequence in the GenBank database and LSA1-NRC, a recombinant protein vaccine candidate. SEQ ID NO:4 is 95% homologous to the full-length LSA1 sequence and 96% homologous to LSA-NRC. The PfConLAS1 sequence shown includes FIG. 2 in SEQ ID NO:28. The full-length LSA1 sequence contains multiple repeat regions in the center of the protein. PfConLSA1 contains only 8 of these repeat regions. The sequence alignment was minimized to include only a portion of the repeat region that is not contained in PfConLSA1 or LSA1-NRC. “Consensus LAS1 immunogens” refer to proteins comprise SEQ ID NO:4, fragments thereof as described herein, homologous amino acid sequences to SEQ ID NO:4 as described herein, and fragments thereof as described herein. Consensus LAS1 immunogens may comprise a signal peptide such as an immunoglobulin signal peptide such as an IgE or IgG signal peptide and in some embodiments, may comprise an HA Tag. Consensus LAS1 immunogens that comprise an IgE signal peptide include SEQ ID NOs: 16 and 28. SEQ ID NO:28 is a consensus CS immunogens that comprise an IgE signal peptide and an HA Tag.

The consensus sequence of TRAP, which is also referred to as SSP2, was designed from a compilation of all full-length *Plasmodium falciparum* TRAP/SSP2 sequences in the GenBank database (28 sequences total). Protein sequence for full length PfConTRAP/SSP2 is SEQ ID NO:6. The percent homology of SEQ ID NO:6 to each of the contributing sequences is reported in the table in FIG. 3. The median homology of SEQ ID NO:6 with all 28 Genbank sequences is 98.3% (93.0-99.1). “Consensus TRAP immunogens” refer to proteins comprise SEQ ID NO:6, fragments thereof as described herein, homologous amino acid sequences to SEQ ID NO:6 as described herein, and fragments thereof as described herein. Consensus TRAP immunogens may comprise a signal peptide such as an immunoglobulin signal peptide such as an IgE or IgG signal peptide and in some embodiments, may comprise an HA Tag. Consensus TRAP immunogens that comprise an IgE signal peptide include SEQ ID NOs: 18 and 30. SEQ ID NO:30 is a consensus TRAP immunogens that comprise an IgE signal peptide and an HA Tag.

CelTOS, which is also referred to as Ag2, is a highly conserved *Plasmodium* antigen. The consensus sequence PfConAg2 (PfConCelTOS), SEQ ID NO:8, was designed based on the full-length CelTOS sequence in the GenBank database identified in FIG. 4 with the addition of the novel leader sequence. The PfConCelTOS sequence shown includes FIG. 4 in SEQ ID NO:32. Consensus CelTOS immunogens refer to proteins comprise SEQ ID NO:8, fragments thereof as described herein, homologous amino acid sequences to SEQ ID NO:8 as described herein, and fragments thereof as described herein and comprise a signal peptide such as an immunoglobulin signal peptide such as an IgE or IgG signal peptide and in some embodiments, may comprise an HA Tag. Consensus CelTOS immunogens that comprise an IgE signal peptide include SEQ ID NOs: 20 and 32. SEQ ID NO:32 is a consensus CelTOS immunogens that comprise an IgE signal peptide and an HA Tag.

Ama1 is a highly conserved *Plasmodium* antigen. The consensus sequence PfConAma1, SEQ ID NO:10, was designed based on the full-length Ama1 sequence. Consensus Ama1 immunogens refer to proteins comprise SEQ ID NO:10, fragments thereof as described herein, homologous amino acid sequences to SEQ ID NO:10 as described herein, and fragments thereof as described herein and comprise a signal peptide such as an immunoglobulin signal peptide such as an IgE or IgG signal peptide and in some embodiments, may comprise an HA Tag. Consensus Ama1 immunogens that comprise an IgE signal peptide include SEQ ID NOs: 22 and 34. SEQ ID NO:34 is a consensus Ama1 immunogens that comprise an IgE signal peptide and an HA Tag.

An alternative Consensus CS consensus sequence, consensus CS-alt was designed. Protein sequence for PfConCS-alt is SEQ ID NO:12. ““Consensus CS-alt immunogens” refer to proteins comprise SEQ ID NO:12, fragments thereof as described herein, homologous amino acid sequences to SEQ ID NO:12 as described herein, and fragments thereof as described herein and may comprise a signal peptide such as an immunoglobulin signal peptide such as an IgE or IgG signal peptide and in some embodiments, may comprise an HA Tag. Consensus CS-alt immunogens that comprise an IgE signal peptide include SEQ ID NOs: 24 and 36. SEQ ID NO:36 is a consensus CS-alt immunogens that comprise an IgE signal peptide and an HA Tag.

In some embodiments, fusion proteins are provided which comprise a combination of two or more of the PF proteins set forth herein. For example, fusion proteins may comprise two or more of Consensus CS immunogen or ConCS-alt immunogen, ConLSA1 immunogen, ConTRAP immunogen, ConCelTOS immunogen and, ConAma1 immunogen linked directly adjacent to each other or linked with a spacer or one more amino acids in between. In some embodiments the fusion protein comprises two PF immunogens; in some embodiments the fusion protein comprises three PF immunogens, in some embodiments the fusion protein comprises four PF immunogens, and in some embodiments the fusion protein comprises five PF immunogens. Fusion proteins with two Consensus PF immunogens may comprise: CS or CS-alt and LSA1; CS or CS-alt and TRAP; CS or CS-alt and CelTOS; CS or CS-alt and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS or CS-alt, LSA1 and TRAP; CS or CS-alt, LSA1 and CelTOS; CS or CS-alt, LSA1 and Ama1; LSA1, TRAP and CelTOS; LSA1, TRAP and Ama1; or TRAP, CelTOS and Ama1. Fusion proteins with four Consensus PF immunogens may comprise: CS or CS-alt, LSA1, TRAP and CelTOS; CS or CS-alt, LSA1, TRAP and Ama1; CS or CS-alt, LSA1, CelTOS and Ama1; CS or CS-alt, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1. In some embodiments, the fusion proteins comprise a signal peptide linked to the N terminus. In some embodiments, the fusion proteins comprises multiple signal peptides linked to the N terminal of each Consensus PF immunogens. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein wherein the spacer is a proteolyic cleavage site recognized by a protease found in cells to which the vaccine is intended to be administered and/or taken up and the fusion proteins comprises multiple signal peptides linked to the N terminal of each Consensus PF immunogens such that upon cleavage the signal peptide of each Consensus PF immunogens translocates the Consensus PF immunogen to outside the cell.

3. Coding Sequences Encoding Consensus PF Immunogens

Provided herein are nucleic acid sequences that encode the consensus PF immunogens. Administration of nucleic acid molecules comprising the nucleic acid sequences when taken up and expressed by cells results in a broad immune response against PF. Coding sequences for each six consensus PF immunogens disclosed above were prepared. Coding sequences for consensus PF proteins may encode SEQ ID NOs: 2, 4, 6, 8, 10 or 12, a fragment thereof as described herein, a homologous variant amino acid sequence as described herein, or a fragment of a homologous variant amino acid sequence. In some embodiments, the coding sequences that SEQ ID NOs: 2, 4, 6, 8, 10 or 12 may be a homologous variant nucleic acid sequence. In some embodiments, the coding sequences that encode a fragment of SEQ ID NOs: 2, 4, 6, 8, 10 or 12 may be a fragment of a homologous variant nucleic acid sequence. Coding sequences for consensus PF proteins may comprise SEQ ID NOs: 1, 3, 5, 7, 9 or 11, fragments thereof as described herein, a homologous variant nucleic acid sequence thereof as described herein that encodes a homologous variant amino acid sequence as described herein, or a fragment of a homologous variant nucleic acid sequence that encodes a fragment of a homologous variant amino acid sequence. Coding sequences for consensus PF proteins may comprise coding sequences for a signal peptide such as an immunoglobulin signal peptide such as an IgE or IgG signal peptide. Coding sequences may encode embodiments in which a consensus PF proteins SEQ ID NOs: 2, 4, 6, 8, 10 or 12 comprise an IgE signal peptide: SEQ ID NOs:14, 16, 18, 20, 22, 24, 26, 28, 30, 32, 34 and 36. Coding sequences may encode consensus PF proteins SEQ ID NOs: 2, 4, 6, 8, 10 or 12 that comprise an IgE signal peptide and an HA Tag: SEQ ID NOs: 26, 28, 30, 32, 34 and 36. Coding sequences SEQ ID NOs: 1, 3, 5, 7, 9 or 11 which comprise coding sequence for an IgE signal peptide include SEQ ID NOs:13, 15, 17, 19, 21, 23, 25, 27, 29, 31, 33 and 35. Coding sequences SEQ ID NOs: 1, 3, 5, 7, 9 or 11 which comprise coding sequence for an IgE signal peptide and an HA Tag include SEQ ID NOs: 25, 27, 29, 31, 33 and 35. Coding sequences may encode fusion proteins provided herein. The coding sequences may comprise SEQ ID NOs: 1, 3, 5, 7, 9 or 11, fragments thereof as described herein, a homologous variant nucleic acid sequence thereof as described herein that encodes a homologous variant amino acid sequence as described herein, or a fragment of a homologous variant nucleic acid sequence that encodes a fragment of a homologous variant amino acid sequence.

4. Plasmid

Provided herein is a vector that is capable of expressing a malaria antigen in the cell of a mammal in a quantity effective to elicit an immune response in the mammal. The vector may comprise heterologous nucleic acid encoding the malaria antigen. The vector may be a plasmid. The plasmid may be useful for transfecting cells with nucleic acid encoding a malaria antigen, which the transformed host cell is cultured and maintained under conditions wherein expression of the malaria antigen takes place.

Plasmids may comprise DNA constructs which comprise one or more coding sequences encoding Consensus PF Immunogens as disclosed herein. The coding sequences encoding Consensus PF Immunogens as disclosed herein are preferable operably linked to regulatory elements.

In some embodiments, a plasmid has DNA constructs that include coding sequence for one Consensus PF Immunogen, i.e. a Consensus PF CS Immunogen, a Consensus PF LSA1 Immunogen, a Consensus PF TRAP Immunogen, a Consensus PF CelTOS Immunogen, a Consensus PF Ama1 Immunogen or a Consensus PF CS-alt Immunogen.

In some embodiments, a plasmid has DNA constructs that include coding sequence for multiple Consensus PF Immunogens. In plasmid has DNA constructs that include coding sequence for multiple Consensus PF Immunogens the constructs may be separate expression cassettes wherein each Consensus PF Immunogen comprises a separate set of regulatory elements or two or more coding sequences may be incorporated into a single expression cassette in which coding sequences are separated by an IRS sequence.

In some embodiments, a plasmid has DNA constructs that include coding sequence for two Consensus PF Immunogens. Such plasmids may comprise DNA constructs that include coding sequence for CS or CS-alt and LSA1; CS or CS-alt and TRAP; CS or CS-alt and CelTOS; CS or CS-alt and Ama1; LSA1 and TRAP; LSA1 and CelTOS; LSA1 and Ama1; TRAP and CelTOS; TRAP and Ama1; or CelTOS and Ama1.

In some embodiments, a plasmid has DNA constructs that include coding sequence for three Consensus PF Immunogens. Such plasmids may comprise DNA constructs that include coding sequence for CS or CS-alt, LSA1 and TRAP; CS or CS-alt, LSA1 and CelTOS; CS or CS-alt, LSA1 and Ama1; LSA1, TRAP and CelTOS; LSA1, TRAP and Ama1; or TRAP, CelTOS and Ama1.

In some embodiments, a plasmid has DNA constructs that include coding sequence for four Consensus PF Immunogens. Such plasmids may comprise DNA constructs that include coding sequence for CS or CS-alt, LSA1, TRAP and CelTOS; CS or CS-alt, LSA1, TRAP and Ama1; CS or CS-alt, LSA1, CelTOS and Ama1; CS or CS-alt, TRAP, CelTOS and Ama1; or LSA1, TRAP, CelTOS and Ama1.

In some embodiments, a plasmid has DNA constructs that include coding sequence for five Consensus PF Immunogens. Such plasmids may comprise DNA constructs that include coding sequence for CS or CS-alt, LSA1, TRAP, CelTOS and Ama1.

Plasmid may comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which maybe used for protein production in mammalian cells such as Chinese hamster ovary (CHO) cells.

5. Compositions

Compositions are provided which comprise plasmids. The compositions may comprise a plurality of copies of a single nucleic acid molecule such a single plasmid, a plurality of copies of a two or more different nucleic acid molecules such as two or more different plasmids. For example a compositions may comprise plurality of one, two, three, four, five, six, seven, eight, nine or ten or more different nucleic acid molecules. Such a compositions may comprise plurality of one, two, three, four, five, six, seven, eight, nine or ten or more different plasmids. Compositions may comprise coding sequences for one or more of Consensus PF CS Immunogen, a Consensus PF LSA1 Immunogen, a Consensus PF TRAP Immunogen, a Consensus PF CelTOS Immunogen, a Consensus PF Ama1 Immunogen or a Consensus PF CS-alt Immunogen. Compositions may comprise nucleic acid molecules, such as plasmids, that collectively contain coding sequence for a single Consensus PF Immunogen, coding sequence for two Consensus PF Immunogens, coding sequence for three Consensus PF Immunogens, coding sequence for four Consensus PF Immunogen or coding sequence for five Consensus PF Immunogens Compositions comprising coding sequence two Consensus PF Immunogens may be on a single nucleic acid molecule such as a single plasmid or the compositions may comprise two different nucleic acid molecule such as two different plasmids wherein one nucleic acid molecule comprises the coding sequence one Consensus PF Immunogen and the other nucleic acid molecule comprises the coding sequence different Consensus PF Immunogen. Similarly, compositions comprising coding sequence three Consensus PF Immunogens may comprise a single nucleic acid molecule such as a single plasmid, two different nucleic acid molecules or three different nucleic acid molecules. Likewise, compositions comprising coding sequence four Consensus PF Immunogens may comprise a single nucleic acid molecule such as a single plasmid, two different nucleic acid molecules, three different nucleic acid molecules or four different nucleic acid molecule. Compositions comprising coding sequence five Consensus PF Immunogens may comprise a single nucleic acid molecule such as a single plasmid, two different nucleic acid molecules, three different nucleic acid molecules, four different nucleic acid molecules or five different nucleic acid molecules.

In some embodiments, a composition comprises a plurality single nucleic acid molecule encoding one Consensus PF Immunogen such as Consensus PF CS or CS-alt Immunogen, Consensus PF LAST Immunogen, Consensus PF TRAPImmunogen, Consensus PF CelTOS Immunogen or Consensus PF Ama1 immunogen. In some embodiments, a composition comprises a plurality single nucleic acid molecule, such a single plasmid encoding two Consensus PF Immunogens such as CS or CS-alt and LSA1; CS or CS-alt and TRAP; CS or CS-alt and CelTOS; CS or CS-alt and Ama1; LSA1 and TRAP; LSA1 and CelTOS; LSA1 and Ama1; TRAP and CelTOS; TRAP and Ama1; or CelTOS and Ama1. In some embodiments, a composition comprises a plurality single nucleic acid molecule, such a single plasmid encoding three Consensus PF Immunogens such as CS or CS-alt, LSA1 and TRAP; CS or CS-alt, LSA1 and CelTOS; CS or CS-alt, LSA1 and Ama1; LSA1, TRAP and CelTOS; LSA1, TRAP and Ama1; or TRAP, CelTOS and Ama1. In some embodiments, a composition comprises a plurality single nucleic acid molecule, such a single plasmid encoding four Consensus PF Immunogens: CS or CS-alt, LSA1, TRAP and CelTOS; CS or CS-alt, LSA1, TRAP and Ama1; CS or CS-alt, LSA1, CelTOS and Ama1; CS or CS-alt, TRAP, CelTOS and Ama1; or LSA1, TRAP, CelTOS and Ama1. In some embodiments, a composition comprises a plurality single nucleic acid molecule, such a single plasmid encoding five Consensus PF Immunogens: CS or CS-alt, LSA1, TRAP, CelTOS and Ama1

In some embodiments, a composition comprises a plurality two different nucleic acid molecules, such as two plasmids, each different nucleic acid molecule comprising a single different coding sequence for a different Consensus PF Immunogens wherein pairs of different nucleic acid molecule comprise CS or CS-alt and LSA1; CS or CS-alt and TRAP; CS or CS-alt and CelTOS; CS or CS-alt and Ama1; LSA1 and TRAP; LSA1 and CelTOS; LSA1 and Ama1; TRAP and CelTOS; TRAP and Ama1; or CelTOS and Ama1. Collectively, the two different plasmids encode two different Consensus PF immunogens.

In some embodiments, a composition comprises a plurality two different nucleic acid molecules, such as two plasmids, which collectively comprising coding sequence for three different Consensus PF Immunogens. In some embodiments: one nucleic acid molecule encodes one Consensus PF Immunogen selected from CS, CS-alt, LSA1, TRAP, CelTOS and Ama1 and the second encodes two Consensus PF Immunogen selected from CS or CS-alt, LSA1, TRAP, CelTOS and Ama1. Collectively, the two different plasmids encode three different Consensus PF immunogens.

In some embodiments, a composition comprises a plurality two different nucleic acid molecules, such as two plasmids, which collectively comprising coding sequence for four different Consensus PF Immunogens. In some embodiments: one nucleic acid molecule encodes one Consensus PF Immunogen selected from CS, CS-alt, LSA1, TRAP, CelTOS and Ama1 and the second encodes three Consensus PF Immunogen selected from CS or CS-alt, LSA1, TRAP, CelTOS and Ama1. In some embodiments: one nucleic acid molecule encodes two Consensus PF Immunogens selected from CS, CS-alt, LSA1, TRAP, CelTOS and Ama1 and the second encodes two Consensus PF Immunogen selected from CS or CS-alt, LSA1, TRAP, CelTOS and Ama1. Collectively, the two different plasmids encode four different Consensus PF immunogens.

In some embodiments, a composition comprises a plurality two different nucleic acid molecules, such as two plasmids, which collectively comprising coding sequence for five different Consensus PF Immunogens. In some embodiments: one nucleic acid molecule encodes two Consensus PF Immunogen selected from CS, CS-alt, LSA1, TRAP, CelTOS and Ama1 and the second encodes three Consensus PF Immunogen selected from CS or CS-alt, LSA1, TRAP, CelTOS and Ama1. In some embodiments: one nucleic acid molecule encodes two Consensus PF Immunogens selected from CS, CS-alt, LSA1, TRAP, CelTOS and Ama1 and the second encodes two Consensus PF Immunogen selected from CS or CS-alt, LSA1, TRAP, CelTOS and Ama1. Collectively, the two different plasmids encode five different Consensus PF immunogens.

In some embodiments, a composition comprises a plurality three different nucleic acid molecules, such as three plasmids, which collectively comprising coding sequence for three different Consensus PF Immunogens. In some embodiments: one nucleic acid molecule encodes one Consensus PF Immunogen selected from CS, CS-alt, LSA1, TRAP, CelTOS and Ama1, the second encodes one Consensus PF Immunogen selected from CS or CS-alt, LSA1, TRAP, CelTOS and Ama1, and the third encodes one Consensus PF Immunogen selected from CS or CS-alt, LSA1, TRAP, CelTOS and Ama1. Collectively, the three different plasmids encode three different Consensus PF immunogens.

In some embodiments, a composition comprises a plurality three different nucleic acid molecules, such as three plasmids, which collectively comprising coding sequence for four different Consensus PF Immunogens. In some embodiments: one nucleic acid molecule encodes one Consensus PF Immunogen selected from CS, CS-alt, LSA1, TRAP, CelTOS and Ama1, the second encodes one Consensus PF Immunogen selected from CS or CS-alt, LSA1, TRAP, CelTOS and Ama1, and the third encodes two Consensus PF Immunogen selected from CS or CS-alt, LSA1, TRAP, CelTOS and Ama1. Collectively, the three different plasmids encode four different Consensus PF immunogens.

In some embodiments, a composition comprises a plurality three different nucleic acid molecules, such as three plasmids, which collectively comprising coding sequence for five different Consensus PF Immunogens. In some embodiments: one nucleic acid molecule encodes one Consensus PF Immunogen selected from CS, CS-alt, LSA1, TRAP, CelTOS and Ama1, the second encodes one Consensus PF Immunogen selected from CS or CS-alt, LSA1, TRAP, CelTOS and Ama1, and the third encodes three Consensus PF Immunogen selected from CS or CS-alt, LSA1, TRAP, CelTOS and Ama1. In some embodiments: one nucleic acid molecule encodes one Consensus PF Immunogen selected from CS, CS-alt, LSA1, TRAP, CelTOS and Ama1, the second encodes two Consensus PF Immunogen selected from CS or CS-alt, LSA1, TRAP, CelTOS and Ama1, and the third encodes two Consensus PF Immunogen selected from CS or CS-alt, LSA1, TRAP, CelTOS and Ama1. Collectively, the three different plasmids encode five different Consensus PF immunogens.

In some embodiments, a composition comprises a plurality four different nucleic acid molecules, such as four plasmids, which collectively comprising coding sequence for four different Consensus PF Immunogens. In some embodiments: one nucleic acid molecule encodes one Consensus PF Immunogen selected from CS, CS-alt, LSA1, TRAP, CelTOS and Ama1, the second encodes one Consensus PF Immunogen selected from CS or CS-alt, LSA1, TRAP, CelTOS and Ama1, the third encodes one Consensus PF Immunogen selected from CS or CS-alt, LSA1, TRAP, CelTOS and Ama1, and the fourth encodes one Consensus PF Immunogen selected from CS or CS-alt, LSA1, TRAP, CelTOS and Ama1. Collectively, the four different plasmids encode four different Consensus PF immunogens.

In some embodiments, a composition comprises a plurality four different nucleic acid molecules, such as four plasmids, which collectively comprising coding sequence for five different Consensus PF Immunogens. In some embodiments: one nucleic acid molecule encodes one Consensus PF Immunogen selected from CS, CS-alt, LSA1, TRAP, CelTOS and Ama1, the second encodes one Consensus PF Immunogen selected from CS or CS-alt, LSA1, TRAP, CelTOS and Ama1, the third encodes one Consensus PF Immunogen selected from CS or CS-alt, LSA1, TRAP, CelTOS and Ama1, and the fourth encodes two Consensus PF Immunogens selected from CS or CS-alt, LSA1, TRAP, CelTOS and Ama1. Collectively, the four different plasmids encode five different Consensus PF immunogens.

In some embodiments, a composition comprises a plurality five different nucleic acid molecules, such as four plasmids, which collectively comprising coding sequence for five different Consensus PF Immunogens. In some embodiments: one nucleic acid molecule encodes one Consensus PF Immunogen selected from CS, CS-alt, LSA1, TRAP, CelTOS and Ama1, the second encodes one Consensus PF Immunogen selected from CS or CS-alt, LSA1, TRAP, CelTOS and Ama1, the third encodes one Consensus PF Immunogen selected from CS or CS-alt, LSA1, TRAP, CelTOS and Ama1, the fourth encodes one Consensus PF Immunogen selected from CS or CS-alt, LSA1, TRAP, CelTOS and Ama1, and the fifth encodes one Consensus PF Immunogen selected from CS or CS-alt, LSA1, TRAP, CelTOS and Ama1. Collectively, the five different plasmids encode five different Consensus PF immunogens.

In some embodiments, a composition further comprises coding sequence for IL-12, IL-15, IL-28B and/or RANTES. Coding sequence for IL-12, IL-15, IL-28B and/or RANTES may be included on one or more nucleic acid molecules that comprise coding sequence for one or more Consensus PF Immunogens. Coding sequence for IL-12, IL-15, IL-28B and/or RANTES may be included on a separate nucleic acid molecules such as a separate plasmid.

6. Vaccine

Provided herein is a vaccine capable of generating in a mammal an immune response against malaria. The vaccine may comprise each plasmid as discussed above. The vaccine may comprise a plurality of the plasmids, or combinations thereof. The vaccine may be provided to induce a therapeutic or prophylactic immune response.

Vaccines may be used to deliver one or more Consensus PF Immunogens selected from the group consisting of Consensus PF CS Immunogen, a Consensus PF LSA1 Immunogen, a Consensus PF TRAP Immunogen, a Consensus PF CelTOS Immunogen, a Consensus PF Ama1 Immunogen or a Consensus PF CS-alt Immunogen. In the case of delivery of multiple targets, vaccines may include multiple compositions or a single compositions. Plasmids may be used which encode multiple proteins on a single plasmid or compositions which comprise different plasmids that encode different proteins.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the vaccine. The one or more adjuvants may be proteins and/or nucleic acid molecules that encode proteins selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, AK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. or a combination thereof. In some embodiments adjuvant may be one or more proteins and/or nucleic acid molecules that encode proteins selected from the group consisting of: IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048,827, which are each incorporated herein by reference. Examples of IL-28 constructs and sequences are disclosed in PCT application no. PCT/US09/039,648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. and 09/622,452, which are each incorporated herein by reference. Other examples of RANTES constructs and sequences are disclosed in PCT application no. PCT/US11/024,098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024,098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The vaccine may further comprise a genetic vaccine facilitator agent as described in U.S. Ser. No. 021,579 filed Apr. 1, 1994, which is fully incorporated by reference.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

7. Methods of Delivery the Vaccine

Provided herein is a method for delivering the vaccine for providing genetic constructs and proteins of the consensus antigen which comprise epitopes that make them particular effective against immunogens of malaria against which an immune response can be induced. The method of delivering the vaccine or vaccination may be provided to induce a therapeutic and prophylactic immune response. The vaccination process may generate in the mammal an immune response against malaria. The vaccine may be delivered to an individual to modulate modulate the activity of the mammal's immune system and enhance the immune response. The delivery of the vaccine may be the transfection of the consensus antigen as a nucleic acid molecule that is expressed in the cell and delivered to the surface of the cell upon which the immune system recognized and induces a cellular, humoral, or cellular and humoral response. The delivery of the vaccine may be use to induce or elicit and immune response in mammals against malaria by administering to the mammals the vaccine as discussed above.

Upon delivery of the vaccine and plasmid into the cells of the mammal, the transfected cells will express and secrete consensus antigens for each of the plasmids injected from the vaccine. These proteins will be recognized as foreign by the immune system and antibodies will be made against them. These antibodies will be maintained by the immune system and allow for an effective response to subsequent malaria infections.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The vaccine may be administered in combination with other proteins and/or genes encoding α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of IL-12, IL-15, IL-28, CTACK, TECK, MEC and RANTES or functional fragments thereof, and proteins selected from the group consisting of: IL-12 protein, IL-15 protein, IL-28 protein, CTACK protein, TECK protein, MEC protein or RANTES protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Protein Boost

In some embodiments, Consensus PF immunogen may be delivered as protein as part of vaccine protocol. In some embodiments, subsequent to the initial immunization vaccination in which plasmid DNA compositions as disclosed herein are administered, protein immunogens are delivered as a boost. In some embodiments, boosts are combinations of plasmid DNA vaccine and protein. In some embodiments, multiple boosts are administered. In some embodiments, multiple boosts are administered wherein one or more boosts are protein administration and one or more boosts a DNA vaccine administration. Boosts employing viral vectors and/or killed or attenuated pathogen may also be employed. One or more vaccinations may be administered, independent with respect to all times other than the initial or most recent, within one day, one week, two weeks, three weeks, four weeks, six weeks, eight weeks, twelve weeks, six months, one year apart.

Proteins used in protein boosts may be produced by routine methods using the information disclosed herein and well known methodology. For example. recombinant vectors that include coding sequences for the proteins may be produced and used to generate large quantities of protein. Recombinant expression vectors that comprises a nucleotide sequence that encodes proteins of the invention can be produced routinely. As used herein, the term "recombinant expression vector" is meant to refer to a plasmid, phage, viral particle or other vector which, when introduced into an appropriate host, contains the necessary genetic elements to direct expression of a coding sequence. One having ordinary skill in the art can isolate or synthesize a nucleic acid molecule that encodes a protein of the invention and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts.

Host cells that comprise the recombinant expression vector can be used to produce the protein. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of a protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce proteins of the invention using routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., Molecular Cloning a Laboratory Manual, Second Ed. Cold Spring Harbor Press (1989).

The expression vector including the DNA that encodes a protein is used to transform the compatible host which is then cultured and maintained under conditions wherein expression of the foreign DNA takes place. The protein of the invention thus produced is recovered from the culture, either by lysing the cells or from the culture medium as appropriate and known to those in the art. One having ordinary skill in the art can, using well known techniques, isolate the protein of the invention that is produced using such expression systems. The methods of purifying proteins of the invention from natural sources using antibodies which specifically bind to such protein are routine as is the methods of generating such antibodies (See: Harlow, E. and Lane, E., Antibodies: A Laboratory Manual, 1988, Cold Spring Harbor Laboratory Press which is incorporated herein by reference). Such antibodies may be used to purifying proteins produced by recombinant DNA methodology or natural sources.

Examples of genetic constructs include coding sequences which encode a protein of the invention and which are operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes proteins of the invention from readily available starting materials. Such gene constructs are useful for the production of proteins of the invention.

In addition to producing proteins of the invention by recombinant techniques, automated peptide synthesizers may also be employed to produce proteins of the invention. Such techniques are well known to those having ordinary skill in the art and are useful if derivatives which have substitutions not provided for in DNA-encoded protein production. For example, the proteins of the invention may be prepared by any of the following known techniques. Conveniently, the proteins of the invention may be prepared using the solid-phase synthetic technique initially described by Merrifield, in J. Am. Chem. Soc., 15:2149-2154 (1963) which is incorporated herein by reference. Other protein synthesis techniques may be found, for example, in M. Bodanszky et al., (1976) Peptide Synthesis, John Wiley & Sons, 2d Ed. which is incorporated herein by reference; Kent and Clark-Lewis in Synthetic Peptides in Biology and Medicine, p. 295-358, eds. Alitalo, K., et al. Science Publishers, (Amsterdam, 1985) which is incorporated herein by reference; as well as other reference works known to those skilled in the art. A summary of synthesis techniques may be found in J. Stuart and J. D. Young, Solid Phase Peptide Synthelia, Pierce Chemical Company, Rockford, Ill. (1984) which is incorporated herein by reference. Synthesis by solution methods may also be used, as described in The Proteins, Vol. II, 3d Ed., p. 105-237, Neurath, H. et al., Eds., Academic Press, New York, N.Y. (1976) which is incorporated herein by reference. Appropriate protective groups for use in such syntheses will be found in the above texts, as well as in J. F. W. McOmie, Protective Groups in Organic Chemistry, Plenum Press, New York, N.Y. (1973) which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Proteins may be formulated for administration to a mammal by well known methods using readily available materials. One skilled in the art would readily comprehend the multitude of pharmaceutically acceptable media that may be used in the present invention. Suitable pharmaceutical carriers are described in Remington's Pharmaceutical Sciences, A. Osol, a standard reference text in this field, which is incorporated herein by reference. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or nonaqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free. For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions comprising protein according to the present invention may be administered as a single dose or in multiple doses. Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art. Usually, the dosage of peptide can be about 1 micrograms to 1000 milligrams or more; 10 micrograms to 1000 milligrams; preferably 50 micrograms to 500 milligrams; more preferably 100 micrograms to 400 milligrams. In some embodiments, dosages are in the rage of 10-250 micrograms. In some embodiments, dosages are higher, for example 250 micrograms-1 milligram, or higher such as 1-50 milligrams. In some embodiments, dosages are higher still, for example 50-500 milligrams.

d. Method of Preparing DNA Plasmids

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims

Example 1—Preparing Expression Constructs

Vaccine candidates were developed based on identifying four important P.f. antigens: circumsporozoite protein (CS), liver stage antigen 1 (LSA1), thrombospondin-related-anonymous-protein (TRAP) and cell-traversal protein for ookinetes and sporozoites (CelTOS, or Ag2). Each antigen was designed based on consensus sequence with several modifications made in order to improve expression, including codon and RNA optimization.

Consensus CS

A consensus CS sequence was designed from full-length CS sequences in the GenBank database (66 sequences in total) disclosed in FIG. 1. The consensus CS sequence may optionally comprise a leader sequence such as an immunoglobulin signal peptide such as the IgE signal peptide. The consensus CS is set forth in SEQ ID NO:2. The coding sequence of the consensus CS set forth in SEQ ID NO:2 is set forth in SEQ ID NO:1. Consensus CS with an IgE leader sequence is set forth in SEQ ID NOs:14 and 26. Coding sequences of consensus CS with an IgE leader sequence in SEQ ID NOs:14 and 26 are set forth in SEQ ID NOs:13 and 25. The coding sequence set forth in SEQ ID NO:25 cloned in pVAX to produce pGX7002 has the sequence set forth in SEQ ID NO:37.

Consensus Ag2 (or Consensus CelTOS)

A consensus CelTOS sequence, also referred to as the consensus Ag2 sequence, was designed from full-length CelTOS sequence in the GenBank database disclosed in FIG. 4. The consensus CelTOS is set forth in SEQ ID NO:8. A sequence encoding the consensus CelTOS designed for high level expression of SEQ ID NO:8 is set forth in SEQ ID NO:7. The consensus CelTOS sequence may optionally comprise a leader sequence such as an immunoglobulin signal peptide such as the IgE signal peptide. Consensus CelTOS with an IgE leader sequence are set forth in SEQ ID NOs:20 and 32. Sequence encoding consensus CelTOS with an IgE leader sequence designed for high level expression of SEQ ID NOs:20 and 32 are set forth in SEQ ID NOs:19 and 31. The coding sequence set forth in SEQ ID NO:31 cloned in pVAX to produce pGX7001 has the sequence set forth in SEQ ID NO:39.

Consensus LSA1

A consensus LAS sequence was designed from full-length LAS1 sequences. FIG. 2 shows the degree of homology between SEQ ID NO:4 and the sequences. While the full length LSA1 sequence contains multiple repeat regions in the center of the protein, the consensus LSA1 (PfConLSA1) contains only 8 of these repeat regions. The consensus LAS1 is set forth in SEQ ID NO:4. The coding sequence of the consensus LAS1 in SEQ ID NO:4 is set forth in SEQ ID NO:3. The consensus LAS1 sequence may optionally comprise a leader sequence such as an immunoglobulin signal peptide such as the IgE signal peptide. Consensus LAS 1 with an IgE leader sequence are set forth in SEQ ID NOs:16 and 28. Coding sequences of consensus LAS1 with an IgE leader sequence in SEQ ID NOs:16 and 28 are set forth in SEQ ID NOs:15 and 27. The coding sequence set forth in SEQ ID NO:27 cloned in pVAX to produce pGX7004 has the sequence set forth in SEQ ID NO:39.

Consensus TRAP (Consensus SSP2)

A consensus TRAP sequence, also referred to as the consensus SSP2 sequence, was designed from full-length TRAP sequences in the GenBank database (28 sequences in total) disclosed in FIG. 3. The consensus TRAP is set forth in SEQ ID NO:6. A sequence encoding the consensus TRAP designed for high level expression is set forth in SEQ ID NO:6 is set forth in SEQ ID NO:5. The consensus TRAP sequence may optionally comprise a leader sequence such as an immunoglobulin signal peptide such as the IgE signal peptide. Consensus TRAP with an IgE leader sequence are set forth in SEQ ID NOs:18 and 30. Sequences encoding consensus TRAP with an IgE leader sequence designed for high level expression of SEQ ID NOs:18 and 30 are set forth in SEQ ID NOs:17 and 29. The coding sequence set forth in SEQ ID NO:29 cloned in pVAX to produce pGX7005 has the sequence set forth in SEQ ID NO:40.

Alternative Consensus CS (CS-alt)

Figure 11:
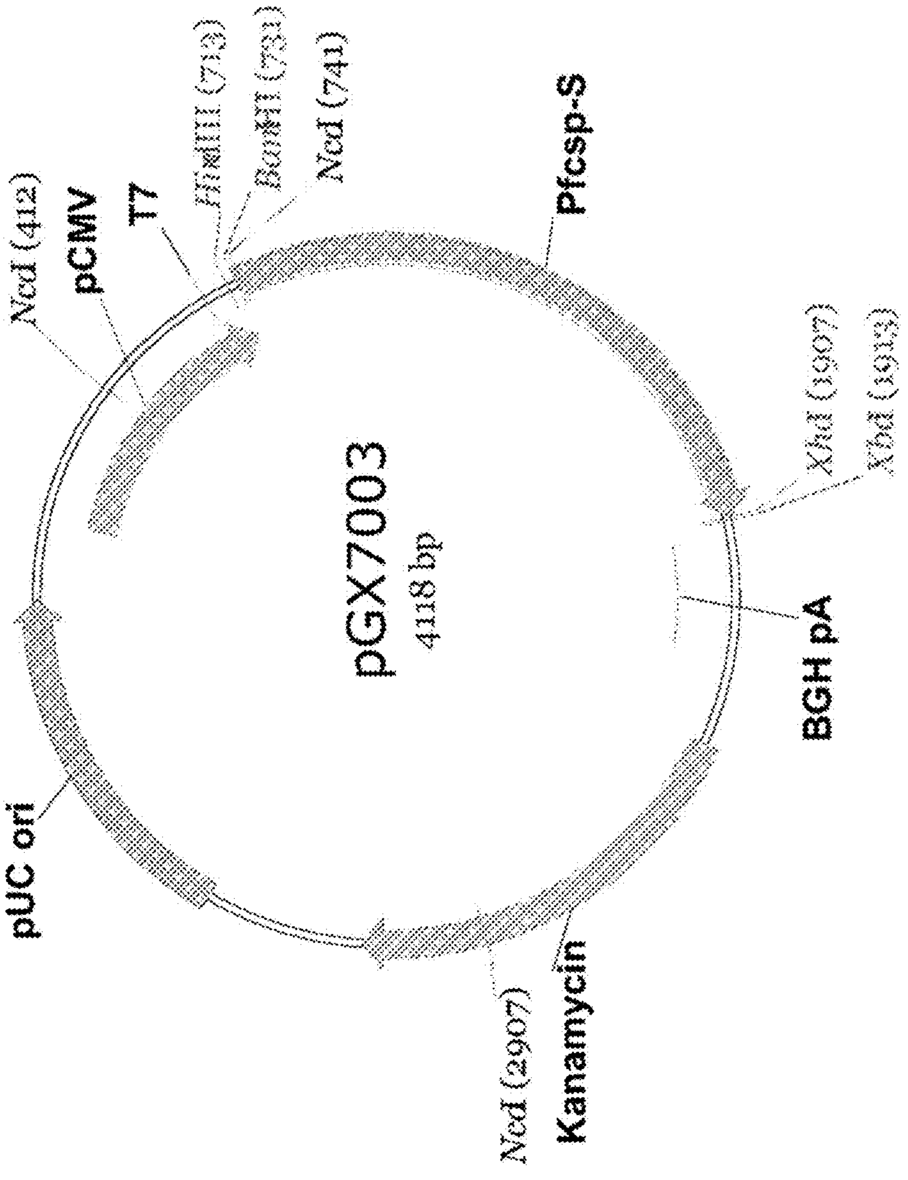
FIG. 11 displays a plasmid map of expression construct pGX7003 (SEQ ID NO:41), Plasmid pGX7003 includes coding sequence PfConCS-alt including the IgE signal peptide and HA Tag (SEQ ID NO:35, which encodes SEQ ID NO:36). The alternative consensus CS-alt full length consensus amino acid sequence (without signal peptide or HA Tag) is SEQ ID NO:12 which is encoded by SEQ ID NO:11.

An alternative consensus CS was generated having the sequence SEQ ID NO:12. The coding sequence of SEQ ID NO:12 is SEQ ID NO:11. The consensus CS-alt sequence may optionally comprise a leader sequence such as an immunoglobulin signal peptide such as the IgE signal peptide. Consensus CS-alt with an IgE leader sequence are set forth in SEQ ID NOs:22 and 34. Sequences encoding consensus CS-alt with an IgE leader sequence designed for high level expression of SEQ ID NOs:22 and 34 are set forth in SEQ ID NOs:21 and 33. The consensus sequence in SEQ ID NO:33 was inserted into an expression vector based on pVAX, and is shown in FIG. 11 as expression construct pGX7003 (SEQ ID NO:41).

Example 2—Expression of Consensus Antigens

The cloned expression constructs were then expressed with an in vitro translation assay, and protein expression was determined by western blot analysis. The plasmids were transfected into RD cells with lipofectamine. Twenty hours later, cells were harvested and total cell lysate was obtained. Protein was quantified and electrophoresed on a 12% SDS-PAGE gel. The sysnthesized proteins were detected using an anti-HA antibody (the HA tag is contained in the C-terminus of the antigen sequences). pVAX 1 was used as a negative control. The results are shown in FIG. 5.

Example 3—Immune Response in Vaccinated Mice

For cellular immunogenicity studies, 10 or 20 μg of each antigen-encoding plasmid was delivered to the tibialis anterior muscle of Balb/c mice by intramuscular injection followed by electroporation using the CELLECTRA adaptive constant current electroporation device (Inovio Pharmaceuticals, Blue Bell Pa.). Mice (n=5 per group) received 3 immunizations at weeks 0, 3 and 6. Cellular and responses were assessed 1 week after the last immunization (week 5). ELISpots were carried out per manufacturers instructions (R&D Systems) using 96-well plates (Millipore). $2\times10^5$ splenocytes from each immunized mouse were added to each well of the plates and stimulated overnight at 37° C., 5% $CO_2$, in the presence of R10 (negative control), concanavalin A (positive control), or peptide pools specific to each antigen. Peptide pools are composed of 15-mer peptides spanning the entire protein, overlapping by 11 amino acids.

Figure 6A:
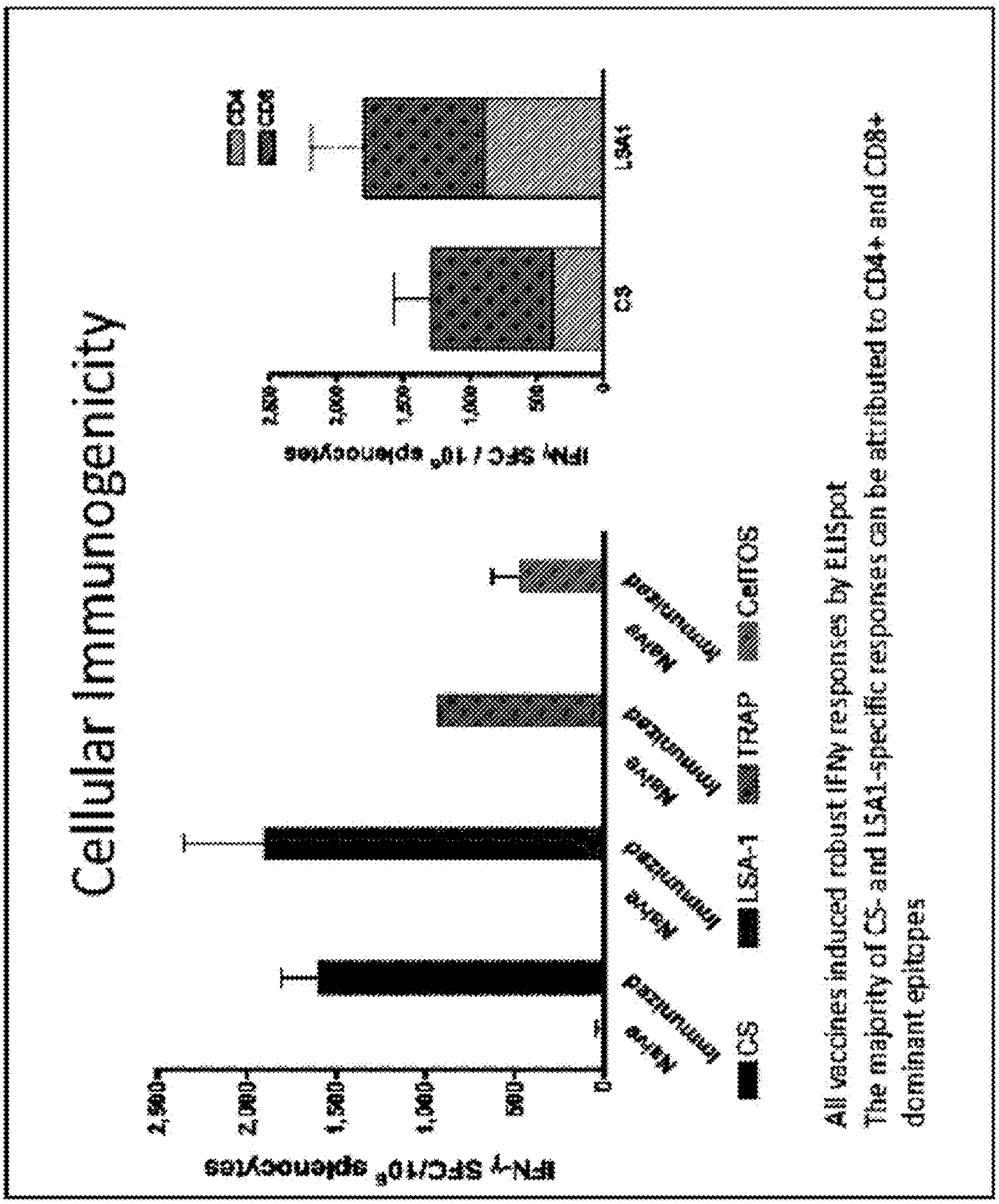
FIGS. 6A-6I include data from immunological analyses of immunized mice and its sera. P.f. consensus immunogen constructs used included nucleic acid sequences (SEQ ID NOs:25, 27, 29 and 31 which encode SEQ ID NOs:26, 28, 30 and 32 respectively, which correspond to SEQ ID NOs:2, 4, 6 and 8, respectively linked to the IgE signal peptide and HA Tag.
Figure 6B:
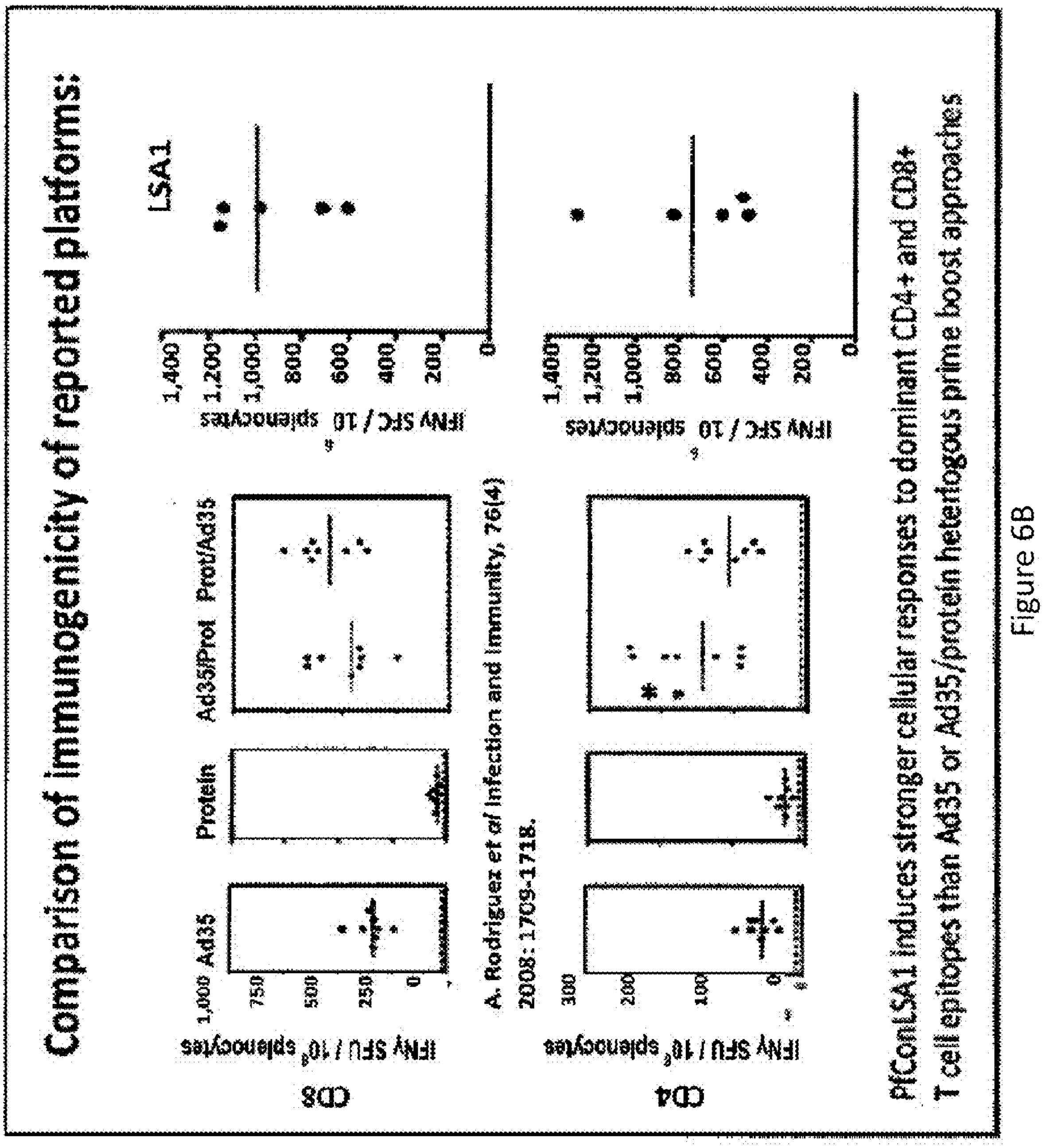
Figure 6C:
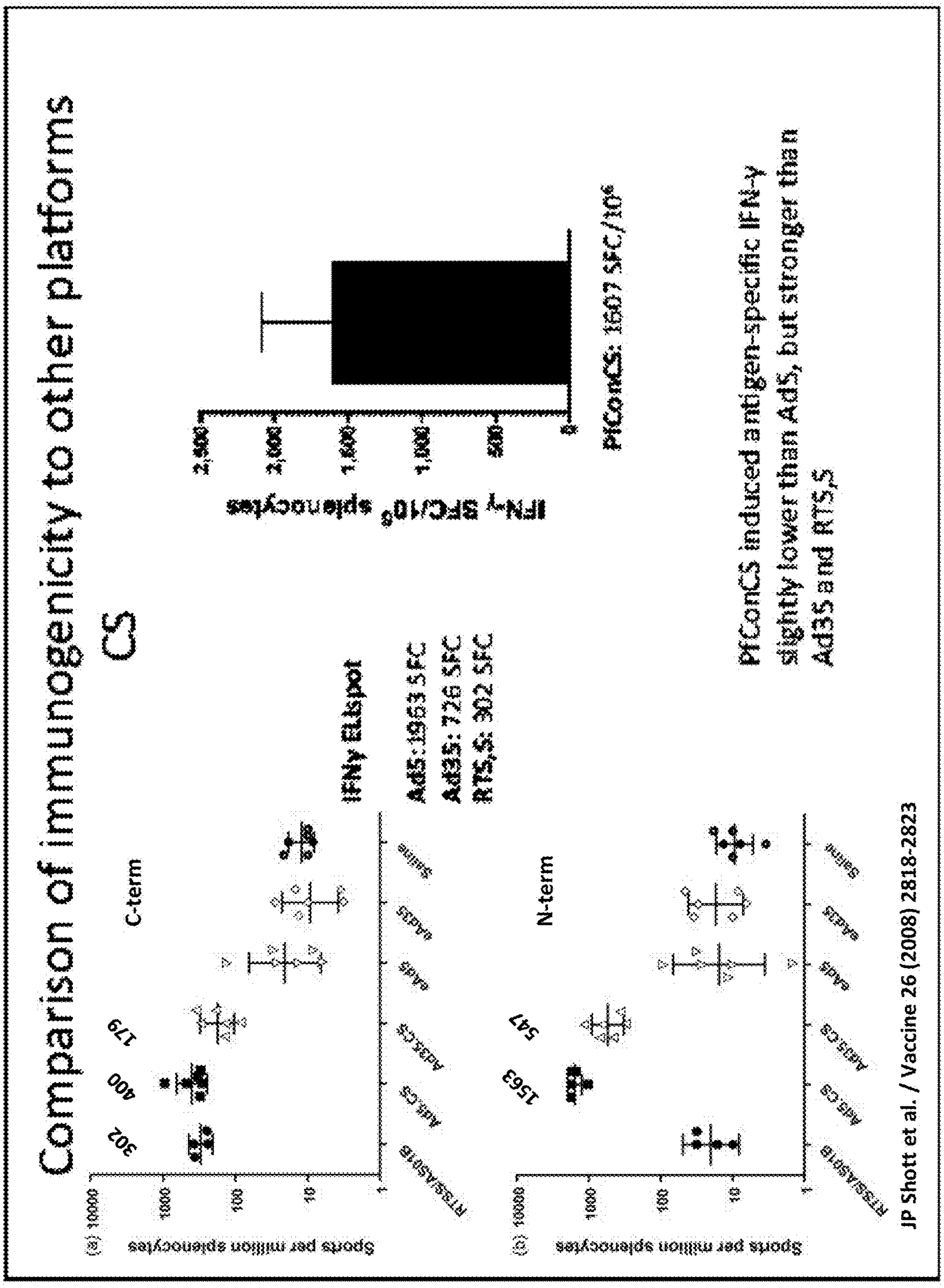
Figure 6D:
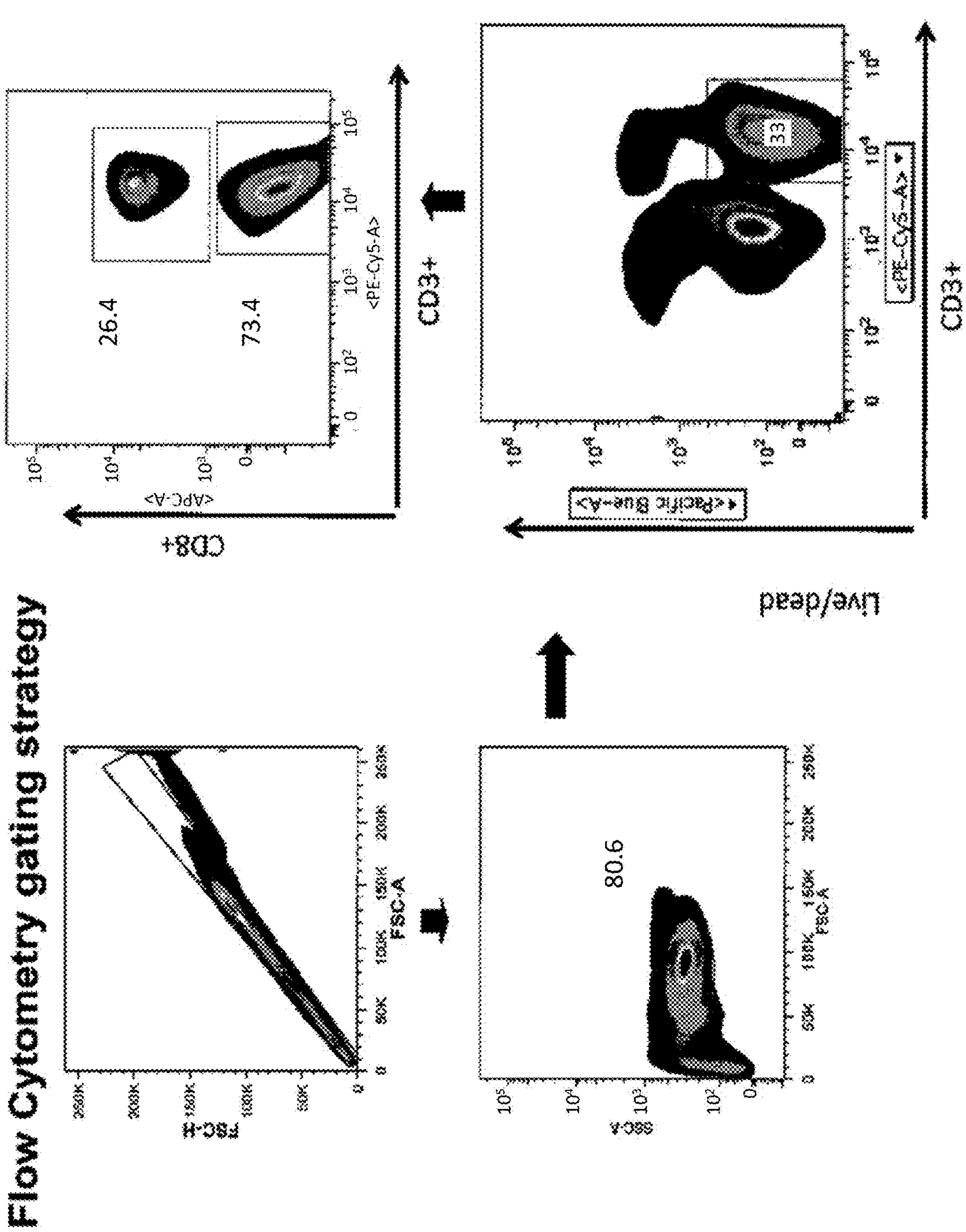
Figure 6D:
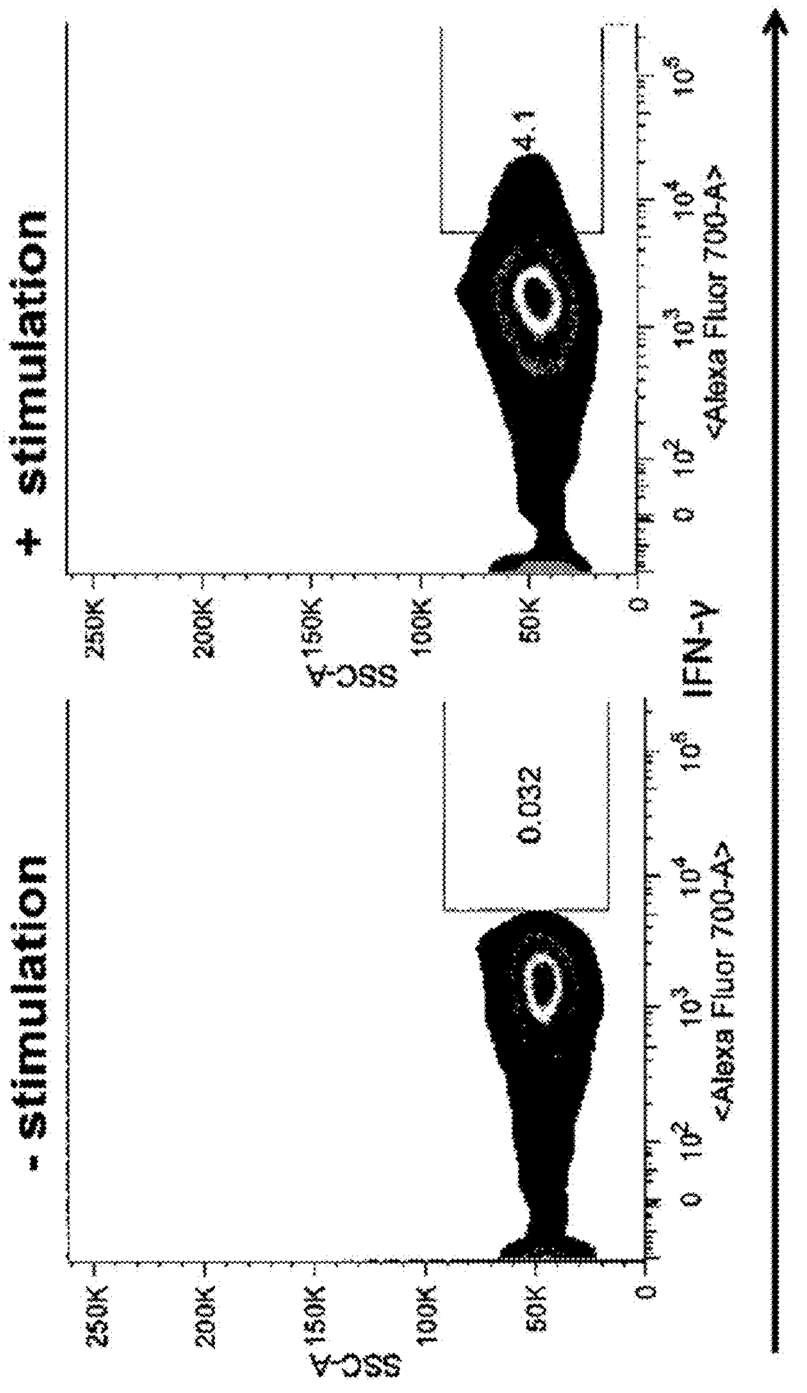
Figure 6D:
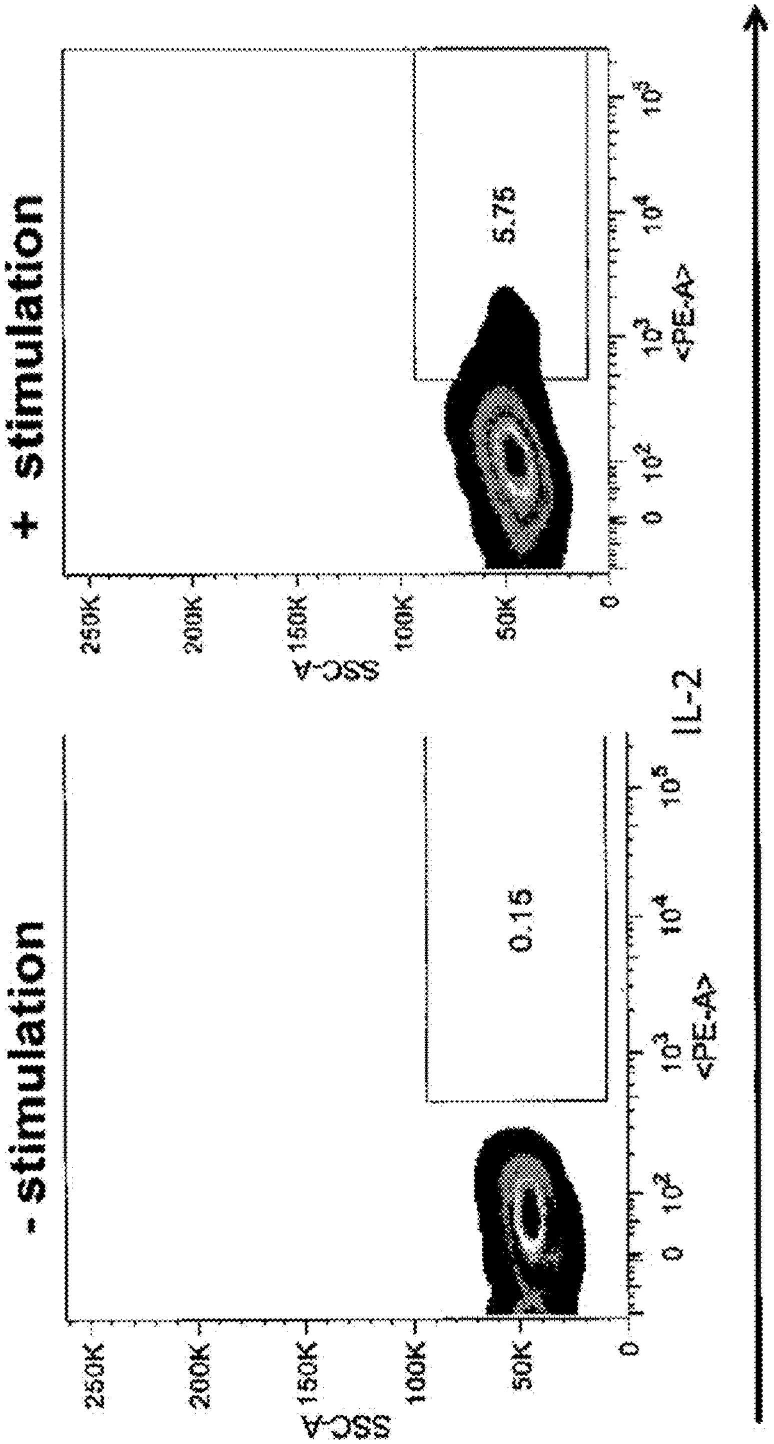
Figure 6D:
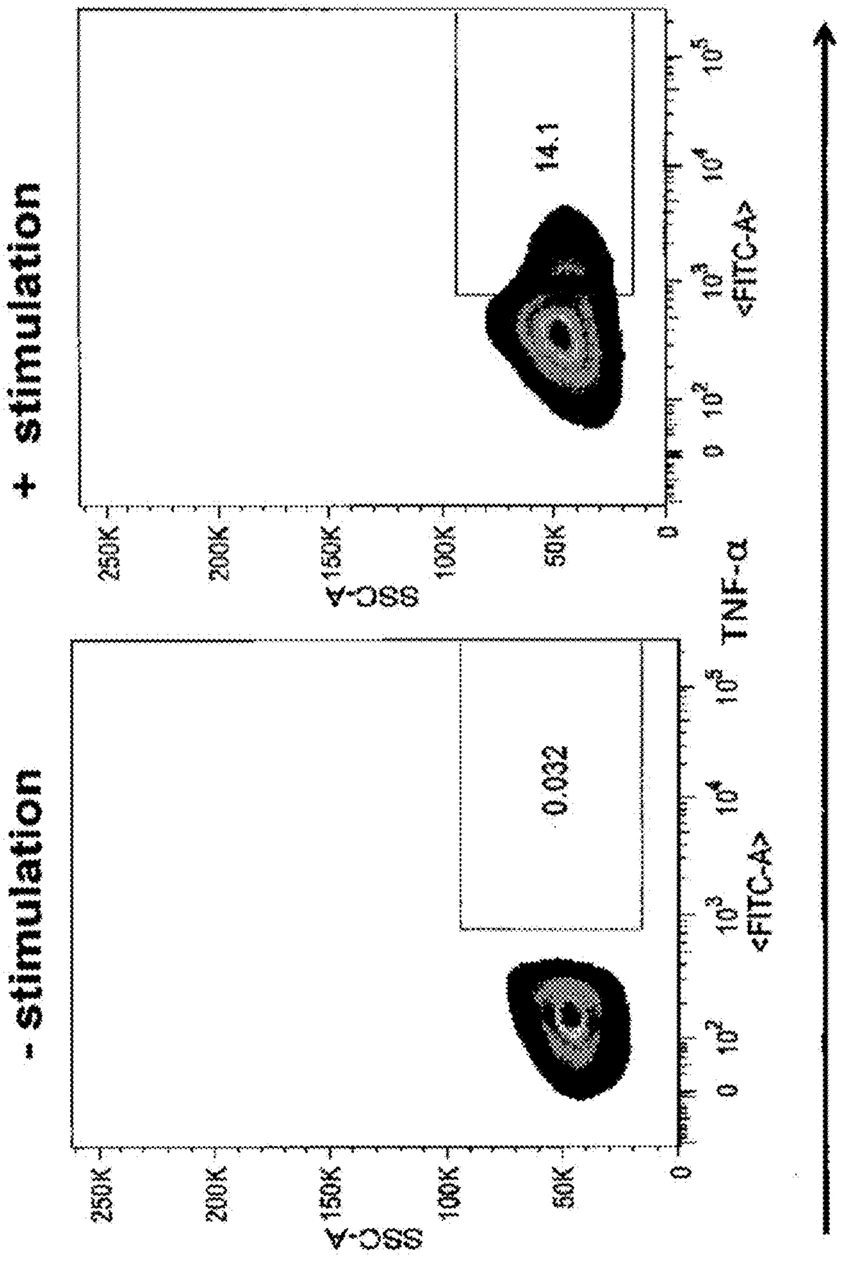
Figure 6E:
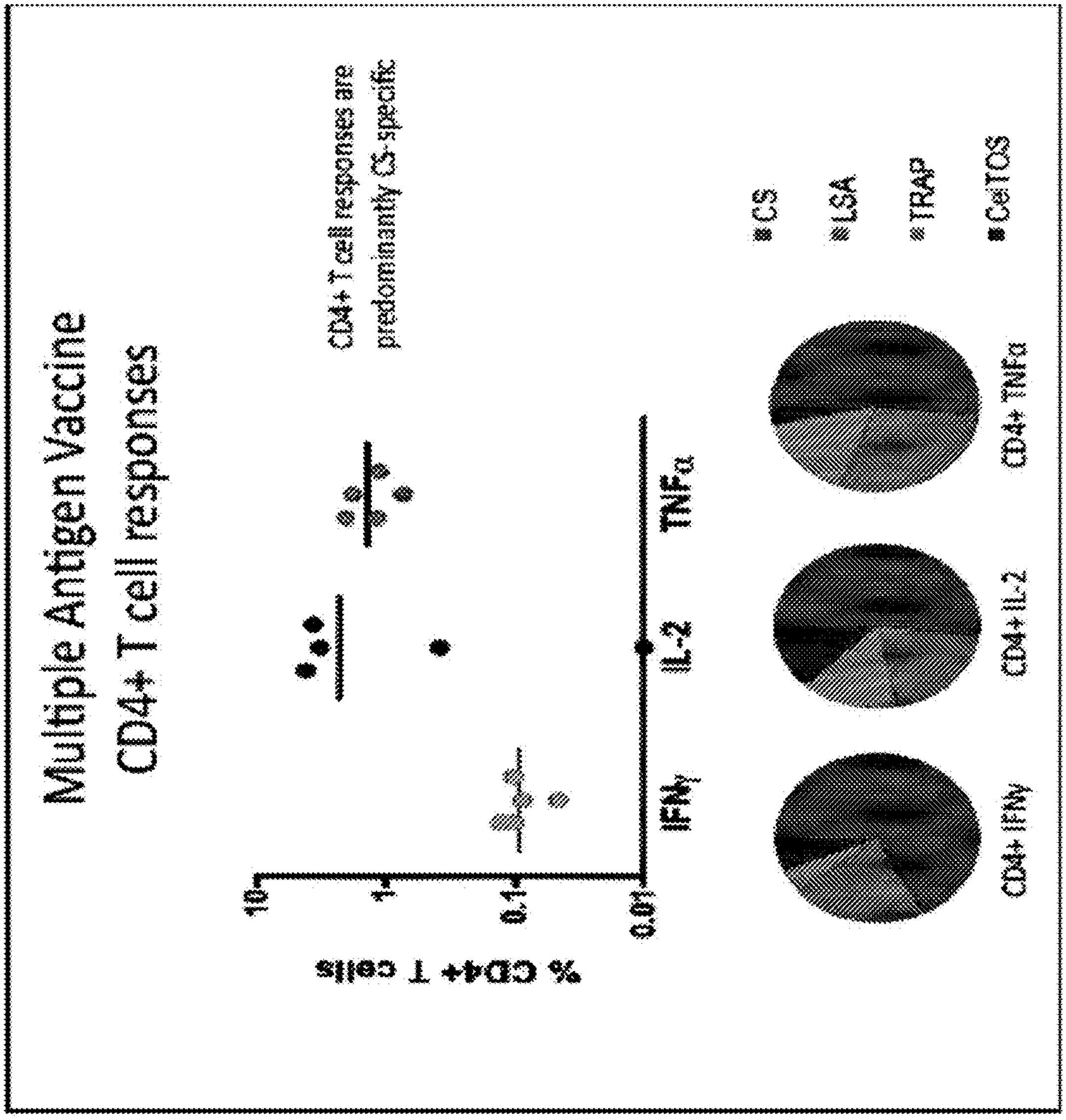
Figure 6F:
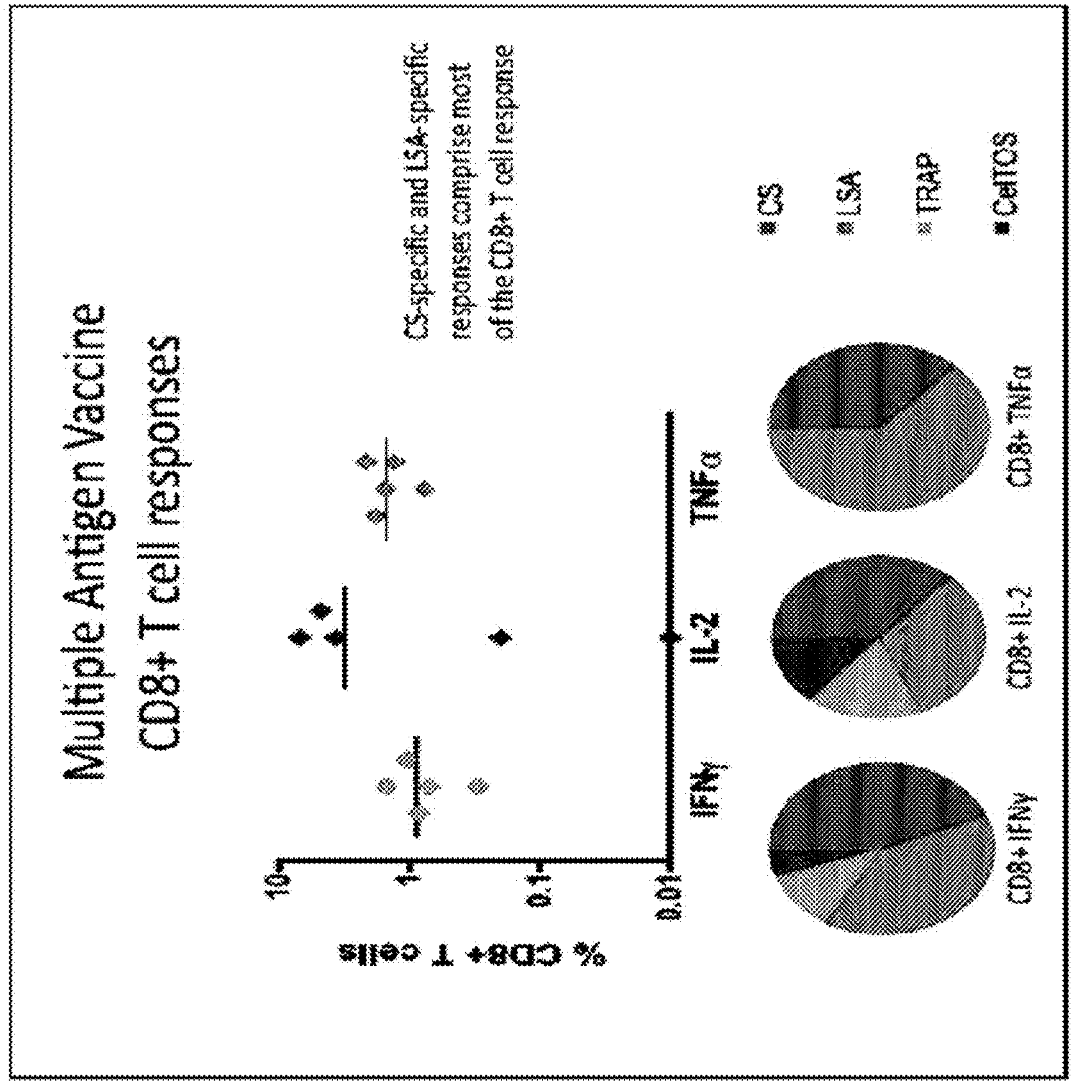
Figure 6G:
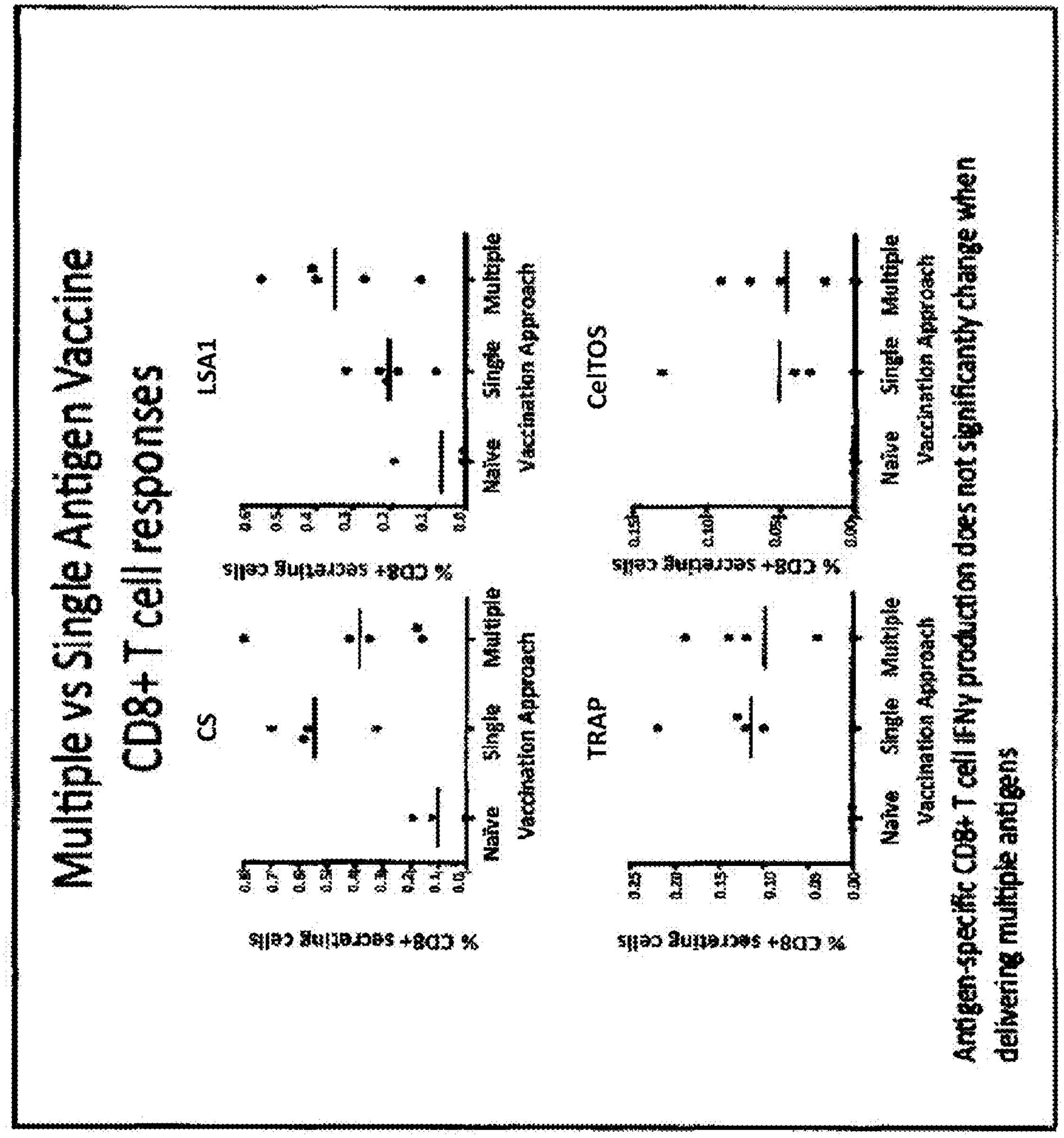
Figure 6H:
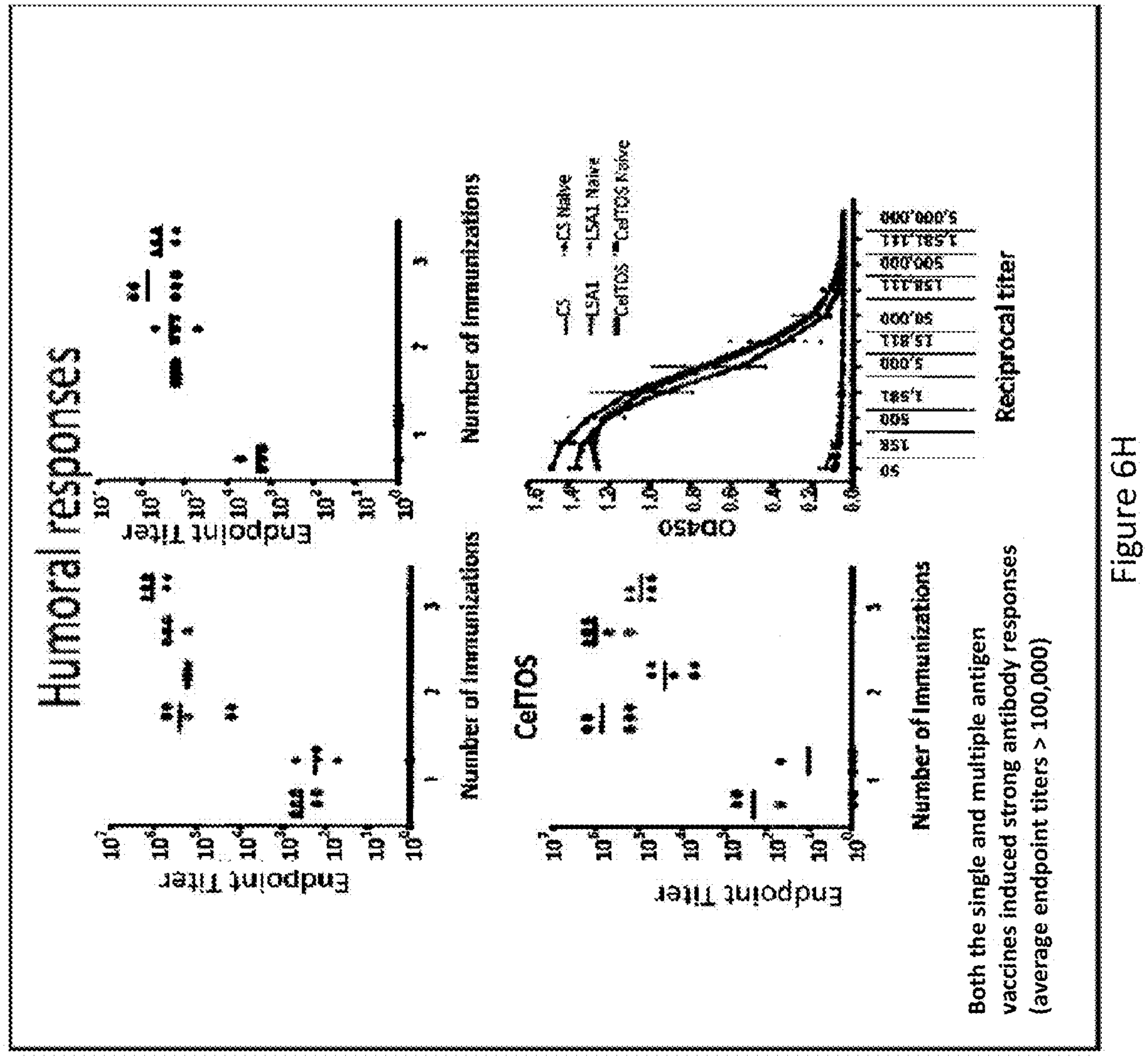
Figure 6I:
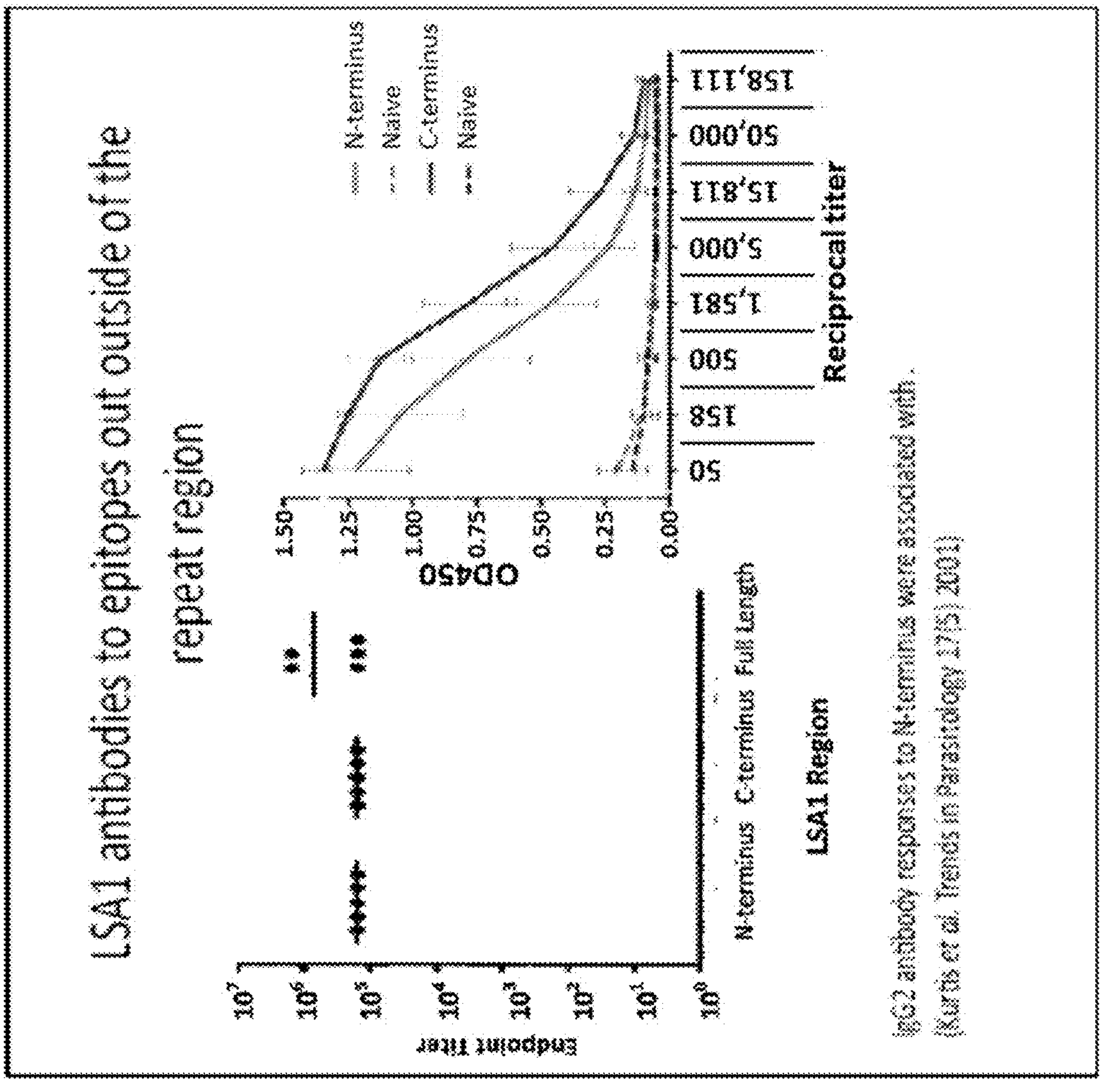

Cellular immunogenicity of the consensus antigens were determined by INF-γ ELISpot cellular immunogenicity analysis. Cellular immunogenicity of the individual consensus antigens is shown in FIG. 6A and the multiple antigen vaccine cocktail is shown in FIG. 6B. All vaccines induced a robust IFN-γ response as determined by ELISpot. The majority of CS- and LSA1-specific responses can be attributed to CD4+ and CD8+ dominant epitopes. Immunogenicity was compared with reported platforms including Ad35 or Ad35/protein boost, as results are shown in FIG. 6B. PfCon-LSA1 (right graph) induced stronger cellular responses to dominant CD4+ and CD8+ T cell epitopes than Ad35 or Ad35/protein heterologous prime boost approaches (left 3 graphs). Immunogenicity was compared with reported platforms including Ad5, Ad35 and RTS,S, as results are shown in FIG. 6C. PfconCS (right graph) induced antigen specific IFN gamma slightly lower than Ad5 (left pair of graphs), but stronger than Ad35 and RTS,S. Flow cytometry gating strategy was used and results were depicted in FIG. 6D. The multiple antigen vaccine was compared to decipher the details of the CD4+ T cell responses. The CD4+ T cell responses against the multiple antigen vaccine showed that CS-specific responses are the predominant CD4+ T cell response (FIG. 6E). The multiple antigen vaccine was compared to decipher the details of the CD8+ T cell responses. The CD8+ T cell responses against the multiple antigen vaccine showed that CS-specific and LSA-specific responses comprise most of the CD8+ T cell response (FIG. 6F). The CD8+ T cell responses were compared between a single antigen vaccine and a multiple antigen vaccine. The CD8+ T cell responses showed that there is no significant change when delivering multiple antigens (See FIG. 6G). Humoral responses were studied. Both the single and multiple antigen vaccines induced strong antibody responses (average endpoint titers >100,000) as shown in FIG. 6H. FIG. 6I displays graphs that show that the LSA1 antibodies are associated with epitopes outside of the repeat region. In one experiment, antibodies were shown to recognize cognate antigen in vivo. Each of the antigens were injected by hydrodynamic tail vein injection to allow for overexpression in the liver. Liver sections were then stained with sera from immunized mice (1:500) and all sections stained with the sera from each of the immunized mice (CS, LSA1, TRAP or CelTOS) showed antibody recognition of expressing cells (images not shown).

Example 4—Mouse Studies Using Multi-Antigen pDNA Vaccine Candidates Delivered Via In Vivo Electroporation Initial Studies Improved DNA vaccines for malaria through a multi-antigen vaccine approach are the subject of studies. A multi-antigen DNA vaccine candidate delivered by intramuscular injection and electroporation (EP), which targets the liver-stage of *Plasmodium falciparum* (P.f.) infection was assessed in initial mouse studies. This vaccine candidate incorporated four important liver-stage P.f. antigens: circumsporozoite protein (CS), liver stage antigen 1 (LSA1), thrombospondin-related-anonymous-protein (TRAP) and cell-traversal protein for ookinetes and sporozoites (CelTOS). The vaccine antigens were designed based on consensus sequences with several modifications to improve expression including codon and RNA optimization and the addition of a highly efficient IgE leader sequence.

Prior to immunogenicity studies in Balb/c mice, antigen expression was confirmed by in vitro translation, western blotting and immunohistochemistry. In mice, the vaccines elicited strong, antigen-specific cellular and humoral responses that were similar to, or surpassed, those induced by other vector systems. Specifically, interferon-gamma (IFNγ) spot forming cells per $10^6$ splenocytes (SFU) were quantified by ELISpot: CS (1607±391), LSA1 (1908±821), TRAP (929±255) and CelTOS (477±160). Further, the CS and LSA1 vaccines, delivered alone or in combination with TRAP and CelTOS, induced potent CS-specific and LSA-specific seroconversion (IgG endpoint titers of >150,000), determined by ELISA.

Additional Mouse Studies

Current evidence supports that a malaria vaccine candidate that elicits both strong humoral and cellular responses to multiple liver-stage antigens may be able to confer protection to P.f. Thus, the end goal of this vaccine approach is to induce cellular and humoral responses to CS, LSA1, TRAP and CelTOS simultaneously. Several studies were carried out in the mouse model to further optimize vaccine design and delivery and to further characterize vaccine-induced immune responses.

Other studies have suggested combined delivery of a PfCS DNA vaccine with additional DNA-based malaria antigens can decrease CS-specific T cell responses (Sedegah M, et al., Gene Therapy, 2004, 11(5):448-56)6). For this reason, antigen-specific responses induced by this multi-antigen vaccine candidate, in which the CS, LSA1, TRAP and CelTOS DNA vaccines were delivered in a single dose, were first compared to responses induced by the individual vaccines. For these studies, Balb/c mice received three immunizations spaced three weeks apart (Day 0, Week 3 and Week 6) and immune responses were evaluated one week after the last vaccination (Week 7). Vaccines were given i.m. followed by EP using the CELLETRA™ adaptive constant current device (Inovio Pharmaceuticals, Inc. Blue Bell, Pa.). The dose of each vaccine given was the same for the single and multi-antigen vaccine approaches. Blood was drawn on weeks 1, 3 and at the study endpoint for humoral analysis using ELISA. Cellular responses were determined by IFN-γ ELISpot and flow cytometry one week after the last immunization.

Optimization of Combined Delivery of Vaccine Antigens in the Mouse Model

To support future human clinical trials, studies were undertaken to further characterize the immunogenicity of the candidate antigens and develop multi-antigen formulations. In particular, two questioned were assessed: 1) whether the CS, LSA1, TRAP, and CelTOS antigens could be formulated together and 2) whether co-expression of multi-plasmid DNA antigens impacted the resulting immune potency of the formulation.

The two following approaches for developing a multi-component malaria vaccine were considered: (1) the physical combination of DNA plasmids expressing the four antigens individually followed by co-delivery of the multi-antigen formulation; and (2) cloning two or more antigens onto a single plasmid so that the antigens are translationally coupled and co-delivered by definition. Of the two approaches, option (1) was perceived to afford the greatest flexibility in terms of antigen combinations. The approach allowed the for interrogation of individual combinations for immune interference most easily, thus aiding in the selection antigen combinations for further development that are mutually compatible for expression and induction of cellular and humoral immune responses. This approach also allowed for experiments in which antigens could be "mixed and matched" depending on the clinical hypothesis tested (DNA EP alone vs. prime boost such as DNA-protein) as well as the desired immune responses (cellular vs. humoral) assessed. Data resulting from the pursuit of this strategy is included herein.

Option (2) was also considered viable and considered to have the benefit of reducing the number of plasmids required (because multiple antigens are combined in a single vector). However, a priori optimization might be time consuming because a number of independent factors affecting expression and immunogenicity of such a polycistronic construct. These include optimization of multiple promoters, relevant proteolytic cleavage sites, translation stop-restart sequences on the RNA level, and perhaps most critically, the ordering of the antigens relative to the promoter as well as the overall size of the construct. For large antigens (>1 kb DNA inserts), the need to optimize all of the above parameters in order to achieve optimal expression of each of the encoded antigens was possible in order to maximize the effectiveness of the vaccines. Consequently, while the latter approach is a viable alternative, it was not pursued in these experiments in order to provide the most efficient path toward establishing immunogenicity and efficacy data in humans. The final selection of the components and specific arrangements of antigens is more appropriately done later in the clinical development prior to undertaking large human clinical trials.

Antigen combinations were evaluated for possible interference in order to inform clinical trial design and support their further translation into the clinic.

Evaluation of Possible Antigen Competition-Humoral Immunogenicity

Figure 12:
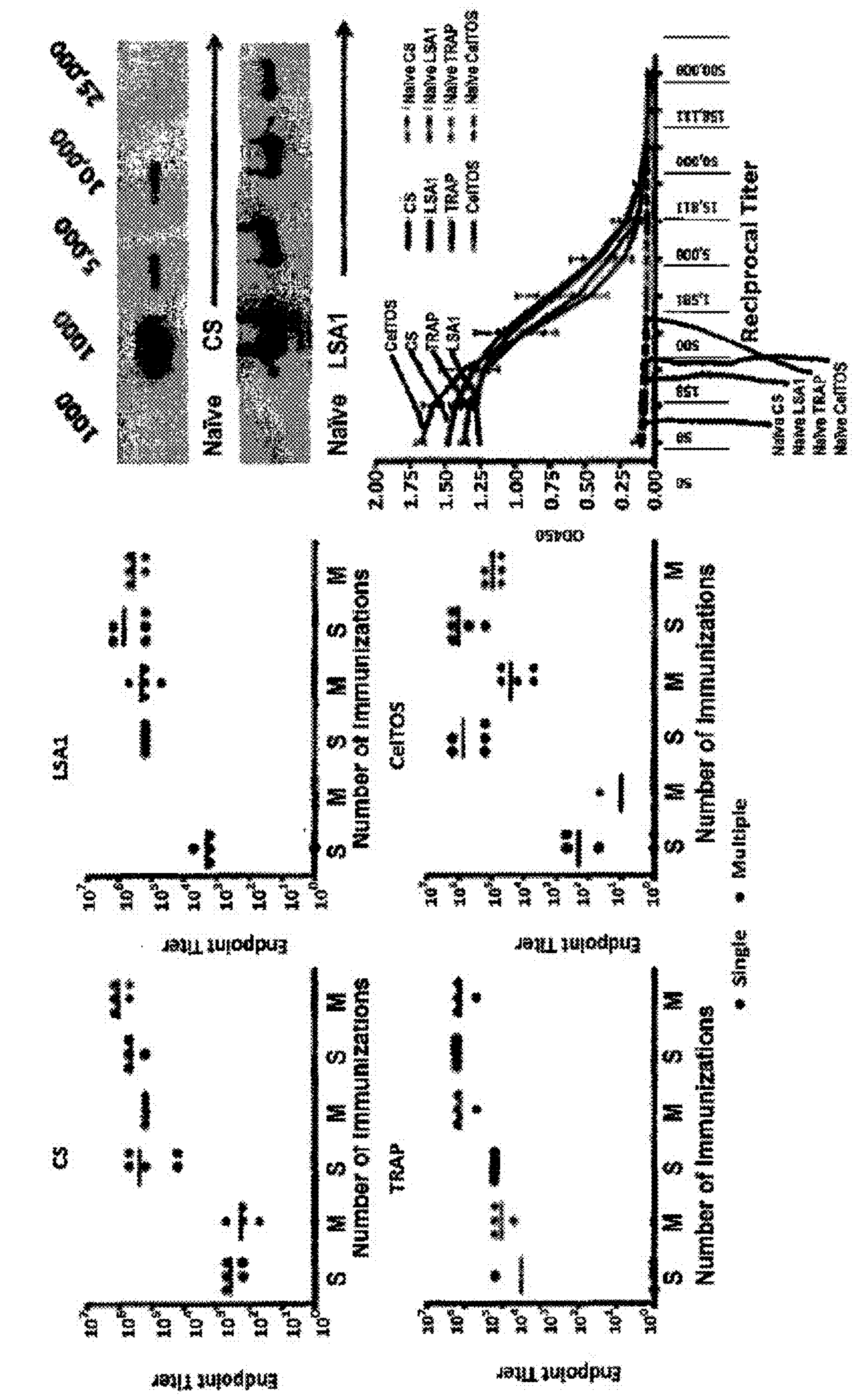

Single and multi-antigen vaccines induced high levels of CS- and LSA1-specific seroconversion. Completion of the production of recombinant proteins allowed for evaluation of humoral responses induced by the TRAP and CelTOS vaccines. Similar to CS and LSA1, both the single and multi-antigen vaccines induced high levels of TRAP- and CelTOS-specific seroconversion. For all antigens, there was a large boost in antibody titers with the second vaccination and, to a lesser extent, with the third vaccination (FIG. 12). Significantly, 100% of the vaccinated animals sero-converted after only 2 immunizations and endpoint titers for all antigens and both vaccine approaches were 100,000 after the third vaccination.

Evaluation of Possible Antigen Competition—Cellular Immunogenicity

Induction of antigen-specific CD4+ and CD8+ T cell secretion of IFNγ, IL-2 and TNFα by the single antigen and multi-antigen vaccines were first assessed by ICS. This data is briefly summarized below.

Figure 13:
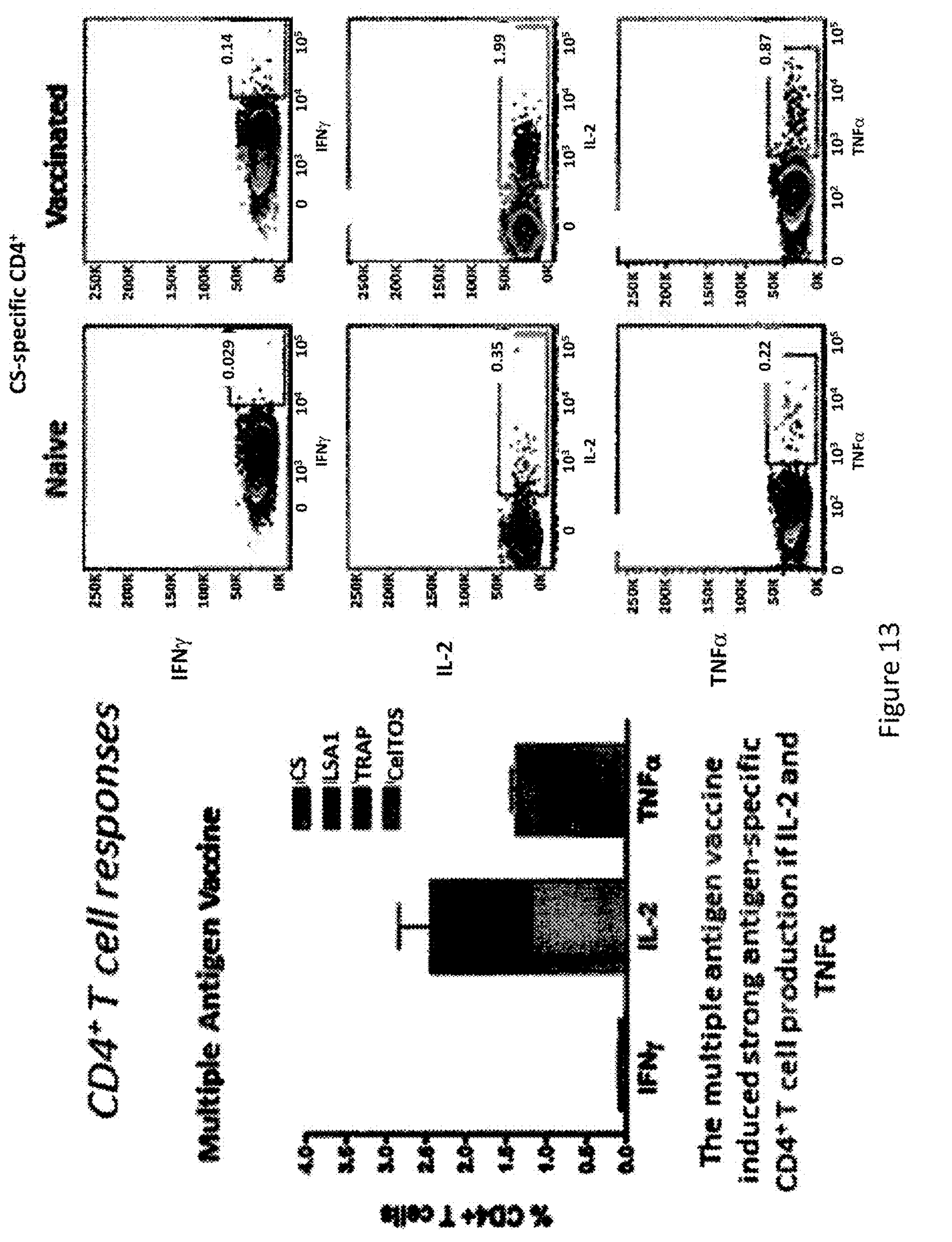

Overall, the multi-antigen vaccine induced strong CD4+ T cells responses. Specifically, 0.01% of CD4+ T cells produced antigen-specific IFNγ, 2.45% of CD4+ T cells produced antigen-specific IL-2 and of 1.39% CD4+ T cells produced antigen-specific TNFα (FIG. 13). The level of antigen-specific CD4+ T cell secretion of IFNγ induced by the multi-antigen vaccine was comparable to that of the single antigen vaccines. Relative to the CS and LSA1 vaccines, the multi-antigen vaccine induced more robust antigen-specific CD4+ T cell production of IL-2, and the increase in CS-specific IL-2 secretion approached statistical significance (p=0.06). The only statistically significant decreases in antigen-specific responses observed for the multi-antigen vaccine were lower levels of CD4+ T cell TNFα production in response to CelTOS (p=0.01) and TRAP (p=0.01). Despite these decreases in CelTOS- and TRAP-specific TNFα production, there was a trend toward increasing CS-specific CD4+ T cell TNFα secretion and no change in the LSA-specific CD4+ TNFα responses.

Figure 14:
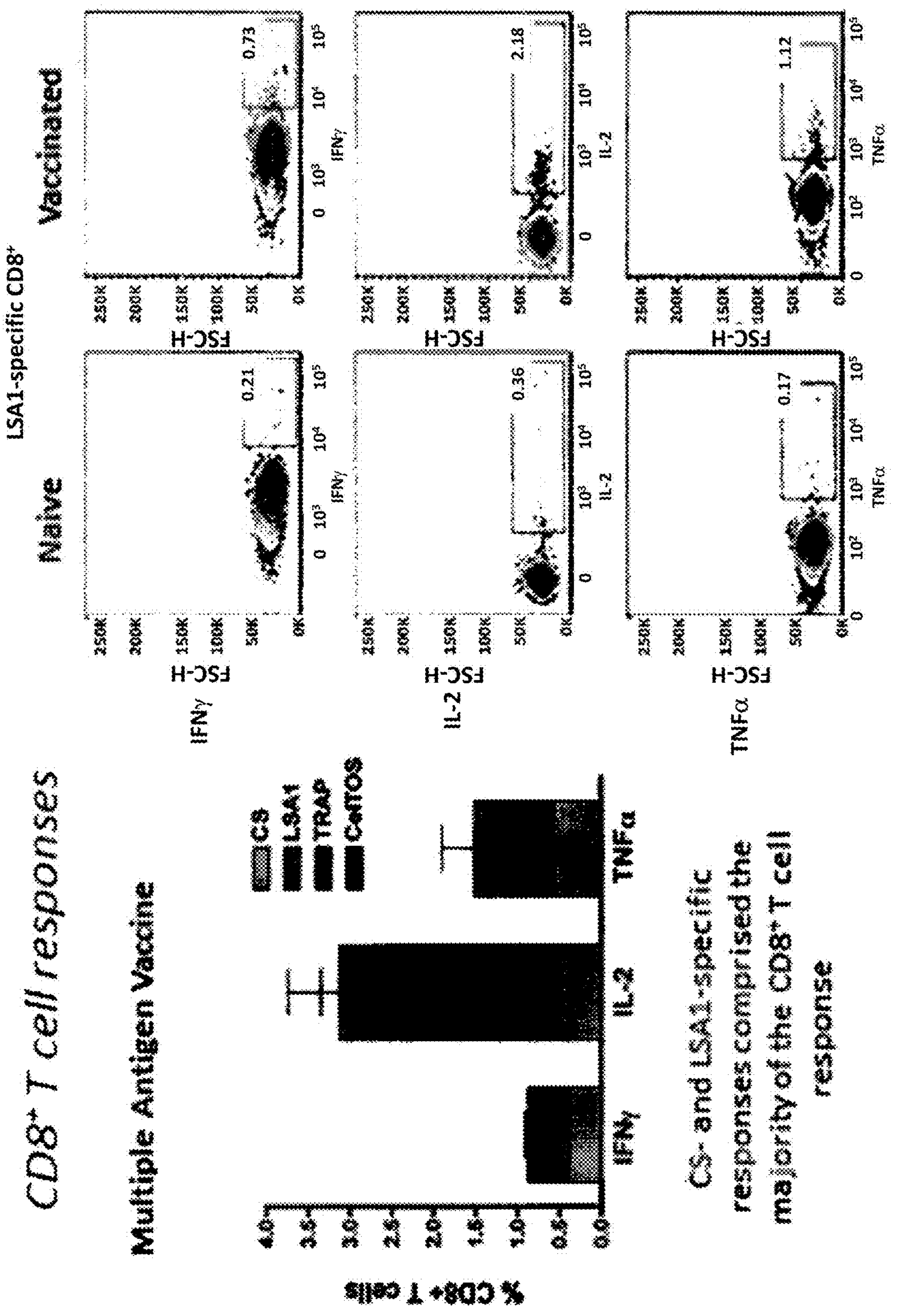

The multi-antigen vaccine also induced robust antigen-specific CD8+ T cell responses. Specifically, 0.9% of CD8+ T cells produced antigen-specific IFNγ, 3.1% of CD8+ T cells produced antigen-specific IL-2 and of 1.51% CD8+ T cells produced antigen-specific TNFα (FIG. 14). Similar to the CD4+ T cell IFNγ responses, there were minimal differences in the magnitude of antigen-specific CD8+ T cell secretion of IFNγ between the multi-antigen and single antigen vaccine approaches. Interestingly, the percentage of CS- and LSA1-specific IL-2 and TNFα producing CD8+ T cells was markedly increased with the multi-antigen vaccine.

Figure 15:
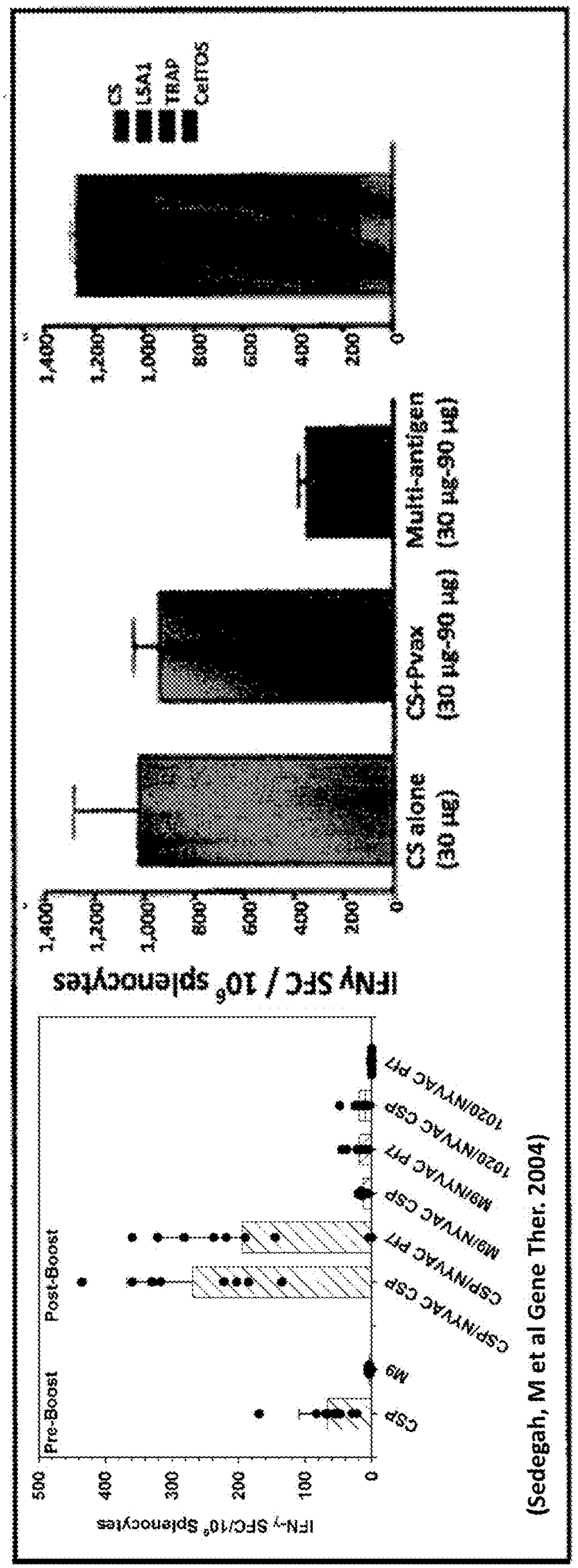

The presence of antigen competition, however, was more evident when the immunogenicity of the multi-antigen was evaluated by IFNγ ELISpot. Specifically, a 3.0-fold decrease in CS-specific IFNγ responses was observed when the CS vaccine was co-delivered with the LSA1, TRAP and CelTOS vaccines. The observed decrease in the magnitude of IFNγ production was not due to an increase in the total quantity of DNA being delivered (FIG. 15). It is believed that the apparently more pronounced decrease in CS-specific IFNγ responses observed using the ELISpot assay, compared to ICS, is most likely due to the greater sensitivity of the assay and not necessarily due to a significant decrease in the number of antigen-specific T-cells. Importantly, the decrease in CS-specific IFNγ production by ELISpot is representative of a decrease of only 0.005% of the total T cell population, which is similar to the decrease in the total population of CS-specific CD8+ T cell IFNγ production observed by ICS (0.004%).

Evaluation of Possible Antigen Competition—Summary

Taken together, the ICS and ELISA data suggest that in general, the antigens can be combined into a multi-antigen formulation without significant interference in the immune responses elicited.

Strategies to Increase CS-Specific Responses

Figure 16:
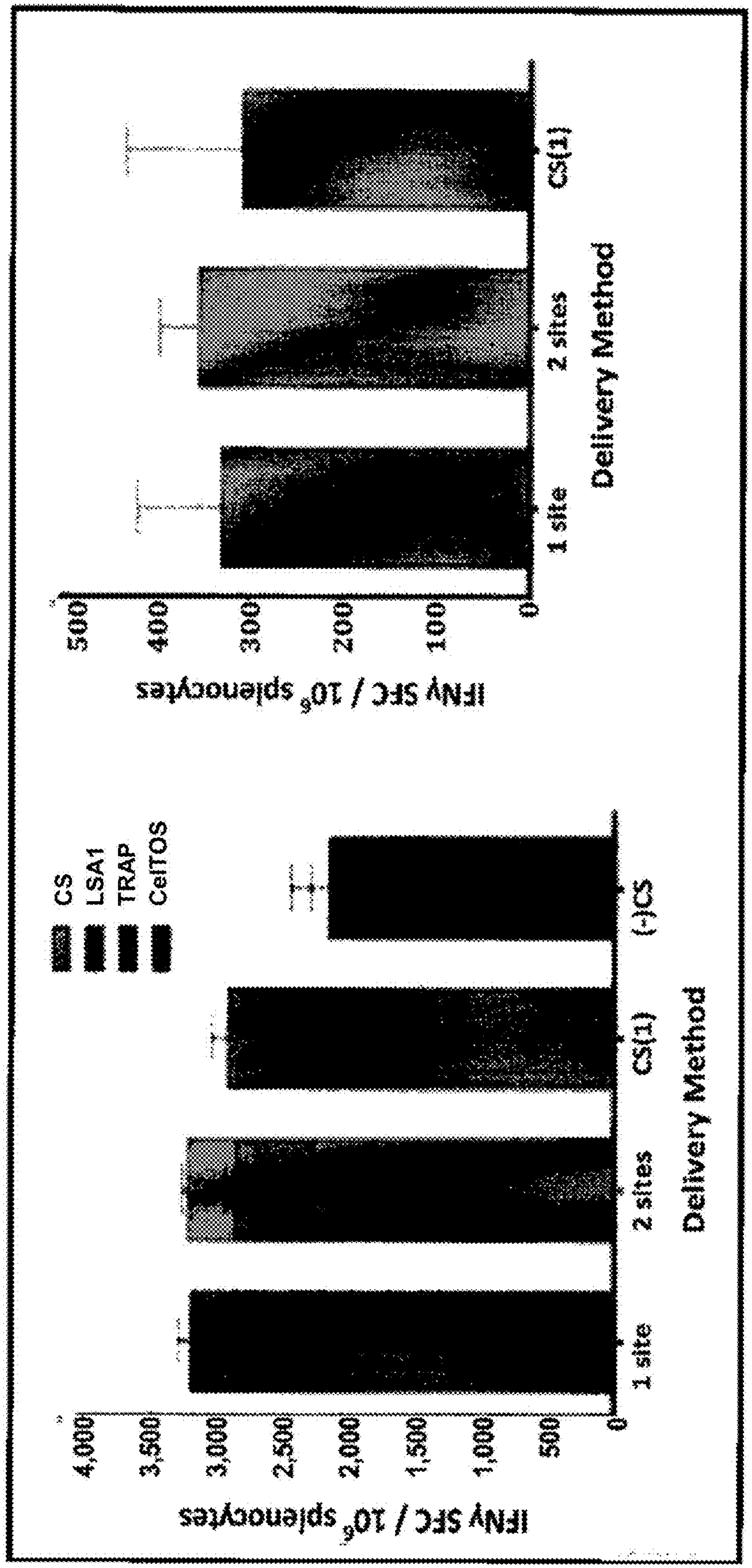

Nevertheless, because CS specific responses are considered important to have in a malaria vaccine, two vaccine delivery approaches were evaluated in an effort to increase the magnitude of the CS-specific component of the total multi-antigen vaccine IFNγ response. In the first approach, half of the total volume of the multi-antigen vaccine cocktail was delivered to one mouse hind limb and the other half was delivered into the contra-lateral mouse hind limb ("split leg" delivery). In the second approach, the CS vaccine was delivered into one mouse hind limb and a cocktail containing the LSA1, TRAP and CelTOS vaccines was delivered into the contra-lateral hind limb. These approaches did not significantly impact the magnitude of CS-specific IFNγ production (FIG. 16). These data indicate the decrease CS-specific in IFNγ responses observed with the multi-antigen vaccine is most likely due to an unknown systemic mechanism and is not directly related to co-delivery of all four antigens into the same site.

Pairing Comparisons

Next, pair-wise effects were evaluated to determine if one antigen could modulate the induction of antigen-specific IFNγ responses to other vaccine antigens. A matrix approach was used to evaluate all possible two-antigen combinations and antigen-specific IFNγ production was determined by IFNγ ELISpot. The fold change in IFNγ production, relative to the single-antigen vaccine response, for each antigen pair is reported in Table 1. Of note, both CS vaccine response and LSA1 vaccine response decreased when co-delivered with the CelTOS vaccine.

TABLE 1

The fold change in IFNγ production, relative to the single-antigen vaccine response, for each antigen pair.

| | | Antigen 2 | | | |
|---|---|---|---|---|---|
| Response | Antigen 1 | CS | LSA1 | TRAP | CelTOS |
| CS | CS | 1.0 | −1.4 | −1.1 | −2.8 |
| LSA | LSA1 | 1.2 | 1.0 | −1.3 | −2.9 |
| TRAP | TRAP | 1.4 | −1.2 | 1.0 | 1.0 |
| CelTOS | CelTOS | −1.5 | −1.1 | 3.0 | 1.0 |

While t these findings are preliminary and changes in immunogenicity for the antigen combinations failed to reach statistical significance, it is important to note that all antigens and all antigen pairs yielded robust T-cell responses as noted previously. Thus, despite noted differences, the interference was observed in the context of high levels of baseline immune responses and was in general, not inferior to the induction of strong T-cell responses relative to other vaccine approaches.

All the data taken together suggests that a combined, four-antigen formulation can be tested in a clinical setting and that antigenic competition observed, if any, is incidental, limited in scope, and may not be generalizable beyond the results of this study.

LSA1-Specific IFNγ Production by CD8+ Hepatic Lymphocytes

Figure 17:
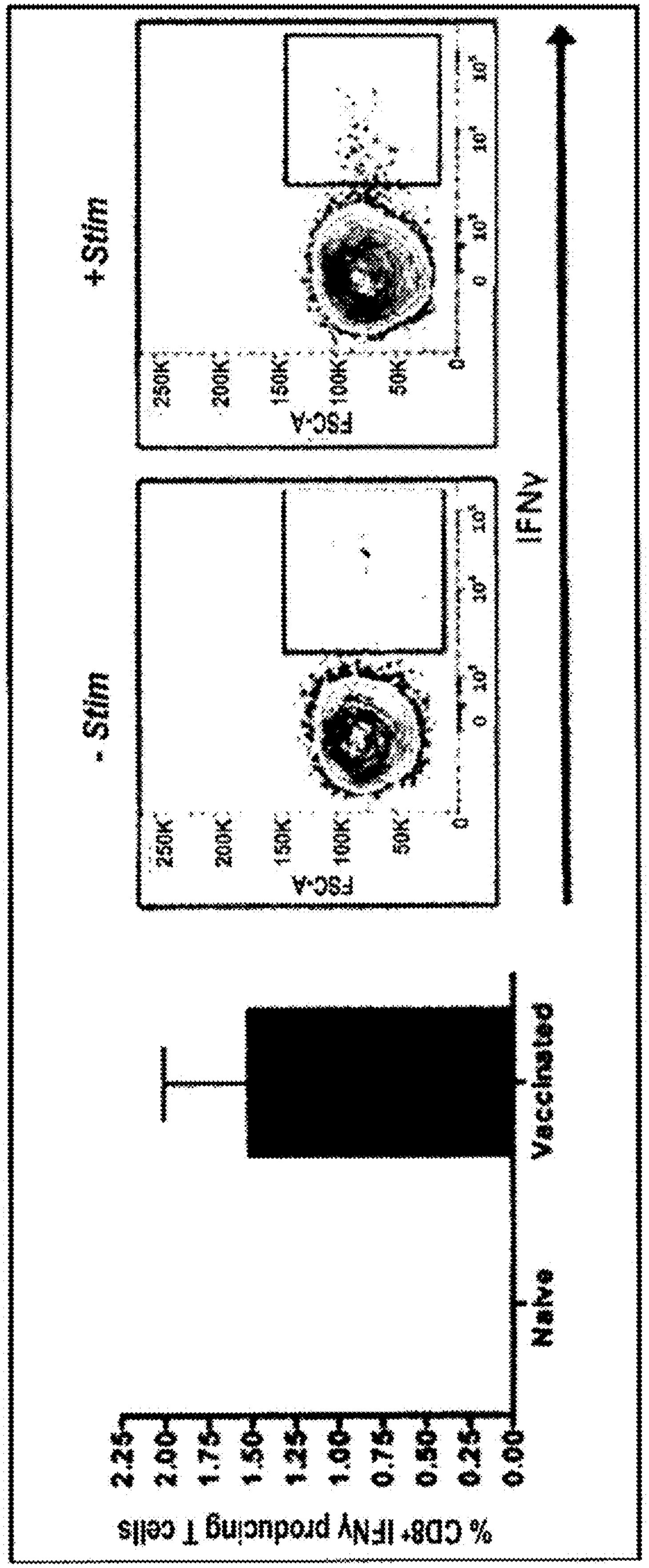

In rodent models, CD8+ T cells have been implicated as the principal effector cells, and IFNγ as the critical effector molecule in the elimination of sporozoite-infected hepatocytes. For this reason, this vaccine candidate was evaluated to determine if it could induce antigen-specific IFNγ production by CD8+ hepatic lymphocytes. Hepatic lymphocytes were isolated from multi-antigen vaccinated mice. The liver was thoroughly perfused prior to isolation of hepatic lymphocytes to reduce or eliminate the presences of circulating T cells in the isolated hepatic lymphocyte population. Induction of LSA1-specific CD8+ T cell IFNγ secretion was measured by ICS. An average of 1.5% of hepatic CD8+ T cells produced LSA1-specific IFNγ (n=8) and no background was observed in naïve mice (n=3) (FIG. 17)

These data show that a DNA-based vaccine such as the multi-antigen candidate tested can induce antigen-specific CD8+ T cells in the liver, i.e. at the site where they are required to clear sporozoite-infected hepatocytes, following intramuscular immunization.

Summary

Investigation of the effect of combining antigens (single vs. multiple antigen combinations) demonstrated that CS, TRAP, LSA-1, and CelTOS may be combined into a four-plasmid, combination malaria vaccine.

Example 5—Development of a DNA Vaccine Comprising Coding Sequence of Antigen AMA1

Figure 18:
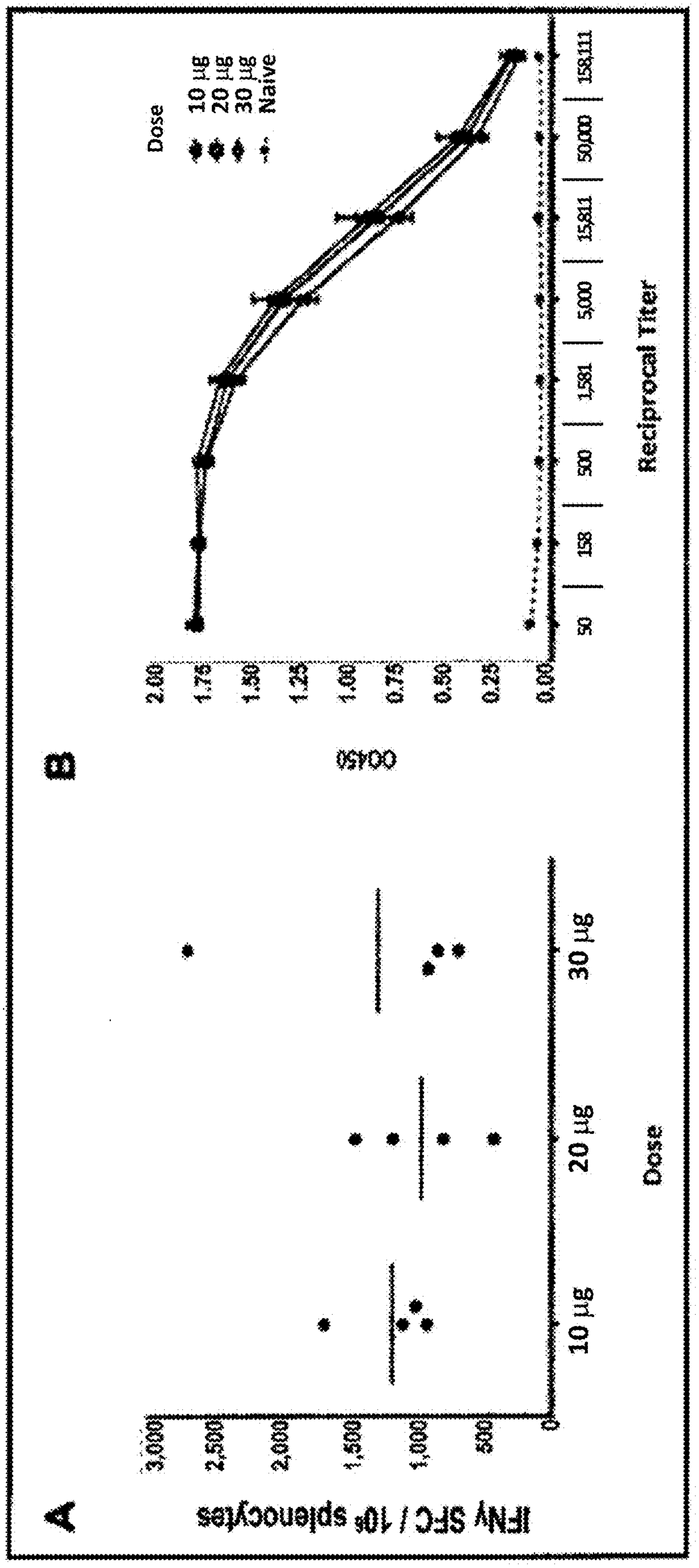

More recently, other groups have reported promising data for vaccine approaches that incorporate the AMA1 antigen. vaccine construct encoding the AMA1 protein from the Pf 3D7 strain has been designed and is disclosed herein. Cellular and humoral immunogenicity was evaluated in mice (n=4 per group) for 3 doses of the vaccine (10 μg, 20 μg and 30 μg) according to the standard vaccination schedule (see Above). The vaccine induced robust AMA1-specific T cell responses (FIG. 18A) and seroconversion (FIG. 18B). Both cellular and humoral immune responses did not increase significantly with dose. Vaccines comprising CS, LSA1, TRAP and CelTOS vaccine and further comprising the AMA1 vaccine have been designed and used.

Example 6—Non-Human Primate Studies Using Multi-Antigen pDNA Vaccine Candidates Delivered Via In Vivo Electroporation A study evaluating the quality and quantity of both cellular and humoral immune responses elicited by this multi-antigen malaria vaccine delivered by EP in the Indian rhesus macaque (macaca mulatta) NHP model is ongoing. In addition to testing the DNA vaccine alone, the effect of co-delivering IL-28B and incorporating a CS protein boost on vaccine-induced immune responses are being studied and functional assays are used in the evaluation the immunogenicity of this vaccine candidate and the impact of incorporation of an adjuvant and a heterologous prime-boost approach on cellular and humoral responses.

The NHP study was initiated. An additional group, serving as a control for another study (Group 5), was vaccinated earlier. These studies are currently in progress. The study groups and vaccination and bleed timeline are provided in Table 2 and Table 3, respectively.

TABLE 2

| Study Groups | | | | | |
|---|---|---|---|---|---|
| Group | Week 0 | Week 6 | Week 12 | Week 24 | DNA delivery |
| 1 | DNA | DNA | DNA | DNA | IM EP |
| 2 | DNA | DNA | DNA | Protein | IM EP |
| 3 | DNA | DNA | DNA | Protein | MID EP (3P) |
| 4 | DNA + IL-28 | DNA + IL-28 | DNA + IL-28 | Protein | IM EP |
| 5 | DNA + IL-28 | DNA + IL-28 | DNA + IL-28 | DNA + IL-28 | MID EP (3P) |
| 6 | Ctrl DNA | Ctrl DNA | Ctrl DNA | Ctrl DNA | IM EP |

DNA: 1.0 mg each: PfCS, PfLSA1, PfTRAP, PfCelTOS

DNA + IL-28:_ 1.0 mg each: PfCS, PfLSA1, PfTRAP, PfCelTOS and 0.5 mg macIL-28

Protein: Recombinant PfCS protein. 50 μg.

TABLE 3

| Vaccination and Bleed Timeline Week | | | | | | | | | | | | | | | | | |
|---|---|---|---|---|---|---|---|---|---|---|---|---|---|---|---|---|---|
| −2 | 0 | 2 | 4 | 6 | 8 | 10 | 12 | 14 | 16 | 18 | 20 | 22 | 25 | 27 | 29 | 32 | 33 |
| | V | | | V | | | V | | | | | | V | | | | |
| *B | B | B | | B | B | | B | B | | B | | | | B | | B | B |

B = blood draw,

V = vaccination

Summary of NHP Data Following the 2nd Immunization (Week 8)

Below are summaries of cellular and humoral immunogenicity data following through the 2nd vaccination of the on-going NHP study.

Cellular Immunogenicity

Figure 19:
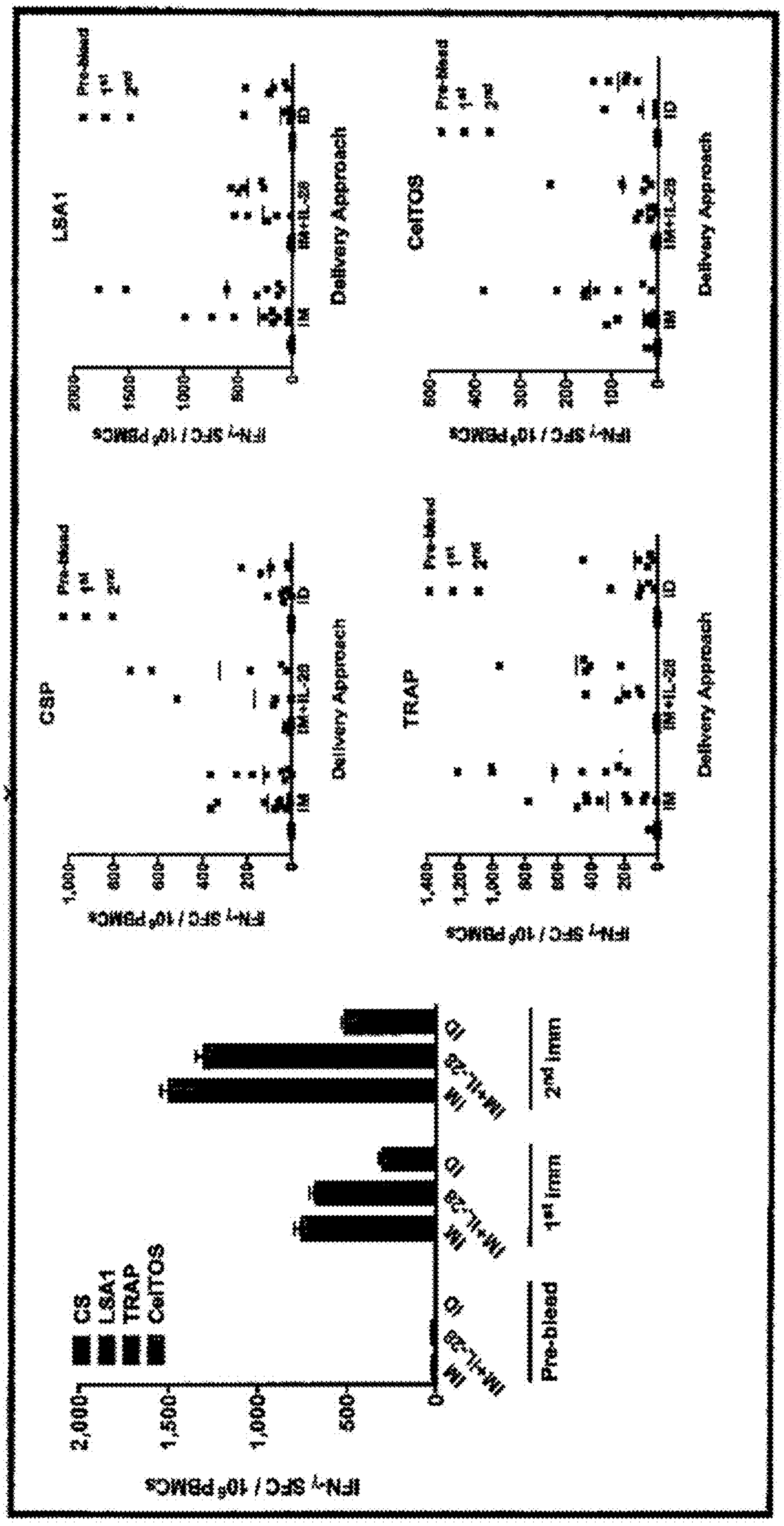

Overall, antigen-specific IFNγ responses boosted with the 2nd immunization for all 4 antigens and delivery approaches (FIG. 19, left panel). Following the 2nd immunization, the mean antigen-specific IFN (responses by IFN (ELISpot was slightly greater in the IM groups (n=10) (1350(1116 SFU, range 318-3842 SFU), compared to IM delivery with IL-28B (n=5) (1310(309 SFU, range 986-1540 SFU) and ID delivery (n=5) (402(288 SFU, range 132-760 SFU). Interestingly, c Co-delivery of IL-28B specifically increased the magnitude of the CSP-specific response (FIG. 19, right panel) and decreased the variability of the responses.

Figure 20:
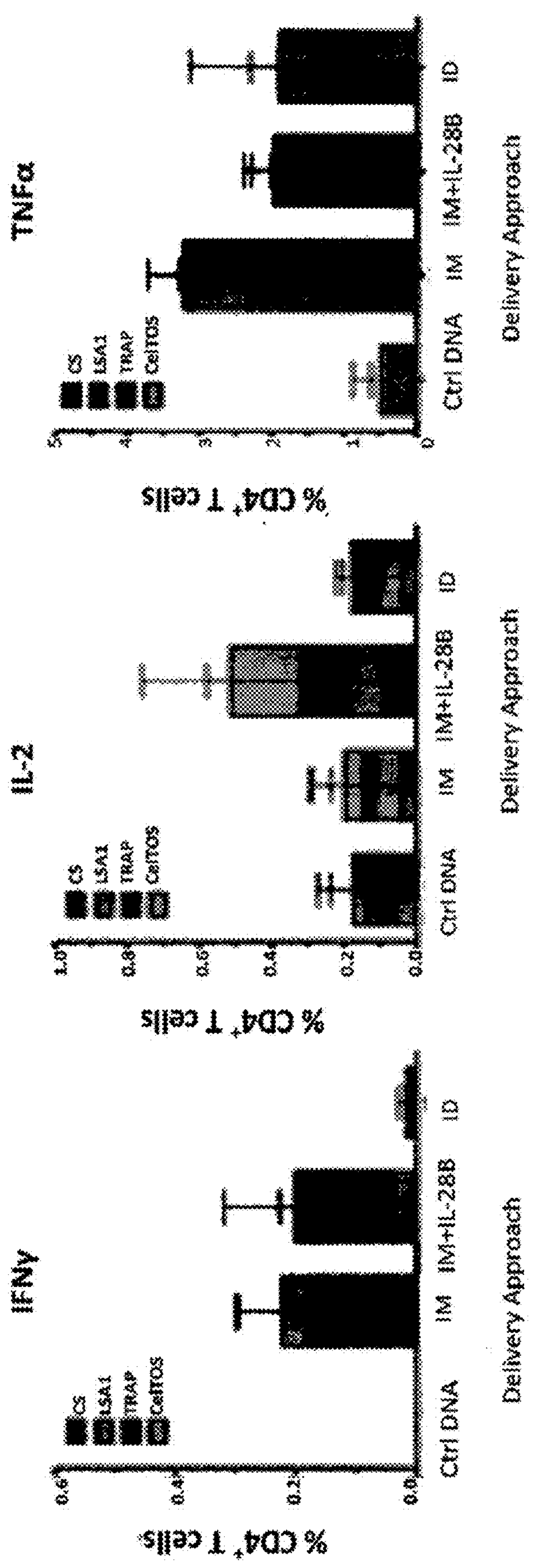
Figure 21:
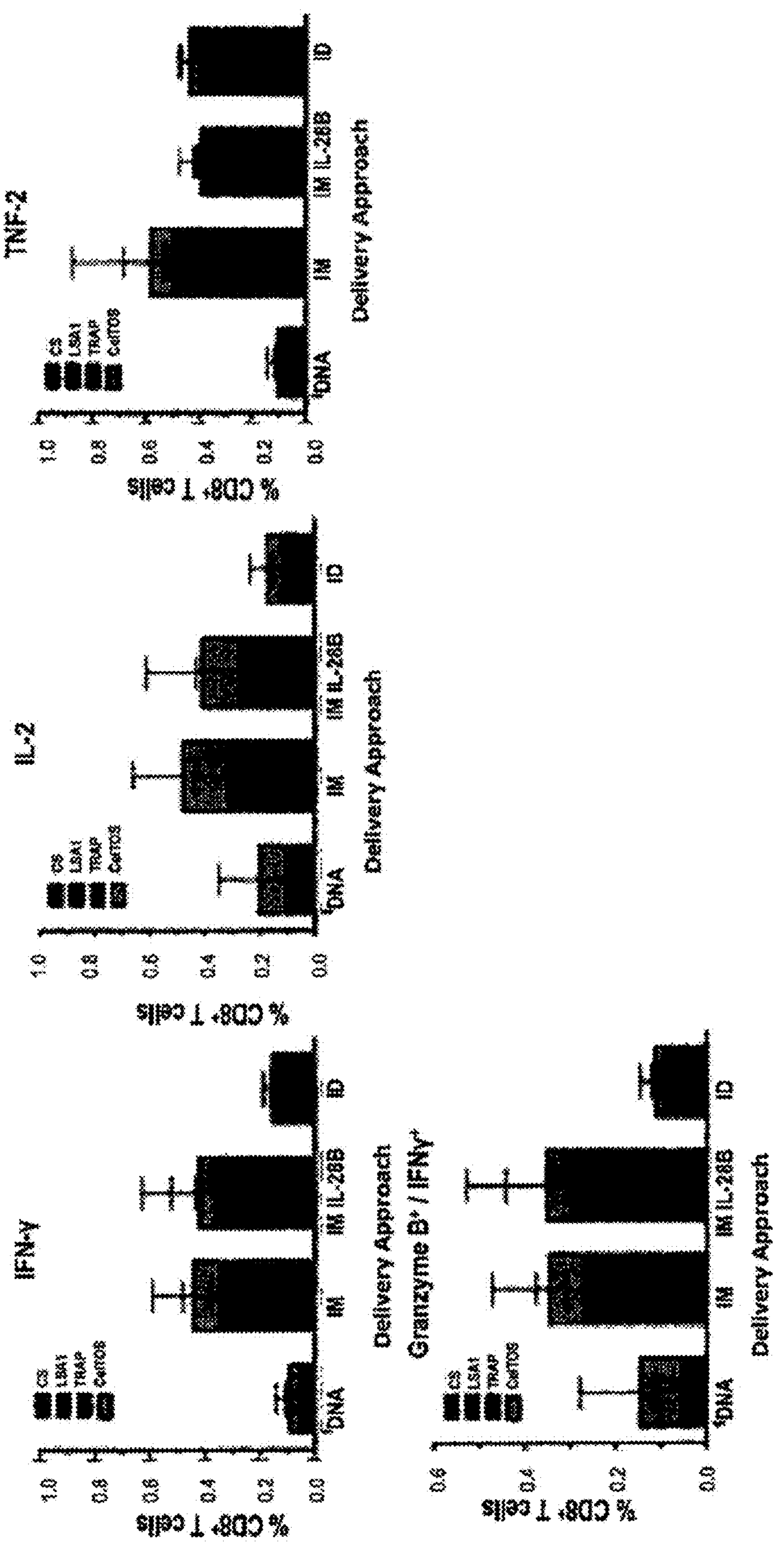

Cellular immunogenicity was also evaluated by flow cytometry and antigen-specific responses following the 2nd immunization (week 8) are reported in FIGS. 20 and 21. CD4+ T cell production of IFNγ was similar for the IM (0.22%) and IM+IL-28 (0.20%) delivery approaches. Minimal levels of antigen-specific CD4+ T cell secretion of IFNγ were observed for ID delivery (FIG. 20, left panel). Co-delivery with IL-28B increased antigen-specific CD4+ T cell production of IL-2 (0.49%) compared to IM delivery of the vaccine alone (0.20%) (FIG. 20, center panel). There was a robust CSP- and LSA1-specific response TNFα response in the CD4+ T cell compartment in all groups. Antigen-specific TNFα was highest in the IM group (3.2%) compared to IM+IL-28B (2.0%) and ID (1.9%) (FIG. 20, right panel).

IFNγ T cell reposes in the CD8+ T cell compartment follow a similar trend to the IFNγ ELISpot and the responses in the CD4+ T cell compartment. Overall, antigen-specific CD8+ T cell responses were more robust for IM delivery (with or without IL-28B) compared to ID delivery. Antigen-specific IFNγ production was greatest in the IM (0.44%) and IM+IL-28B (0.42%) groups compared to the ID group (0.15%) (FIG. 21, left panel). CSP-specific IFNγ production was higher with co-delivery of IL-28B (0.28%) compared to IM delivery of the vaccine without adjuvant (0.11%). The majority of CD8+IFNγ+ T cells were also granzyme B+ (FIG. 21, lower left panel): 1M, 0.35%; IM+IL-28B, 0.35%; ID, 0.11%). Antigen-specific CD8+ T cell production of IL-2 was more robust in the IM (0.48%) and IM+IL-28B (0.41%) groups compared to ID (0.24%) (FIG. 21, center panel). Similar to the CD4+ T cell compartment, there was a robust, albeit of lower magnitude, TNFα response in the CD8+ T cell compartment that was predominantly in response to the CSP and LSA1 antigens. Specifically, 0.58% 0.40% and 0.43% of CD8+ T cells produced TNFα in the IM, IM+IL-28 and ID groups, respectively.

Humoral Immunogenicity

High-levels of antigen-specific sero-conversion for all antigens were observed following after a single immunization that, overall, boosted with the 2nd immunization (FIG. 22). IgG antibody titers for all antigens was determined by ELISA and endpoint titers were calculated as described by Frey, A. et al. (J Immunol. Methods 1998; 221:35-41). Briefly, the endpoint titer is reported as the reciprocal of the last dilution that remained above the upper predication limit of a 95% confidence interval calculated from the mean of the naïve antibody titers. CSP and LSA1-specific seroconversion increased in all groups following the 2nd immunization. The mean TRAP and CelTOS endpoint titers increased for IM and ID delivery with the 2nd immunization, but the mean titers did not increase for the IM+IL-28B group. Although the TRAP- and CelTOS-specific levels of IgG did not increase overall with IL-28B, the consistency of the responses did increase.

Summary

The investigation of the immunogenicity of the vaccine antigens in non-human primates has demonstrated that the four antigen combination produces strong T-cell and humoral immune responses in NHP after only two vaccinations. The NHP data herein confirm the immunogenicity of the pDNA constructs targeting CS, LSA1, TRAP, and CelTOS in the primate model and support the previous data in the mouse model. As noted above, the pDNA antigens delivered by in vivo EP yield strong cellular and humoral responses. Relative immune responses resulting from differences in route of delivery (ID v IM) and the use of IL-28B cytokine were tested and showed ID delivery of the vaccine formulation leads to strong humoral immune responses. The impact of a further protein boost on the magnitude and quality of immune responses will be assessed.

Example 7—IL-28B Enhances Vaccine-Specific Cellular and Humoral Responses and Reduces Regulatory T Cell Populations The effect of delivering a DNA vector encoding the cytokine gene adjuvant, IL-28 combined with delivery of the DNA vaccine was evaluated to determine if it increased the antigen-specific effector and memory T-Cell responses specific for the vaccine antigens. Current evidence suggests a malaria vaccine that induces a high-level of memory T cells may provide long-term protection. Delivery of a DNA vector encoding the IL-28B cytokine gene adjuvant (Morrow et al., Blood, 2009 113(23):5868-77) in conjunction with other DNA vaccines increased the overall immunogenicity and level of memory T cells while decreasing the level of regulatory T cells. IL-28B was demonstrated to drive the induction of antigen specific CD8+ T cells that exhibit phenotypes that are characteristic of CTLs.

Figure 23:
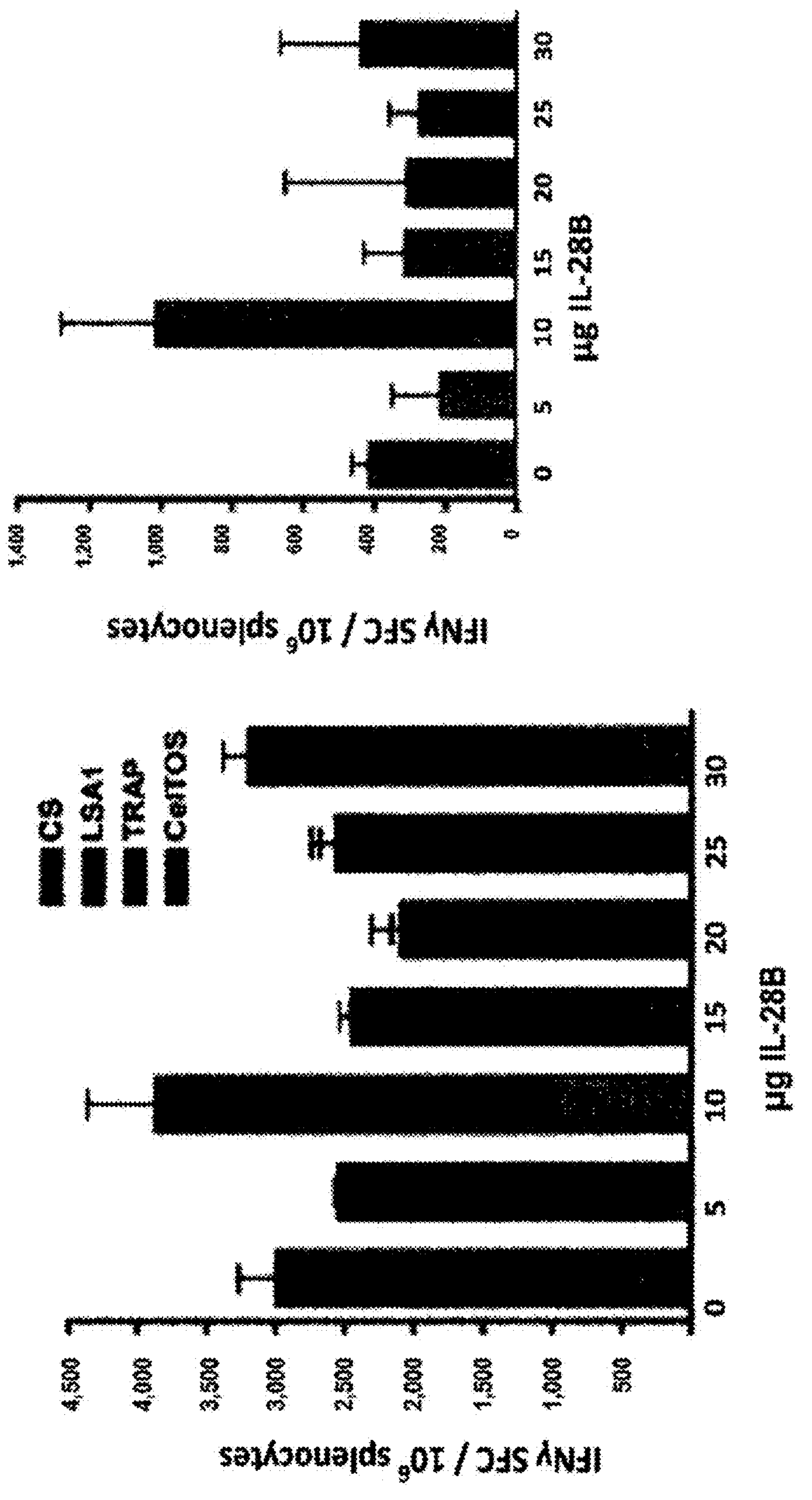
Figure 24:
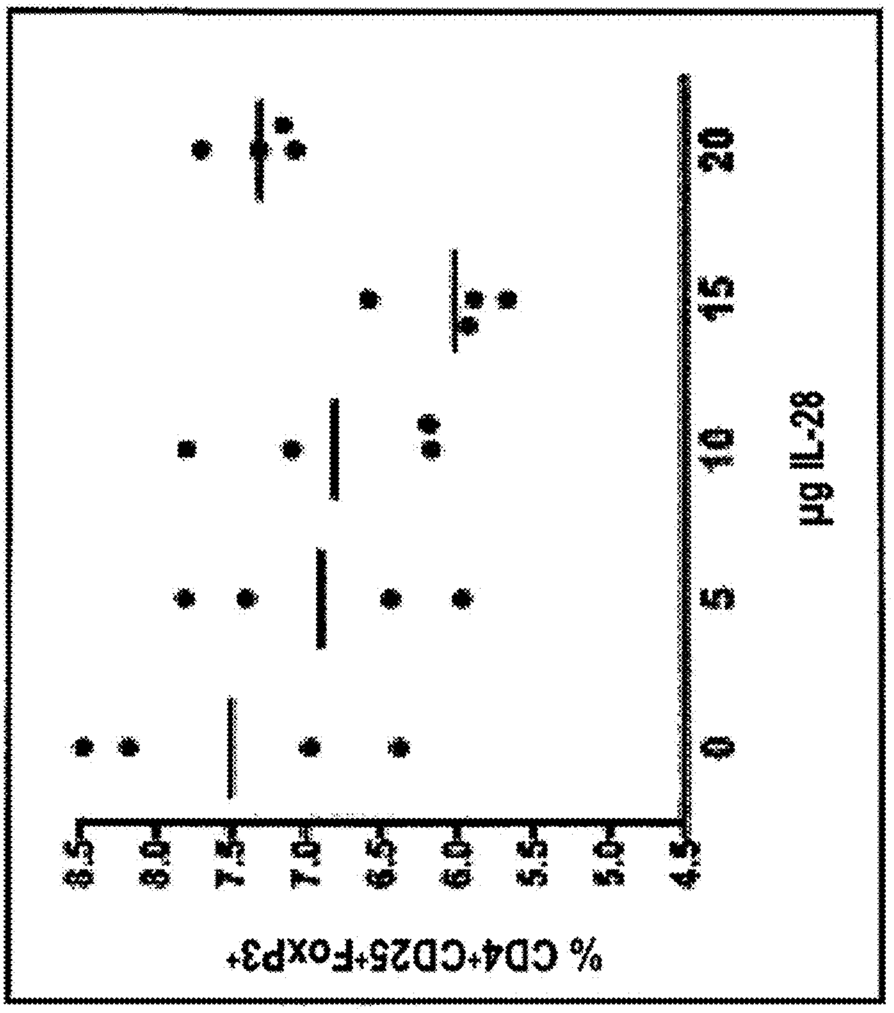
Figure 25:
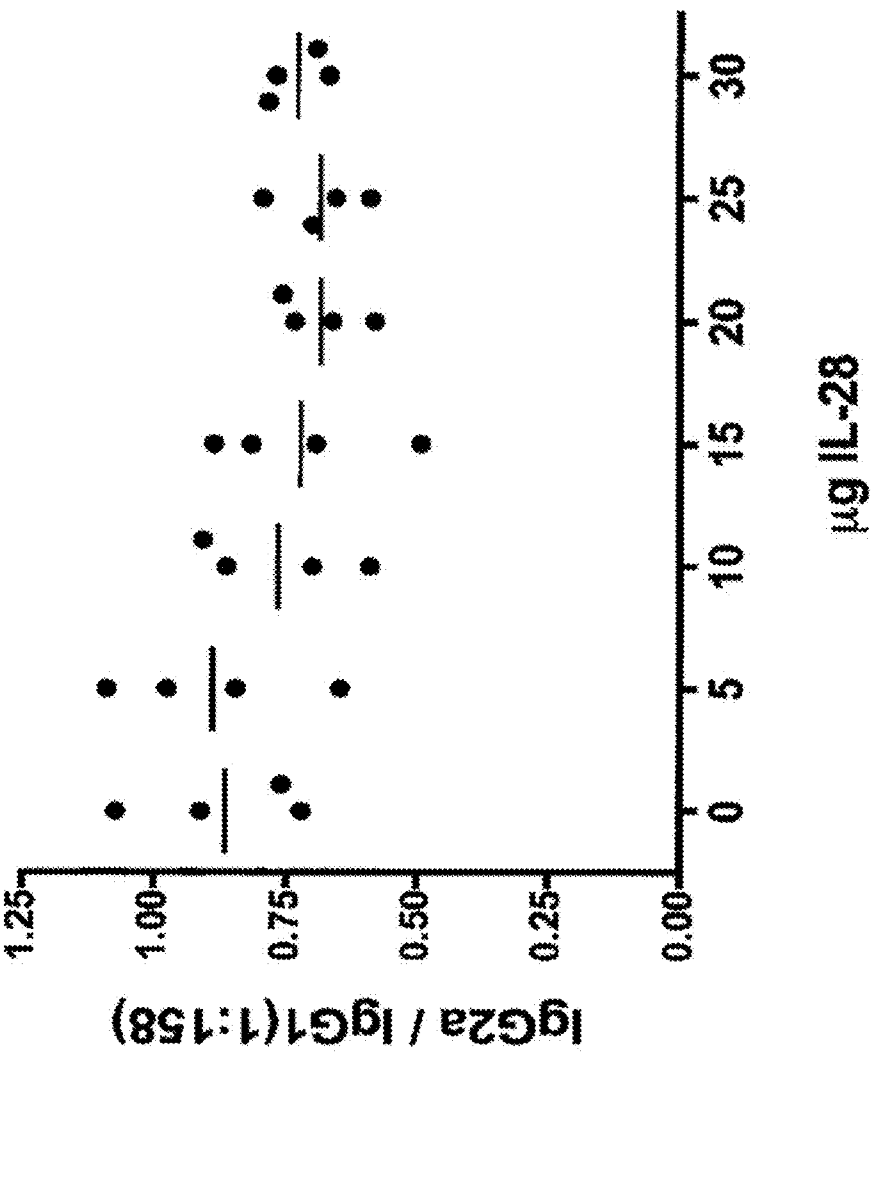
Figure 25:
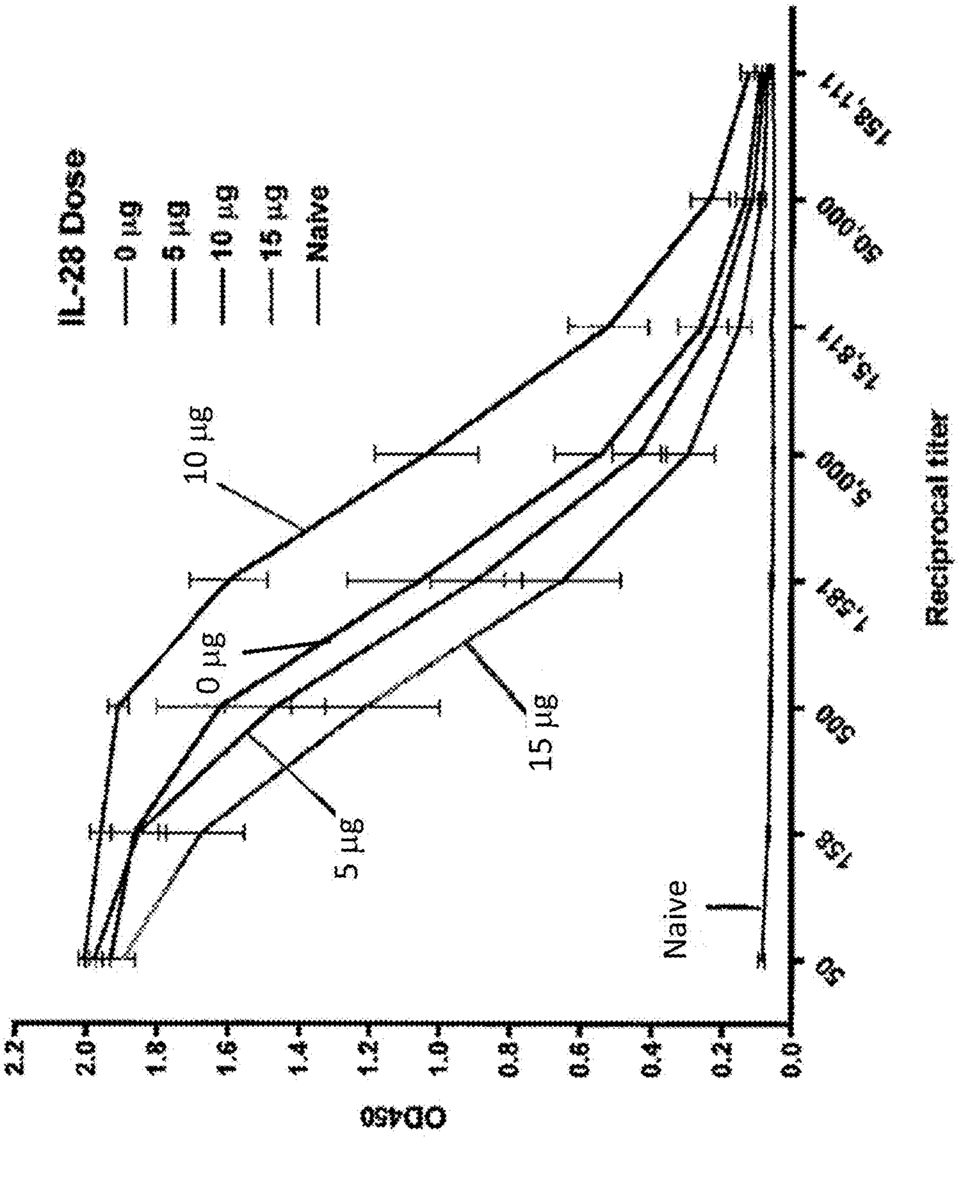
Figure 25:
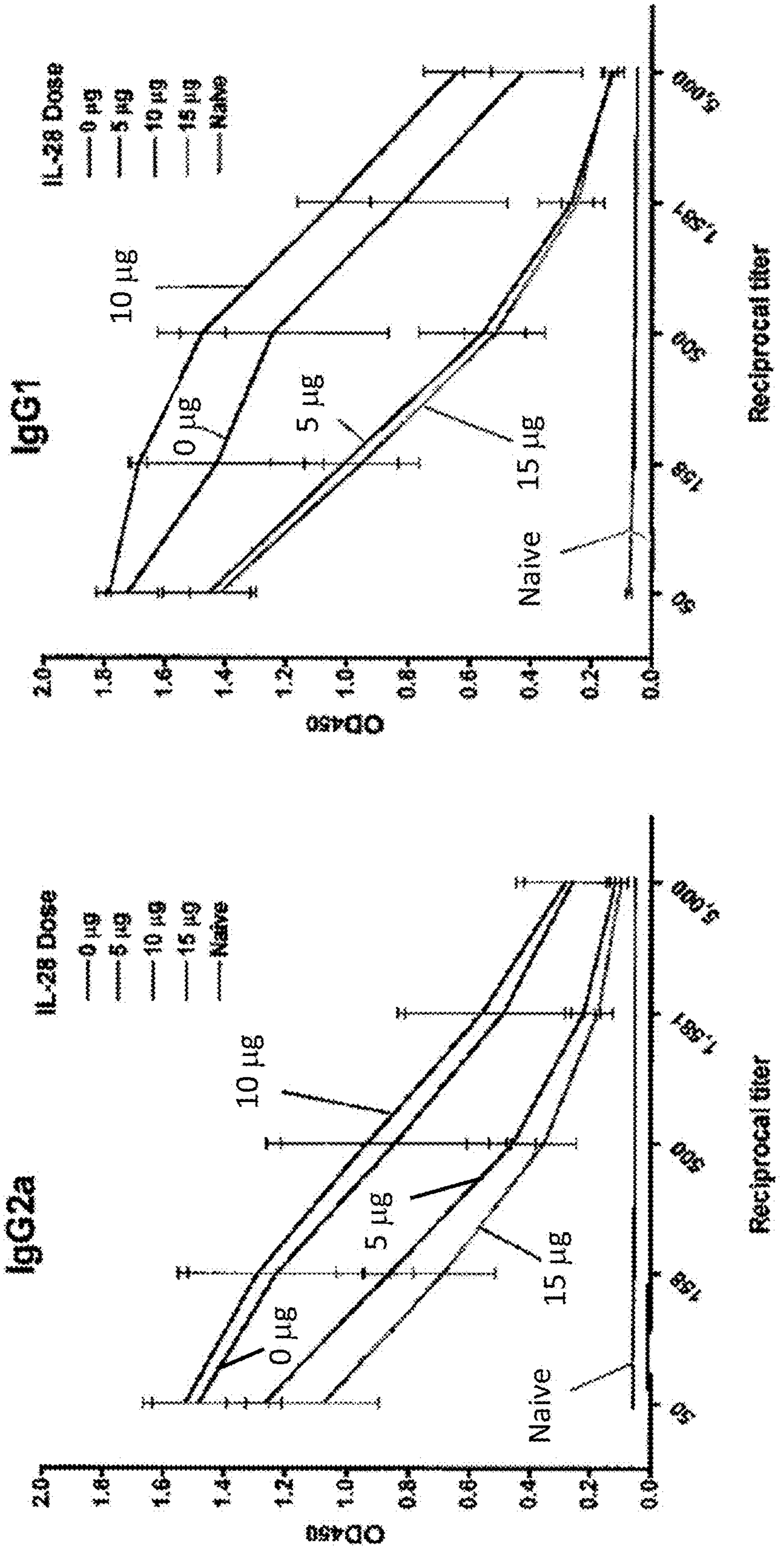

The ability of IL-28B to enhance antigen-specific responses to this vaccine in the mouse model was explored. Co-delivery of 10 μg of IL-28B with the multi-antigen vaccine increased the total vaccine-specific IFNγ response 1.5-fold. IL-28B increased CS-specific and CelTOS-specific IFNγ production 2.5-fold and 2.0-fold, respectively (FIG. 23). A decrease in the population of CD4+CD25+FoxP3+ regulatory T cells followed a similar trend as the increase in the vaccine-specific IFNγ response (FIG. 24). IL-28B has been previously reported to have specifically augmented cellular immunogenicity, but did not affect humoral responses to two different vaccines. When co-delivered with this vaccine, IL-28B also increased CS-specific seroconversion (FIG. 25).

Investigation of the effects of cytokine adjuvant IL-28B in modulating and/or improving the immune potency of the candidate vaccine showed that co-delivery of IL-28B increased vaccine specific IFN-γ production, decreased the number of Tregs, and increased the CS-specific sero-conversion.

Example 8—DNA/Protein Prime-Boost Approach

CS protein is an important antigen and its ability to drive humoral responses may be associated with protection. In addition to testing CS protein boost in the NHP study, the immunogenicity and potential toxicity of the CS protein by itself was tested in mice.

The invention claimed is:

1. An immunogenic composition comprising a nucleic acid molecule that encodes at least one *Plasmodium falciparum* (*P. falciparum*) immunogen, wherein the immunogenic composition comprises a nucleic acid sequence encoding *P. falciparum* immunogen TRAP; wherein the nucleic acid sequence encoding *P. falciparum* immunogen TRAP comprises SEQ ID NO:5.

2. The immunogenic composition of claim 1 further comprising at least one nucleotide sequence encoding at least one additional *P. falciparum* immunogen selected from the group consisting of:

a) a nucleotide sequence encoding *P. falciparum* immunogen circumsporozoite protein (CS), wherein the nucleotide sequence comprises a sequence selected from the group consisting of SEQ ID NO:1 and SEQ ID NO:11;

b) a nucleotide sequence encoding *P. falciparum* immunogen liver stage antigen 1 (LSA1), wherein the nucleotide sequence comprises SEQ ID NO:3;

c) a nucleotide sequence encoding *P. falciparum* immunogen cell-traversal protein for *Plasmodium* ookinetes and sporozoites (CelTOS), wherein the nucleotide sequence comprises SEQ ID NO:7; and d) a nucleotide sequence encoding *P. falciparum* immunogen Apical membrane antigen 1 (Ama1), wherein the nucleotide sequence comprises SEQ ID NO:9.

3. The immunogenic composition of claim 1 further comprising a nucleotide sequence that encodes IL-12, IL-15, IL-28B or RANTES.

4. The immunogenic composition of claim 1 wherein said nucleic acid molecule is incorporated into a plasmid.

5. The immunogenic composition of claim 4 further comprising at least one additional plasmid comprising at least one nucleotide sequence encoding at least one additional *P. falciparum* immunogen selected from the group consisting of:

a) a nucleotide sequence encoding *P. falciparum* immunogen CS), wherein the nucleotide sequence comprises a sequence selected from the group consisting of SEQ ID NO:1 and SEQ ID NO:11;

b) a nucleotide sequence encoding *P. falciparum* immunogen LSA1, wherein the nucleotide sequence comprises SEQ ID NO:3;

c) a nucleotide sequence encoding *P. falciparum* immunogen CelTOS, wherein the nucleotide sequence comprises SEQ ID NO:7; and d) a nucleotide sequence encoding *P. falciparum* immunogen wherein the nucleotide sequence comprises SEQ ID NO:9.

6. The immunogenic composition of claim 4 further comprising a nucleotide sequence that encodes IL-12, IL-15, IL-28B or RANTES.

7. The immunogenic composition of claim 4 further comprising one or more plasmids that collectively comprise one or more of a) a nucleotide sequence encoding *P. falciparum* immunogen CSC wherein the nucleotide sequence comprises a sequence selected from the group consisting of SEP ID NO: 1 and SEP ID NO: 11:

b) a nucleotide sequence encoding *P. falciparum* immunogen LSA1, wherein the nucleotide sequence comprises SEP ID NO:3;

c) a nucleotide sequence encoding *P. falciparum* immunogen CelTOS, wherein the nucleotide sequence comprises SEP ID NO:7; and d) a nucleotide sequence encoding *P. falciparum* immunogen Ama1, wherein the nucleotide sequence comprises SEP ID NO:9.

8. The immunogenic of claim 4 further comprising one or more plasmids that collectively comprise two or more of a) a nucleotide sequence encoding *P. falciparum* immunogen CSC wherein the nucleotide sequence comprises a sequence selected from the group consisting of SEP ID NO: 1 and SEP ID NO: 11;

b) a nucleotide sequence encoding *P. falciparum* immunogen ISA 1, wherein the nucleotide sequence comprises SEP ID NO:3;

c) a nucleotide sequence encoding *P. falciparum* immunogen CelTOS, wherein the nucleotide sequence comprises SEP ID NO:7; and d) a nucleotide sequence encoding *P. falciparum* immunogen Ama1, wherein the nucleotide sequence comprises SEP ID NO:9.

9. The immunogenic composition of claim 4 further comprising one or more plasmids that collectively comprise three of a) a nucleotide sequence encoding *P. falciparum* immunogen CSC wherein the nucleotide sequence comprises a sequence selected from the group consisting of SEP ID NO: 1 and SEP ID NO: 11:

b) a nucleotide sequence encoding *P. falciparum* immunogen ISA 1, wherein the nucleotide sequence comprises SEP ID NO:3;

c) a nucleotide sequence encoding *P. falciparum* immunogen CelTOS, wherein the nucleotide sequence comprises SEP ID NO:7; and d) a nucleotide sequence encoding *P. falciparum* immunogen Ama1, wherein the nucleotide sequence comprises SEP ID NO:9.

10. The immunogenic composition of claim 4 further comprising one or more plasmids that collectively comprise a) a nucleotide sequence encoding *P. falciparum* immunogen CSC wherein the nucleotide sequence comprises a sequence selected from the group consisting of SEP ID NO: 1 and SEP ID NO: 11:

b) a nucleotide sequence encoding *P. falciparum* immunogen LSA1, wherein the nucleotide sequence comprises SEP ID NO:3; and c) a nucleotide sequence encoding *P. falciparum* immunogen CelTOS, wherein the nucleotide sequence comprises SEP ID NO:7.

11. The immunogenic composition of claim 4 further comprising one or more plasmids that collectively comprise a) a nucleotide sequence encoding *P. falciparum* immunogen CSC wherein the nucleotide sequence comprises a sequence selected from the group consisting of SEP ID NO: 1 and SEP ID NO: 11:

b) a nucleotide sequence encoding *P. falciparum* immunogen LSA1, wherein the nucleotide sequence comprises SEP ID NO:3;

c) a nucleotide sequence encoding *P. falciparum* immunogen CelTOS, wherein the nucleotide sequence comprises SEP ID NO:7; and d) a nucleotide sequence encoding *P. falciparum* immunogen Ama1, wherein the nucleotide sequence comprises SEP ID NO:9.

12. The immunogenic composition of claim 4 comprising one plasmid.

13. The immunogenic composition of claim 4 comprising two, three, four or five plasmids.

14. The composition of claim 4, wherein the nucleic acid molecule comprises a nucleic acid sequence as set forth in SEQ ID NO:5 operably linked to a sequence encoding an IgE signal peptide, wherein the IgE signal peptide comprises an amino acid sequence as set forth in SEQ ID NO:42.

15. A nucleic acid molecule comprising nucleic acid sequences that encodes one or more *P. falciparum* immunogens, wherein the nucleic acid molecule comprises a nucleic acid sequence encoding *P. falciparum* immunogen TRAP, wherein the nucleic acid sequence encoding *P. falciparum* immunogen TRAP comprises SEQ ID NO:5.

16. A nucleic acid molecule of claim 15, wherein said nucleic acid molecule is a plasmid.

17. A nucleic acid molecule of claim 15, wherein said nucleic acid molecule further comprises one or more nucleotide sequence encoding at least one additional *P. falciparum* immunogen selected from the group consisting of:

a) a nucleotide sequence encoding *P. falciparum* immunogen CS), wherein the nucleotide sequence comprises a sequence selected from the group consisting of SEQ ID NO:1 and SEQ ID NO:11;

b) a nucleotide sequence encoding *P. falciparum* immunogen LSA1, wherein the nucleotide sequence comprises SEQ ID NO:3;

c) a nucleotide sequence encoding *P. falciparum* immunogen CelTOS, wherein the nucleotide sequence comprises SEQ ID NO:7; and d) a nucleotide sequence encoding *P. falciparum* immunogen Ama1, wherein the nucleotide sequence comprises SEQ ID NO:9.

18. The nucleic acid molecule of claim 15, wherein the nucleic acid molecule comprises a nucleic acid sequence as set forth in SEQ ID NO:5 operably linked to a sequence encoding an IgE signal peptide, wherein the IgE signal peptide comprises an amino acid sequence as set forth in SEQ ID NO:42.

19. The immunogenic composition of claim 1, wherein the nucleic acid molecule comprises a nucleic acid sequence as set forth in SEQ ID NO:5 operably linked to a sequence encoding an IgE signal peptide, wherein the IgE signal peptide comprises an amino acid sequence as set forth in SEQ ID NO:42.

* * * * *

SEQUENCE LISTING

```
<160> NUMBER OF SEQ ID NOS: 42

<210> SEQ ID NO 1
<211> LENGTH: 1239
<212> TYPE: DNA
<213> ORGANISM: Artificial Sequence
<220> FEATURE:
<223> OTHER INFORMATION: Immunogen consensus nucleotide sequence 1

<400> SEQUENCE: 1

atgatgcgga agctggctat cctgagcgtg tccagcttcc tgttcgtgga ggccctgttc      60

caagagtacc agtgctacgg cagcagcagc aacacaagag tgctgaacga gctgaactac     120

gacaacgccg gcaccaacct gtacaacgag ctggaaatga actactacgg caagcaggaa     180

aactggtaca gcctgaagaa gaacagccgg tccctgggcg agaacgacga cggcaacaac     240

aacaacggcg acaacggcag agagggcaag gacgaggaca agcgggatgg caacaacgag     300

gacaacgaga agctgcggaa gcccaagcac aagaagctga agcagcccgg cgacggcaac     360

cccgacccca acgccaaccc caacgtggac cccaatgcca atcctaatgt cgatcccaac     420

gctaacccaa atgtcgaccc taacgcaaat cctaacgcca atcccaatgc aaaccctaat     480

gccaacccaa atgctaatcc aaacgcaaac cccaatgcta accccaacgc taaccctaat     540

gcaaatccaa atgccaaccc caacgccaac ccaaacgcca atcccaacgc taatcctaac     600

gctaacccca acgccaatcc taacgccaac ccaaacgcta acccaaatgc caaccccaat     660

gcaaatccta atgctaatcc taacgctaat ccaaatgcaa atccaaacgc taatcctaat     720

gccaacccta acgcaaaccc caacgcaaat ccaaatgcta acccaaatgc aaatcccaac     780

gccaatccaa acgcaaatcc aaatgccaat cctaatgcaa accctaatgc aaatcccaat     840

gctaatccta atgctaatcc aaacaagaac aaccagggca acggccaggg ccacaacatg     900

cccaacgacc ccaaccggaa cgtggacgag aatgccaatg ccaacaacgc cgtgaagaac     960
```

-continued

```
aacaacaatg aggaacccag cgacaagcac atcgagcagt acctcaagaa gatccagaac   1020

agcctgagca ccgagtggag cccctgtagc gtgacctgcg gcaacggcat ccaagtccgg   1080

atcaagcccg gcagcgccaa caagcccaag gacgagctgg attacgagaa cgacatcgag   1140

aagaaaatct gcaagatgga aaagtgcagc agcgtgttca acgtggtcaa cagcagcatc   1200

ggcctgatca tggtgctgag ctttctgttc ctcaactga                           1239


<210> SEQ ID NO 2
<211> LENGTH: 412
<212> TYPE: PRT
<213> ORGANISM: Artificial Sequence
<220> FEATURE:
<223> OTHER INFORMATION: Immunogen consensus amino acid sequence 1

<400> SEQUENCE: 2

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
            260                 265                 270

Ala Asn Pro Asn Ala Asn Pro Asn Ala Asn Pro Asn Ala Asn Pro Asn
        275                 280                 285

Lys Asn Asn Gln Gly Asn Gly Gln Gly His Asn Met Pro Asn Asp Pro
    290                 295                 300

Asn Arg Asn Val Asp Glu Asn Ala Asn Ala Asn Asn Ala Val Lys Asn
305                 310                 315                 320
```

-continued

```
Asn Asn Asn Glu Glu Pro Ser Asp Lys His Ile Glu Gln Tyr Leu Lys
                325                 330                 335

Lys Ile Gln Asn Ser Leu Ser Thr Glu Trp Ser Pro Cys Ser Val Thr
            340                 345                 350

Cys Gly Asn Gly Ile Gln Val Arg Ile Lys Pro Gly Ser Ala Asn Lys
        355                 360                 365

Pro Lys Asp Glu Leu Asp Tyr Glu Asn Asp Ile Glu Lys Lys Ile Cys
    370                 375                 380

Lys Met Glu Lys Cys Ser Ser Val Phe Asn Val Val Asn Ser Ser Ile
385                 390                 395                 400

Gly Leu Ile Met Val Leu Ser Phe Leu Phe Leu Asn
                405                 410


<210> SEQ ID NO 3
<211> LENGTH: 1701
<212> TYPE: DNA
<213> ORGANISM: Artificial Sequence
<220> FEATURE:
<223> OTHER INFORMATION: Immunogen consensus nucleic acid sequence 2

<400> SEQUENCE: 3

atgaagcaca tcctgtacat cagcttctac ttcatcctgg tgaacctgct gatcttccac     60

atcaacggca agatcatcaa gaacagcgag aaggacgaga tcatcaaaag caacctgcgg    120

agcggcagca gcaacagccg gaaccggatc aacgaggaaa agcacgagaa gaaacacgtg    180

ctgagccaca acagctacga aaagaccaag aacaatgaga acaacaagtt cttcgacaag    240

gacaaagaac tgaccatgag caacgtgaag aacgtgtccc agaccaactt caagagcctg    300

ctgcggaacc tgggcgtgag cgagaacatc ttcctgaaag agaacaagct gaacaaagag    360

ggcaagctga tcgagcacat catcaacgac gacgacgata agaagaagta catcaagggc    420

caggacgaga accggcagga agatctggaa gagaaggccg ccaaagagac actgcagggc    480

cagcagagcg acctggaaca ggaacggctg gccaaagaaa agctgcagga acagcagtcc    540

gacagcgagc aggaaagact ggctaaagag aaactccaag agcagcagtc tgacttggag    600

caggaacgcc tcgcaaaaga gaagttgcaa gagcaacagt ccgatctgga acaagagcgc    660

ctcgctaaag aaaaacttca ggaacaacag agcgatttgg agcaagagcg gagagccaaa    720

gagaaattgc aggaacaaca atctgacctc gaacaggaaa gaagggccaa agagaagctt    780

caagaacaac aaagtgacct tgagcaagag aggcgggcta aagaaaaatt gcaagaacag    840

cagcgggatc tcgaacagcg gaaggccgac accaagaaga acctggaacg gaagaaagaa    900

cacggcgacg tgctggccga ggacctgtac ggcagactgg aaatccccgc catcgagctg    960

cccagcgaga acgagcgggg ctactacatc ccccaccaga gcagcctgcc ccaggacaac   1020

cggggcaaca gcagagacag caaagagatc agcatcatcg agaaaacaaa ccgggagagc   1080

atcaccacca acgtggaggg cagacgggac atccacaagg gccacctgga agaaaagaag   1140

gacggcagca tcaagcccga gcagaaagag gacaagagcg ccgacatcca gaaccacacc   1200

ctggaaaccg tgaacatcag cgacgtgaac gacttccaga tcagcaagta cgaggatgag   1260

atcagcgccg agtacgacga cagcctgatc gacgaggaag aggacgacga ggacctggac   1320

gagttcaagc ccatcgtgca gtacgacaac ttccaggacg aggaaaacat cggcatctac   1380

aaagagctgg aagatctgat cgagaagaac gagaacctgg atgatctgga cgagggcatc   1440

gagaagtcca gcgaggaact gagcgaggaa aagatcaaga agggcaagaa gtacgagaaa   1500
```

-continued

```
actaaggaca acaacttcaa gcccaacgac aagagcctgt acgatgagca catcaagaag   1560

tacaaaaacg acaaacaggt gaacaaagaa aaagagaagt tcatcaagtc cctgttccac   1620

atcttcgacg gcgacaacga gatcctgcag atcgtggatg agctgtccga ggacatcacc   1680

aagtacttca tgaagctgtg a                                             1701
```

<210> SEQ ID NO 4
<211> LENGTH: 565
<212> TYPE: PRT
<213> ORGANISM: Artificial Sequence
<220> FEATURE:
<223> OTHER INFORMATION: Immunogen consensus amino acid sequence 2

<400> SEQUENCE: 4

```
Met Lys His Ile Leu Tyr Ile Ser Phe Tyr Phe Ile Leu Val Asn Leu
1               5                   10                  15

Leu Ile Phe His Ile Asn Gly Lys Ile Ile Lys Asn Ser Glu Lys Asp
            20                  25                  30

Glu Ile Ile Lys Ser Asn Leu Arg Ser Gly Ser Ser Asn Ser Arg Asn
        35                  40                  45

Arg Ile Asn Glu Glu Lys His Glu Lys Lys His Val Leu Ser His Asn
    50                  55                  60

Ser Tyr Glu Lys Thr Lys Asn Asn Glu Asn Asn Lys Phe Phe Asp Lys
65                  70                  75                  80

Lys Glu Leu Thr Met Ser Asn Val Lys Asn Val Ser Gln Thr Asn Phe
                85                  90                  95

Lys Ser Leu Leu Arg Asn Leu Gly Val Ser Glu Asn Ile Phe Leu Lys
            100                 105                 110

Glu Asn Lys Leu Asn Lys Glu Gly Lys Leu Ile Glu His Ile Ile Asn
        115                 120                 125

Asp Asp Asp Asp Lys Lys Lys Tyr Ile Lys Gly Gln Asp Glu Asn Arg
    130                 135                 140

Gln Glu Asp Leu Glu Glu Lys Ala Ala Lys Glu Thr Leu Gln Gly Gln
145                 150                 155                 160

Gln Ser Asp Leu Glu Gln Glu Arg Leu Ala Lys Glu Lys Leu Gln Glu
                165                 170                 175

Gln Gln Ser Asp Ser Glu Gln Glu Arg Leu Ala Lys Glu Lys Leu Gln
            180                 185                 190

Glu Gln Gln Ser Asp Leu Glu Gln Glu Arg Leu Ala Lys Glu Lys Leu
        195                 200                 205

Gln Glu Gln Gln Ser Asp Leu Glu Gln Glu Arg Leu Ala Lys Glu Lys
    210                 215                 220

Leu Gln Glu Gln Gln Ser Asp Leu Glu Gln Glu Arg Arg Ala Lys Glu
225                 230                 235                 240

Lys Leu Gln Glu Gln Gln Ser Asp Leu Glu Gln Glu Arg Arg Ala Lys
                245                 250                 255

Glu Lys Leu Gln Glu Gln Gln Ser Asp Leu Glu Gln Glu Arg Arg Ala
            260                 265                 270

Lys Glu Lys Leu Gln Glu Gln Gln Arg Asp Leu Glu Gln Arg Lys Ala
        275                 280                 285

Asp Thr Lys Lys Asn Leu Glu Arg Lys Lys Glu His Gly Asp Val Leu
    290                 295                 300

Ala Glu Asp Leu Tyr Gly Arg Leu Glu Ile Pro Ala Ile Glu Leu Pro
305                 310                 315                 320

Ser Glu Asn Glu Arg Gly Tyr Tyr Ile Pro His Gln Ser Ser Leu Pro
```

```
            325                 330                 335

Gln Asp Asn Arg Gly Asn Ser Arg Asp Ser Lys Glu Ile Ser Ile Ile
        340                 345                 350

Glu Lys Thr Asn Arg Glu Ser Ile Thr Thr Asn Val Glu Gly Arg Arg
    355                 360                 365

Asp Ile His Lys Gly His Leu Glu Glu Lys Lys Asp Gly Ser Ile Lys
370                 375                 380

Pro Glu Gln Lys Glu Asp Lys Ser Ala Asp Ile Gln Asn His Thr Leu
385                 390                 395                 400

Glu Thr Val Asn Ile Ser Asp Val Asn Asp Phe Gln Ile Ser Lys Tyr
                405                 410                 415

Glu Asp Glu Ile Ser Ala Glu Tyr Asp Asp Ser Leu Ile Asp Glu Glu
            420                 425                 430

Glu Asp Asp Glu Asp Leu Asp Glu Phe Lys Pro Ile Val Gln Tyr Asp
        435                 440                 445

Asn Phe Gln Asp Glu Glu Asn Ile Gly Ile Tyr Lys Glu Leu Glu Asp
    450                 455                 460

Leu Ile Glu Lys Asn Glu Asn Leu Asp Asp Leu Asp Glu Gly Ile Glu
465                 470                 475                 480

Lys Ser Ser Glu Glu Leu Ser Glu Glu Lys Ile Lys Lys Gly Lys Lys
                485                 490                 495

Tyr Glu Lys Thr Lys Asp Asn Asn Phe Lys Pro Asn Asp Lys Ser Leu
            500                 505                 510

Tyr Asp Glu His Ile Lys Lys Tyr Lys Asn Asp Lys Gln Val Asn Lys
        515                 520                 525

Glu Lys Glu Lys Phe Ile Lys Ser Leu Phe His Ile Phe Asp Gly Asp
    530                 535                 540

Asn Glu Ile Leu Gln Ile Val Asp Glu Leu Ser Glu Asp Ile Thr Lys
545                 550                 555                 560

Tyr Phe Met Lys Leu
                565
```

<210> SEQ ID NO 5
<211> LENGTH: 1680
<212> TYPE: DNA
<213> ORGANISM: Artificial Sequence
<220> FEATURE:
<223> OTHER INFORMATION: Immunogen consensus nucleic acid sequence 3

<400> SEQUENCE: 5

```
atgaaccacc tgggcaacgt gaagtacctg gtgatcgtgt tcctgatctt cttcgacctg      60

tttctggtga acggccggga cgtgcagaac aacatcgtgg acgagatcaa gtaccgggag     120

gaagtgtgca acgacgaggt ggacctgtac ctgctgatgg actgcagcgg cagcatcaga     180

cggcacaact gggtgaacca cgccgtgccc ctggccatga agctgatcca gcagctgaac     240

ctgaacgaga acgccatcca cctgtacgtg aacgacttca gcaacaacgc caaagagatc     300

atccggctgc acagcgacgc cagcaagaac aaagagaagg ccctgatcat catcaagagc     360

ctgctgagca ccaacctgcc ctacggccgg accaacctgt ctgacgctct gctgcaggtg     420

cggaagcacc tgaacgaccg gatcaaccgg gagaacgcca accagctggt ggtgatcctg     480

accgacggca tccccgacag catccaggac agcctgaaag agagccggaa gctgaacgac     540

agaggcgtga agatcgccgt gttcggcatc ggccagggca tcaacgtggc cttcaacaga     600

ttcctggtgg gctgtcaccc cagcgacggc aagtgcaacc tgtacgccga cagcgcctgg     660
```

-continued

```
gagaacgtga agaatgtgat cggccccttc atgaaggccg tgtgcgtgga ggtggagaaa    720

accgccagct gcggcgtgtg ggatgagtgg agcccctgca gcgtgacctg tggcaagggc    780

accagaagcc ggaagcggga gatcctgcac gagggctgca ccagcgagct gcaggaacag    840

tgcgaagagg aacggtgccc ccccaagagg gaacccctgg acgtgcccca cgagcccgag    900

gacgaccagc ccagacccag aggcgacaac ttcgccgtgg agaagcccga ggaaaacatc    960

atcgacaaca acccccagga acccagcccc aaccctgagg aaggcaaggg cgagaacccc   1020

aacggcttcg acctggacga gaaccccgag aatcccccca accccgacat ccccgagcag   1080

gaacccaaca tccctgagga cagcgagaaa gaggtgccca gcgacgtccc caagaatccc   1140

gaggatgacc gggaagagaa cttcgacatc cccaagaagc ctgagaacaa gcacgacaac   1200

cagaacaacc tgcccaacga caagagcgac cggtacatcc cctacagccc cctgcccccc   1260

aaggtgctgg acaacgagcg gaagcagagc gacccccaga gccaggacaa caacggcaac   1320

cggcacgtgc ccaacagcga ggaccgggag acaagacccc acggccggaa caacgagaac   1380

cggtcctaca accggaagta caacgacacc cccaagcacc ccgagcggga ggaacacgag   1440

aaacccgaca acaacaagaa gaagggcggc agcgacaaca agtacaagat tgccggcgga   1500

atcgctggcg gactggccct gctggcttgt gccggcctgg cctacaagtt tgtggtgcct   1560

ggcgccgcta caccttatgc cggcgagcct gcccccttg acgagacact gggcgaagag   1620

gacaaggacc tggatgagcc cgagcagttc cggctgcccg aagagaacga gtggaactga   1680


<210> SEQ ID NO 6
<211> LENGTH: 559
<212> TYPE: PRT
<213> ORGANISM: Artificial Sequence
<220> FEATURE:
<223> OTHER INFORMATION: Immunogen consensus amino acid sequence 3

<400> SEQUENCE: 6

Met Asn His Leu Gly Asn Val Lys Tyr Leu Val Ile Val Phe Leu Ile
1               5                   10                  15

Phe Phe Asp Leu Phe Leu Val Asn Gly Arg Asp Val Gln Asn Asn Ile
            20                  25                  30

Val Asp Glu Ile Lys Tyr Arg Glu Glu Val Cys Asn Asp Glu Val Asp
        35                  40                  45

Leu Tyr Leu Leu Met Asp Cys Ser Gly Ser Ile Arg Arg His Asn Trp
    50                  55                  60

Val Asn His Ala Val Pro Leu Ala Met Lys Leu Ile Gln Gln Leu Asn
65                  70                  75                  80

Leu Asn Glu Asn Ala Ile His Leu Tyr Val Asn Asp Phe Ser Asn Asn
                85                  90                  95

Ala Lys Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
        115                 120                 125

Gly Arg Thr Asn Leu Ser Asp Ala Leu Leu Gln Val Arg Lys His Leu
    130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Asn Asp Arg Gly Val Lys Ile Ala Val Phe Gly Ile Gly Gln
            180                 185                 190
```

```
Gly Ile Asn Val Ala Phe Asn Arg Phe Leu Val Gly Cys His Pro Ser
        195                 200                 205

Asp Gly Lys Cys Asn Leu Tyr Ala Asp Ser Ala Trp Glu Asn Val Lys
    210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270

Cys Thr Ser Glu Leu Gln Glu Gln Cys Glu Glu Glu Arg Cys Pro Pro
        275                 280                 285

Lys Arg Glu Pro Leu Asp Val Pro His Glu Pro Glu Asp Asp Gln Pro
    290                 295                 300

Arg Pro Arg Gly Asp Asn Phe Ala Val Glu Lys Pro Glu Glu Asn Ile
305                 310                 315                 320

Ile Asp Asn Asn Pro Gln Glu Pro Ser Pro Asn Pro Glu Glu Gly Lys
                325                 330                 335

Gly Glu Asn Pro Asn Gly Phe Asp Leu Asp Glu Asn Pro Glu Asn Pro
            340                 345                 350

Pro Asn Pro Asp Ile Pro Glu Gln Glu Pro Asn Ile Pro Glu Asp Ser
        355                 360                 365

Glu Lys Glu Val Pro Ser Asp Val Pro Lys Asn Pro Glu Asp Asp Arg
    370                 375                 380

Glu Glu Asn Phe Asp Ile Pro Lys Lys Pro Glu Asn Lys His Asp Asn
385                 390                 395                 400

Gln Asn Asn Leu Pro Asn Asp Lys Ser Asp Arg Tyr Ile Pro Tyr Ser
                405                 410                 415

Pro Leu Pro Pro Lys Val Leu Asp Asn Glu Arg Lys Gln Ser Asp Pro
            420                 425                 430

Gln Ser Gln Asp Asn Asn Gly Asn Arg His Val Pro Asn Ser Glu Asp
        435                 440                 445

Arg Glu Thr Arg Pro His Gly Arg Asn Asn Glu Asn Arg Ser Tyr Asn
    450                 455                 460

Arg Lys Tyr Asn Asp Thr Pro Lys His Pro Glu Arg Glu Glu His Glu
465                 470                 475                 480

Lys Pro Asp Asn Asn Lys Lys Lys Gly Gly Ser Asp Asn Lys Tyr Lys
                485                 490                 495

Ile Ala Gly Gly Ile Ala Gly Gly Leu Ala Leu Leu Ala Cys Ala Gly
            500                 505                 510

Leu Ala Tyr Lys Phe Val Val Pro Gly Ala Ala Thr Pro Tyr Ala Gly
        515                 520                 525

Glu Pro Ala Pro Phe Asp Glu Thr Leu Gly Glu Glu Asp Lys Asp Leu
    530                 535                 540

Asp Glu Pro Glu Gln Phe Arg Leu Pro Glu Glu Asn Glu Trp Asn
545                 550                 555
```

<210> SEQ ID NO 7
<211> LENGTH: 549
<212> TYPE: DNA
<213> ORGANISM: Artificial Sequence
<220> FEATURE:
<223> OTHER INFORMATION: Immunogen consensus nucleic acid sequence 4

<400> SEQUENCE: 7

```
atgaacgccc tgcggagact gcccgtgatc tgcagcttcc tggtgtttct ggtgttcagc     60

aacgtgctgt gcttccgggg caacaacggc cacaacagca gcagcagcct gtacaacggc    120

agccagttca tcgagcagct gaacaacagc ttcaccagcg cctttctgga aagccagagc    180

atgaacaaga tcggcgacga cctggccgag acaatcagca acgagctggt gtccgtgctg    240

cagaagaaca gccccacctt cctggaaagc agcttcgaca tcaagagcga agtgaagaaa    300

cacgccaaga gcatgctgaa agaactgatc aaagtgggcc tgcccagctt cgagaatctg    360

gtcgccgaga acgtgaagcc ccccaaggtg gaccctgcca catacggcat catcgtgccc    420

gtgctgacca gcctgttcaa caaggtggag acagccgtgg gcgccaaggt gtccgacgag    480

atctggaact acaacagccc cgacgtgtcc gagagcgagg aaagcctgag cgacgacttc    540

ttcgactga                                                            549
```

```
<210> SEQ ID NO 8
<211> LENGTH: 182
<212> TYPE: PRT
<213> ORGANISM: Artificial Sequence
<220> FEATURE:
<223> OTHER INFORMATION: Immunogen consensus amino acid sequence 4

<400> SEQUENCE: 8

Met Asn Ala Leu Arg Arg Leu Pro Val Ile Cys Ser Phe Leu Val Phe
1               5                   10                  15

Leu Val Phe Ser Asn Val Leu Cys Phe Arg Gly Asn Asn Gly His Asn
            20                  25                  30

Ser Ser Ser Ser Leu Tyr Asn Gly Ser Gln Phe Ile Glu Gln Leu Asn
        35                  40                  45

Asn Ser Phe Thr Ser Ala Phe Leu Glu Ser Gln Ser Met Asn Lys Ile
    50                  55                  60

Gly Asp Asp Leu Ala Glu Thr Ile Ser Asn Glu Leu Val Ser Val Leu
65                  70                  75                  80

Gln Lys Asn Ser Pro Thr Phe Leu Glu Ser Ser Phe Asp Ile Lys Ser
                85                  90                  95

Glu Val Lys Lys His Ala Lys Ser Met Leu Lys Glu Leu Ile Lys Val
            100                 105                 110

Gly Leu Pro Ser Phe Glu Asn Leu Val Ala Glu Asn Val Lys Pro Pro
        115                 120                 125

Lys Val Asp Pro Ala Thr Tyr Gly Ile Ile Val Pro Val Leu Thr Ser
    130                 135                 140

Leu Phe Asn Lys Val Glu Thr Ala Val Gly Ala Lys Val Ser Asp Glu
145                 150                 155                 160

Ile Trp Asn Tyr Asn Ser Pro Asp Val Ser Glu Ser Glu Glu Ser Leu
                165                 170                 175

Ser Asp Asp Phe Phe Asp
            180


<210> SEQ ID NO 9
<211> LENGTH: 1866
<212> TYPE: DNA
<213> ORGANISM: Artificial Sequence
<220> FEATURE:
<223> OTHER INFORMATION: Immunogen consensus nucleic acid sequence 5

<400> SEQUENCE: 9

atgagaaaac tgtattgcgt gctgctgctg agcgccttcg agttcaccta tatgatcaac     60
```

-continued

```
ttcggaaggg gccagaatta ctgggagcac ccctatcaga actctgacgt gtaccgacct    120

attaatgaac accgggagca tcccaaggag tacgaatatc ctctgcacca ggaacataca    180

tatcagcagg aggacagcgg ggaggatgaa aacactctgc agcacgccta cccaatcgac    240

catgaaggag ctgagccagc accccaggag cagaatctgt ttagctccat cgaaattgtg    300

gagcgcagta actacatggg caatccctgg accgagtaca tggccaagta tgatatcgag    360

gaagtccacg ggtccggaat tcgcgtggac ctgggcgaag atgccgaggt cgctgggaca    420

cagtatcgac tgccttccgg caaatgccca gtgttcggca aggggatcat tatcgagaac    480

tctaatacca catttctgac ccccgtggcc acagggaacc agtacctgaa ggacggcgga    540

ttcgcttttc cccctactga acccctgatg tctcctatga ccctggacga gatgaggcac    600

ttctacaagg ataacaaata cgtcaagaat ctggacgagc tgactctgtg ctcacgccat    660

gctggaaaca tgatcccaga caacgataag aacagcaact acaagtatcc cgcagtgtac    720

gacgataagg acaagaaatg tcacatcctg tatattgccg ctcaggaaaa caatggcccc    780

cggtactgca acaaagatga gtctaagaga aacagtatgt tctgtttcag gcctgcaaaa    840

gacatcagtt tccagaacta cacatatctg tcaaagaacg tggtcgataa ttgggagaaa    900

gtgtgcccca gaaagaacct gcagaatgct aagtttgggc tgtgggtcga cggaaactgc    960

gaagatatcc cacacgtgaa tgagttcccc gcaattgacc tgtttgaatg taacaagctg   1020

gtgttcgagc tgtccgcctc tgatcagcct aagcagtacg agcagcatct gacagactat   1080

gaaaagatca aagagggctt taagaacaaa aacgcatcaa tgatcaagag cgccttcctg   1140

ccaactgggg ccttcaaggc cgataggtac aaaagccacg gaaagggcta caactgggga   1200

aactataata cagaaactca gaaatgcgag atcttcaatg tcaagcccac ctgtctgatc   1260

aacaattcta gttacatcgc tactaccgca ctgtctcatc ctattgaggt ggaaaacaat   1320

tttccatgca gtctgtacaa agacgaaatc atgaaggaga ttgaaaggga gagcaaacgc   1380

atcaagctga acgataatga cgatgagggg aacaagaaaa ttatcgcccc tcgaatcttc   1440

atttccgacg ataaagactc tctgaagtgc ccttgtgatc cagagatggt cagtaattca   1500

acctgtcgct tctttgtctg caagtgcgtg gaacggagag ccgaggtgac atccaacaat   1560

gaggtggtcg tgaaagagga atacaaggac gaatatgccg atatcccaga gcacaagccc   1620

acttacgaca agatgaaaat tatcattgct tcaagcgcag ccgtcgccgt gctggctacc   1680

attctgatgg tgtacctgta taagagaaaa ggaaacgccg aaaaatacga caagatggat   1740

gagcctcagg attatggcaa aagcaactcc cggaatgacg aaatgctgga ccccgaggct   1800

agcttttggg gcgaggaaaa gagagcatcc cataccaccc ccgtcctgat ggaaaagcct   1860

tactat                                                              1866
```

```
<210> SEQ ID NO 10
<211> LENGTH: 622
<212> TYPE: PRT
<213> ORGANISM: Artificial Sequence
<220> FEATURE:
<223> OTHER INFORMATION: Immunogen consensus amino acid sequence 5

<400> SEQUENCE: 10

Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
```

-continued

```
        35                  40                  45

Lys Glu Tyr Glu Tyr Pro Leu His Gln Glu His Thr Tyr Gln Gln Glu
    50                  55                  60

Asp Ser Gly Glu Asp Glu Asn Thr Leu Gln His Ala Tyr Pro Ile Asp
65                  70                  75                  80

His Glu Gly Ala Glu Pro Ala Pro Gln Glu Gln Asn Leu Phe Ser Ser
                85                  90                  95

Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
        115                 120                 125

Val Asp Leu Gly Glu Asp Ala Glu Val Ala Gly Thr Gln Tyr Arg Leu
    130                 135                 140

Pro Ser Gly Lys Cys Pro Val Phe Gly Lys Gly Ile Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
    210                 215                 220

Ile Pro Asp Asn Asp Lys Asn Ser Asn Tyr Lys Tyr Pro Ala Val Tyr
225                 230                 235                 240

Asp Asp Lys Asp Lys Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
        275                 280                 285

Tyr Leu Ser Lys Asn Val Val Asp Asn Trp Glu Lys Val Cys Pro Arg
    290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
        355                 360                 365

Asn Lys Asn Ala Ser Met Ile Lys Ser Ala Phe Leu Pro Thr Gly Ala
    370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Asn Asn Ser Ser Tyr Ile Ala Thr Thr Ala Leu Ser
            420                 425                 430

His Pro Ile Glu Val Glu Asn Asn Phe Pro Cys Ser Leu Tyr Lys Asp
        435                 440                 445

Glu Ile Met Lys Glu Ile Glu Arg Glu Ser Lys Arg Ile Lys Leu Asn
    450                 455                 460
```

```
Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Asn Ser Thr Cys Arg Phe Phe Val Cys Lys Cys Val Glu Arg
            500                 505                 510

Arg Ala Glu Val Thr Ser Asn Asn Glu Val Val Val Lys Glu Glu Tyr
        515                 520                 525

Lys Asp Glu Tyr Ala Asp Ile Pro Glu His Lys Pro Thr Tyr Asp Lys
    530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Glu Lys Arg
        595                 600                 605

Ala Ser His Thr Thr Pro Val Leu Met Glu Lys Pro Tyr Tyr
    610                 615                 620
```

```
<210> SEQ ID NO 11
<211> LENGTH: 1083
<212> TYPE: DNA
<213> ORGANISM: Artificial Sequence
<220> FEATURE:
<223> OTHER INFORMATION: Immunogen consensus nucleic acid sequence 6

<400> SEQUENCE: 11

atgatgcgga agctggctat cctgagcgtg tccagcttcc tgttcgtgga ggccctgttc      60

caagagtacc agtgctacgg cagcagcagc aacacaagag tgctgaacga gctgaactac     120

gacaacgccg gcaccaacct gtacaacgag ctggaaatga actactacgg caagcaggaa     180

aactggtaca gcctgaagaa gaacagccgg tccctgggcg agaacgacga cggcaacaac     240

aacaacggcg acaacggcag agagggcaag gacgaggaca agcgggatgg caacaacgag     300

gacaacgaga agctgcggaa gcccaagcac aagaagctga agcagcccgg cgacggcaac     360

cccgaccccca acgccaaccc caacgtggac cccaatgcca atcctaatgt cgatcccaac     420

gctaacccaa atgtcgaccc taacgcaaat cctaacgcca atcccaatgc aaaccctaat     480

gccaacccaa atgctaatcc aaacgcaaac cccaatgcta accccaacgc taaccctaat     540

gcaaatccaa atgccaaccc caacgccaac ccaaacgcca atcccaacgc taatcctaac     600

gctaacccca acgccaatcc taacgccaac ccaaacgcta acccaaatgc caaccccaat     660

gcaaatccta atgctaatcc taacgctaat ccaaatgcaa atccaaacaa gaacaaccag     720

ggcaacggcc agggccacaa catgcccaac gaccccaacc ggaacgtgga cgagaatgcc     780

aatgccaaca acgccgtgaa gaacaacaac aatgaggaac ccagcgacaa gcacatcgag     840

cagtacctca agaagatcca gaacagcctg agcaccgagt ggagcccctg tagcgtgacc     900

tgcggcaacg gcatccaagt ccggatcaag cccggcagcg ccaacaagcc caaggacgag     960

ctggattacg agaacgacat cgagaagaaa atctgcaaga tggaaaagtg cagcagcgtg    1020

ttcaacgtgg tcaacagcag catcggcctg atcatggtgc tgagctttct gttcctcaac    1080

tga                                                                 1083
```

-continued

<210> SEQ ID NO 12
<211> LENGTH: 360
<212> TYPE: PRT
<213> ORGANISM: Artificial Sequence
<220> FEATURE:
<223> OTHER INFORMATION: Immunogen consensus amino acid sequence 6

<400> SEQUENCE: 12

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Asn Asn Gly Asp Asn Gly Arg Glu Gly Lys Asp Glu Asp Lys Arg Asp
                85                  90                  95

Gly Asn Asn Glu Asp Asn Glu Lys Leu Arg Lys Pro Lys His Lys Lys
            100                 105                 110

Leu Lys Gln Pro Gly Asp Gly Asn Pro Asp Pro Asn Ala Asn Pro Asn
        115                 120                 125

Val Asp Pro Asn Ala Asn Pro Asn Val Asp Pro Asn Ala Asn Pro Asn
    130                 135                 140

Val Asp Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Ala Asn Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Lys Asn Asn Gln
225                 230                 235                 240

Gly Asn Gly Gln Gly His Asn Met Pro Asn Asp Pro Asn Arg Asn Val
                245                 250                 255

Asp Glu Asn Ala Asn Ala Asn Asn Ala Val Lys Asn Asn Asn Asn Glu
            260                 265                 270

Glu Pro Ser Asp Lys His Ile Glu Gln Tyr Leu Lys Lys Ile Gln Asn
        275                 280                 285

Ser Leu Ser Thr Glu Trp Ser Pro Cys Ser Val Thr Cys Gly Asn Gly
    290                 295                 300

Ile Gln Val Arg Ile Lys Pro Gly Ser Ala Asn Lys Pro Lys Asp Glu
305                 310                 315                 320

Leu Asp Tyr Glu Asn Asp Ile Glu Lys Lys Ile Cys Lys Met Glu Lys
                325                 330                 335

Cys Ser Ser Val Phe Asn Val Val Asn Ser Ser Ile Gly Leu Ile Met
            340                 345                 350

Val Leu Ser Phe Leu Phe Leu Asn
        355                 360
```

-continued

<210> SEQ ID NO 13
<211> LENGTH: 1290
<212> TYPE: DNA
<213> ORGANISM: Artificial Sequence
<220> FEATURE:
<223> OTHER INFORMATION: Immunogen consensus nucleic acid sequence 7

<400> SEQUENCE: 13

```
atggactgga cctggattct gttcctggtg gccgctgcca cacgggtgca cagcatgcgg     60

aagctggcta tcctgagcgt gtccagcttc ctgttcgtgg aggccctgtt ccaagagtac    120

cagtgctacg gcagcagcag caacacaaga gtgctgaacg agctgaacta cgacaacgcc    180

ggcaccaacc tgtacaacga gctggaaatg aactactacg gcaagcagga aaactggtac    240

agcctgaaga agaacagccg gtccctgggc gagaacgacg acggcaacaa caacaacggc    300

gacaacggca gagagggcaa ggacgaggac aagcgggatg gcaacaacga ggacaacgag    360

aagctgcgga agcccaagca caagaagctg aagcagcccg gcgacggcaa ccccgacccc    420

aacgccaacc ccaacgtgga ccccaatgcc aatcctaatg tcgatcccaa cgctaaccca    480

aatgtcgacc ctaacgcaaa tcctaacgcc aatcccaatg caaaccctaa tgccaaccca    540

aatgctaatc caaacgcaaa ccccaatgct aaccccaacg ctaaccctaa tgcaaatcca    600

aatgccaacc ccaacgccaa cccaaacgcc aatcccaacg ctaatcctaa cgctaacccc    660

aacgccaatc ctaacgccaa cccaaacgct aacccaaatg ccaaccccaa tgcaaatcct    720

aatgctaatc ctaacgctaa tccaaatgca aatccaaacg ctaatcctaa tgccaaccct    780

aacgcaaacc ccaacgcaaa tccaaatgct aacccaaatg caaatcccaa cgccaatcca    840

aacgcaaatc caaatgccaa tcctaatgca aaccctaatg caaatcccaa tgctaatcct    900

aatgctaatc caaacaagaa caaccagggc aacggccagg gccacaacat gcccaacgac    960

cccaaccgga acgtggacga gaatgccaat gccaacaacg ccgtgaagaa caacaacaat   1020

gaggaaccca gcgacaagca catcgagcag tacctcaaga agatccagaa cagcctgagc   1080

accgagtgga gcccctgtag cgtgacctgc ggcaacggca tccaagtccg gatcaagccc   1140

ggcagcgcca acaagcccaa ggacgagctg gattacgaga acgacatcga gaagaaaatc   1200

tgcaagatgg aaaagtgcag cagcgtgttc aacgtggtca acagcagcat cggcctgatc   1260

atggtgctga gctttctgtt cctcaactga                                     1290
```

<210> SEQ ID NO 14
<211> LENGTH: 429
<212> TYPE: PRT
<213> ORGANISM: Artificial Sequence
<220> FEATURE:
<223> OTHER INFORMATION: Immunogen consensus amino acid sequence 7

<400> SEQUENCE: 14

```
Met Asp Trp Thr Trp Ile Leu Phe Leu Val Ala Ala Ala Thr Arg Val
1               5                   10                  15

His Ser Met Arg Lys Leu Ala Ile Leu Ser Val Ser Ser Phe Leu Phe
            20                  25                  30

Val Glu Ala Leu Phe Gln Glu Tyr Gln Cys Tyr Gly Ser Ser Ser Asn
        35                  40                  45

Thr Arg Val Leu Asn Glu Leu Asn Tyr Asp Asn Ala Gly Thr Asn Leu
    50                  55                  60

Tyr Asn Glu Leu Glu Met Asn Tyr Tyr Gly Lys Gln Glu Asn Trp Tyr
65                  70                  75                  80
```

-continued

```
Ser Leu Lys Lys Asn Ser Arg Ser Leu Gly Glu Asn Asp Asp Gly Asn
                85                  90                  95

Asn Asn Asn Gly Asp Asn Gly Arg Glu Gly Lys Asp Glu Asp Lys Arg
            100                 105                 110

Asp Gly Asn Asn Glu Asp Asn Glu Lys Leu Arg Lys Pro Lys His Lys
        115                 120                 125

Lys Leu Lys Gln Pro Gly Asp Gly Asn Pro Asp Pro Asn Ala Asn Pro
    130                 135                 140

Asn Val Asp Pro Asn Ala Asn Pro Asn Val Asp Pro Asn Ala Asn Pro
145                 150                 155                 160

Asn Val Asp Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Ala Asn Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Ala Asn Pro Asn Ala Asn Pro Asn Ala Asn Pro Asn Ala Asn Pro
        275                 280                 285

Asn Ala Asn Pro Asn Ala Asn Pro Asn Ala Asn Pro Asn Ala Asn Pro
    290                 295                 300

Asn Lys Asn Asn Gln Gly Asn Gly Gln Gly His Asn Met Pro Asn Asp
305                 310                 315                 320

Pro Asn Arg Asn Val Asp Glu Asn Ala Asn Ala Asn Asn Ala Val Lys
                325                 330                 335

Asn Asn Asn Asn Glu Glu Pro Ser Asp Lys His Ile Glu Gln Tyr Leu
            340                 345                 350

Lys Lys Ile Gln Asn Ser Leu Ser Thr Glu Trp Ser Pro Cys Ser Val
        355                 360                 365

Thr Cys Gly Asn Gly Ile Gln Val Arg Ile Lys Pro Gly Ser Ala Asn
    370                 375                 380

Lys Pro Lys Asp Glu Leu Asp Tyr Glu Asn Asp Ile Glu Lys Lys Ile
385                 390                 395                 400

Cys Lys Met Glu Lys Cys Ser Ser Val Phe Asn Val Val Asn Ser Ser
                405                 410                 415

Ile Gly Leu Ile Met Val Leu Ser Phe Leu Phe Leu Asn
            420                 425
```

<210> SEQ ID NO 15
<211> LENGTH: 1752
<212> TYPE: DNA
<213> ORGANISM: Artificial Sequence
<220> FEATURE:
<223> OTHER INFORMATION: Immunogen consensus nucleic acid sequence 8

<400> SEQUENCE: 15

```
atggactgga cctggattct gttcctcgtc gcagctgcca ccagagtgca cagcaagcac      60

atcctgtaca tcagcttcta cttcatcctg gtgaacctgc tgatcttcca catcaacggc     120
```

```
aagatcatca agaacagcga gaaggacgag atcatcaaaa gcaacctgcg gagcggcagc    180

agcaacagcc ggaaccggat caacgaggaa aagcacgaga agaaacacgt gctgagccac    240

aacagctacg aaaagaccaa gaacaatgag aacaacaagt tcttcgacaa ggacaaagaa    300

ctgaccatga gcaacgtgaa gaacgtgtcc cagaccaact tcaagagcct gctgcggaac    360

ctgggcgtga gcgagaacat cttcctgaaa gagaacaagc tgaacaaaga gggcaagctg    420

atcgagcaca tcatcaacga cgacgacgat aagaagaagt acatcaaggg ccaggacgag    480

aaccggcagg aagatctgga agagaaggcc gccaaagaga cactgcaggg ccagcagagc    540

gacctggaac aggaacggct ggccaaagaa aagctgcagg aacagcagtc cgacagcgag    600

caggaaagac tggctaaaga gaaactccaa gagcagcagt ctgacttgga gcaggaacgc    660

ctcgcaaaag agaagttgca agagcaacag tccgatctgg aacaagagcg cctcgctaaa    720

gaaaaacttc aggaacaaca gagcgatttg gagcaagagc ggagagccaa agagaaattg    780

caggaacaac aatctgacct cgaacaggaa agaagggcca aagagaagct tcaagaacaa    840

caaagtgacc ttgagcaaga gaggcgggct aaagaaaaat tgcaagaaca gcagcgggat    900

ctcgaacagc ggaaggccga caccaagaag aacctggaac ggaagaaaga acacggcgac    960

gtgctggccg aggacctgta cggcagactg gaaatccccg ccatcgagct gcccagcgag   1020

aacgagcggg gctactacat cccccaccag agcagcctgc cccaggacaa ccggggcaac   1080

agcagagaca gcaaagagat cagcatcatc gagaaaacaa accgggagag catcaccacc   1140

aacgtggagg gcagacggga catccacaag ggccacctgg aagaaaagaa ggacggcagc   1200

atcaagcccg agcagaaaga ggacaagagc gccgacatcc agaaccacac cctggaaacc   1260

gtgaacatca gcgacgtgaa cgacttccag atcagcaagt acgaggatga gatcagcgcc   1320

gagtacgacg acagcctgat cgacgaggaa gaggacgacg aggacctgga cgagttcaag   1380

cccatcgtgc agtacgacaa cttccaggac gaggaaaaca tcggcatcta caaagagctg   1440

gaagatctga tcgagaagaa cgagaacctg gatgatctgg acgagggcat cgagaagtcc   1500

agcgaggaac tgagcgagga aaagatcaag aagggcaaga agtacgagaa aactaaggac   1560

aacaacttca agcccaacga caagagcctg tacgatgagc acatcaagaa gtacaaaaac   1620

gacaaacagg tgaacaaaga aaaagagaag ttcatcaagt ccctgttcca catcttcgac   1680

ggcgacaacg agatcctgca gatcgtggat gagctgtccg aggacatcac caagtacttc   1740

atgaagctgt ga                                                       1752
```

<210> SEQ ID NO 16
<211> LENGTH: 582
<212> TYPE: PRT
<213> ORGANISM: Artificial Sequence
<220> FEATURE:
<223> OTHER INFORMATION: Immunogen consensus amino acid sequence 8

<400> SEQUENCE: 16

```
Met Asp Trp Thr Trp Ile Leu Phe Leu Val Ala Ala Ala Thr Arg Val
1               5                   10                  15

His Ser Lys His Ile Leu Tyr Ile Ser Phe Tyr Phe Ile Leu Val Asn
            20                  25                  30

Leu Leu Ile Phe His Ile Asn Gly Lys Ile Ile Lys Asn Ser Glu Lys
        35                  40                  45

Asp Glu Ile Ile Lys Ser Asn Leu Arg Ser Gly Ser Ser Asn Ser Arg
    50                  55                  60
```

-continued

```
Asn Arg Ile Asn Glu Glu Lys His Glu Lys Lys His Val Leu Ser His
65                  70                  75                  80

Asn Ser Tyr Glu Lys Thr Lys Asn Asn Glu Asn Asn Lys Phe Phe Asp
                85                  90                  95

Lys Lys Glu Leu Thr Met Ser Asn Val Lys Asn Val Ser Gln Thr Asn
            100                 105                 110

Phe Lys Ser Leu Leu Arg Asn Leu Gly Val Ser Glu Asn Ile Phe Leu
        115                 120                 125

Lys Glu Asn Lys Leu Asn Lys Glu Gly Lys Leu Ile Glu His Ile Ile
    130                 135                 140

Asn Asp Asp Asp Asp Lys Lys Lys Tyr Ile Lys Gly Gln Asp Glu Asn
145                 150                 155                 160

Arg Gln Glu Asp Leu Glu Glu Lys Ala Ala Lys Glu Thr Leu Gln Gly
                165                 170                 175

Gln Gln Ser Asp Leu Glu Gln Glu Arg Leu Ala Lys Glu Lys Leu Gln
            180                 185                 190

Glu Gln Gln Ser Asp Ser Glu Gln Glu Arg Leu Ala Lys Glu Lys Leu
        195                 200                 205

Gln Glu Gln Gln Ser Asp Leu Glu Gln Glu Arg Leu Ala Lys Glu Lys
    210                 215                 220

Leu Gln Glu Gln Gln Ser Asp Leu Glu Gln Glu Arg Leu Ala Lys Glu
225                 230                 235                 240

Lys Leu Gln Glu Gln Gln Ser Asp Leu Glu Gln Glu Arg Arg Ala Lys
                245                 250                 255

Glu Lys Leu Gln Glu Gln Gln Ser Asp Leu Glu Gln Glu Arg Arg Ala
            260                 265                 270

Lys Glu Lys Leu Gln Glu Gln Gln Ser Asp Leu Glu Gln Glu Arg Arg
        275                 280                 285

Ala Lys Glu Lys Leu Gln Glu Gln Gln Arg Asp Leu Glu Gln Arg Lys
    290                 295                 300

Ala Asp Thr Lys Lys Asn Leu Glu Arg Lys Lys Glu His Gly Asp Val
305                 310                 315                 320

Leu Ala Glu Asp Leu Tyr Gly Arg Leu Glu Ile Pro Ala Ile Glu Leu
                325                 330                 335

Pro Ser Glu Asn Glu Arg Gly Tyr Tyr Ile Pro His Gln Ser Ser Leu
            340                 345                 350

Pro Gln Asp Asn Arg Gly Asn Ser Arg Asp Ser Lys Glu Ile Ser Ile
        355                 360                 365

Ile Glu Lys Thr Asn Arg Glu Ser Ile Thr Thr Asn Val Glu Gly Arg
    370                 375                 380

Arg Asp Ile His Lys Gly His Leu Glu Glu Lys Lys Asp Gly Ser Ile
385                 390                 395                 400

Lys Pro Glu Gln Lys Glu Asp Lys Ser Ala Asp Ile Gln Asn His Thr
                405                 410                 415

Leu Glu Thr Val Asn Ile Ser Asp Val Asn Asp Phe Gln Ile Ser Lys
            420                 425                 430

Tyr Glu Asp Glu Ile Ser Ala Glu Tyr Asp Asp Ser Leu Ile Asp Glu
        435                 440                 445

Glu Glu Asp Asp Glu Asp Leu Asp Glu Phe Lys Pro Ile Val Gln Tyr
    450                 455                 460

Asp Asn Phe Gln Asp Glu Glu Asn Ile Gly Ile Tyr Lys Glu Leu Glu
465                 470                 475                 480

Asp Leu Ile Glu Lys Asn Glu Asn Leu Asp Asp Leu Asp Glu Gly Ile
```

-continued

```
            485                 490                 495

Glu Lys Ser Ser Glu Glu Leu Ser Glu Glu Lys Ile Lys Lys Gly Lys
            500                 505                 510

Lys Tyr Glu Lys Thr Lys Asp Asn Asn Phe Lys Pro Asn Asp Lys Ser
        515                 520                 525

Leu Tyr Asp Glu His Ile Lys Lys Tyr Lys Asn Asp Lys Gln Val Asn
    530                 535                 540

Lys Glu Lys Glu Lys Phe Ile Lys Ser Leu Phe His Ile Phe Asp Gly
545                 550                 555                 560

Asp Asn Glu Ile Leu Gln Ile Val Asp Glu Leu Ser Glu Asp Ile Thr
                565                 570                 575

Lys Tyr Phe Met Lys Leu
            580


<210> SEQ ID NO 17
<211> LENGTH: 1731
<212> TYPE: DNA
<213> ORGANISM: Artificial Sequence
<220> FEATURE:
<223> OTHER INFORMATION: Immunogen consensus nucleic acid sequence 9

<400> SEQUENCE: 17

atggactgga cctggattct gttcctggtg gccgctgcta caagagtgca cagcaaccac     60

ctgggcaacg tgaagtacct ggtgatcgtg ttcctgatct tcttcgacct gtttctggtg    120

aacggccggg acgtgcagaa caacatcgtg gacgagatca agtaccggga ggaagtgtgc    180

aacgacgagg tggacctgta cctgctgatg gactgcagcg gcagcatcag acggcacaac    240

tgggtgaacc acgccgtgcc cctggccatg aagctgatcc agcagctgaa cctgaacgag    300

aacgccatcc acctgtacgt gaacgacttc agcaacaacg ccaaagagat catccggctg    360

cacagcgacg ccagcaagaa caaagagaag gccctgatca tcatcaagag cctgctgagc    420

accaacctgc cctacggccg gaccaacctg tctgacgctc tgctgcaggt gcggaagcac    480

ctgaacgacc ggatcaaccg ggagaacgcc aaccagctgg tggtgatcct gaccgacggc    540

atccccgaca gcatccagga cagcctgaaa gagagccgga agctgaacga cagaggcgtg    600

aagatcgccg tgttcggcat cggccagggc atcaacgtgg ccttcaacag attcctggtg    660

ggctgtcacc ccagcgacgg caagtgcaac ctgtacgccg acagcgcctg ggagaacgtg    720

aagaatgtga tcggcccctt catgaaggcc gtgtgcgtgg aggtggagaa aaccgccagc    780

tgcggcgtgt gggatgagtg gagcccctgc agcgtgacct gtggcaaggg caccagaagc    840

cggaagcggg agatcctgca cgagggctgc accagcgagc tgcaggaaca gtgcgaagag    900

gaacggtgcc cccccaagag ggaacccctg gacgtgcccc acgagcccga ggacgaccag    960

cccagaccca gaggcgacaa cttcgccgtg gagaagcccg aggaaaacat catcgacaac   1020

aacccccagg aacccagccc caaccctgag gaaggcaagg gcgagaaccc caacggcttc   1080

gacctggacg agaaccccga gaatcccccc aaccccgaca tccccgagca ggaacccaac   1140

atccctgagg acagcgagaa agaggtgccc agcgacgtcc ccaagaatcc cgaggatgac   1200

cgggaagaga acttcgacat ccccaagaag cctgagaaca agcacgacaa ccagaacaac   1260

ctgcccaacg acaagagcga ccggtacatc ccctacagcc ccctgccccc caaggtgctg   1320

gacaacgagc ggaagcagag cgacccccag agccaggaca acaacggcaa ccggcacgtg   1380

cccaacagcg aggaccggga gacaagaccc cacggccgga acaacgagaa ccggtcctac   1440

aaccggaagt acaacgacac ccccaagcac cccgagcggg aggaacacga gaaacccgac   1500
```

-continued

```
aacaacaaga agaagggcgg cagcgacaac aagtacaaga ttgccggcgg aatcgctggc   1560

ggactggccc tgctggcttg tgccggcctg gcctacaagt ttgtggtgcc tggcgccgct   1620

acaccttatg ccggcgagcc tgcccccttt gacgagacac tgggcgaaga ggacaaggac   1680

ctggatgagc ccgagcagtt ccggctgccc gaagagaacg agtggaactg a            1731


<210> SEQ ID NO 18
<211> LENGTH: 576
<212> TYPE: PRT
<213> ORGANISM: Artificial Sequence
<220> FEATURE:
<223> OTHER INFORMATION: Immunogen consensus amino acid sequence 9

<400> SEQUENCE: 18

Met Asp Trp Thr Trp Ile Leu Phe Leu Val Ala Ala Ala Thr Arg Val
1               5                   10                  15

His Ser Asn His Leu Gly Asn Val Lys Tyr Leu Val Ile Val Phe Leu
            20                  25                  30

Ile Phe Phe Asp Leu Phe Leu Val Asn Gly Arg Asp Val Gln Asn Asn
        35                  40                  45

Ile Val Asp Glu Ile Lys Tyr Arg Glu Glu Val Cys Asn Asp Glu Val
    50                  55                  60

Asp Leu Tyr Leu Leu Met Asp Cys Ser Gly Ser Ile Arg Arg His Asn
65                  70                  75                  80

Trp Val Asn His Ala Val Pro Leu Ala Met Lys Leu Ile Gln Gln Leu
                85                  90                  95

Asn Leu Asn Glu Asn Ala Ile His Leu Tyr Val Asn Asp Phe Ser Asn
            100                 105                 110

Asn Ala Lys Glu Ile Ile Arg Leu His Ser Asp Ala Ser Lys Asn Lys
        115                 120                 125

Glu Lys Ala Leu Ile Ile Ile Lys Ser Leu Leu Ser Thr Asn Leu Pro
    130                 135                 140

Tyr Gly Arg Thr Asn Leu Ser Asp Ala Leu Leu Gln Val Arg Lys His
145                 150                 155                 160

Leu Asn Asp Arg Ile Asn Arg Glu Asn Ala Asn Gln Leu Val Val Ile
                165                 170                 175

Leu Thr Asp Gly Ile Pro Asp Ser Ile Gln Asp Ser Leu Lys Glu Ser
            180                 185                 190

Arg Lys Leu Asn Asp Arg Gly Val Lys Ile Ala Val Phe Gly Ile Gly
        195                 200                 205

Gln Gly Ile Asn Val Ala Phe Asn Arg Phe Leu Val Gly Cys His Pro
    210                 215                 220

Ser Asp Gly Lys Cys Asn Leu Tyr Ala Asp Ser Ala Trp Glu Asn Val
225                 230                 235                 240

Lys Asn Val Ile Gly Pro Phe Met Lys Ala Val Cys Val Glu Val Glu
                245                 250                 255

Lys Thr Ala Ser Cys Gly Val Trp Asp Glu Trp Ser Pro Cys Ser Val
            260                 265                 270

Thr Cys Gly Lys Gly Thr Arg Ser Arg Lys Arg Glu Ile Leu His Glu
        275                 280                 285

Gly Cys Thr Ser Glu Leu Gln Glu Gln Cys Glu Glu Glu Arg Cys Pro
    290                 295                 300

Pro Lys Arg Glu Pro Leu Asp Val Pro His Glu Pro Glu Asp Asp Gln
305                 310                 315                 320
```

-continued

```
Pro Arg Pro Arg Gly Asp Asn Phe Ala Val Glu Lys Pro Glu Glu Asn
                325                 330                 335

Ile Ile Asp Asn Asn Pro Gln Glu Pro Ser Pro Asn Pro Glu Glu Gly
            340                 345                 350

Lys Gly Glu Asn Pro Asn Gly Phe Asp Leu Asp Glu Asn Pro Glu Asn
        355                 360                 365

Pro Pro Asn Pro Asp Ile Pro Glu Gln Glu Pro Asn Ile Pro Glu Asp
    370                 375                 380

Ser Glu Lys Glu Val Pro Ser Asp Val Pro Lys Asn Pro Glu Asp Asp
385                 390                 395                 400

Arg Glu Glu Asn Phe Asp Ile Pro Lys Lys Pro Glu Asn Lys His Asp
                405                 410                 415

Asn Gln Asn Asn Leu Pro Asn Asp Lys Ser Asp Arg Tyr Ile Pro Tyr
            420                 425                 430

Ser Pro Leu Pro Pro Lys Val Leu Asp Asn Glu Arg Lys Gln Ser Asp
        435                 440                 445

Pro Gln Ser Gln Asp Asn Asn Gly Asn Arg His Val Pro Asn Ser Glu
    450                 455                 460

Asp Arg Glu Thr Arg Pro His Gly Arg Asn Asn Glu Asn Arg Ser Tyr
465                 470                 475                 480

Asn Arg Lys Tyr Asn Asp Thr Pro Lys His Pro Glu Arg Glu Glu His
                485                 490                 495

Glu Lys Pro Asp Asn Asn Lys Lys Lys Gly Gly Ser Asp Asn Lys Tyr
            500                 505                 510

Lys Ile Ala Gly Gly Ile Ala Gly Gly Leu Ala Leu Leu Ala Cys Ala
        515                 520                 525

Gly Leu Ala Tyr Lys Phe Val Val Pro Gly Ala Ala Thr Pro Tyr Ala
    530                 535                 540

Gly Glu Pro Ala Pro Phe Asp Glu Thr Leu Gly Glu Glu Asp Lys Asp
545                 550                 555                 560

Leu Asp Glu Pro Glu Gln Phe Arg Leu Pro Glu Glu Asn Glu Trp Asn
                565                 570                 575


<210> SEQ ID NO 19
<211> LENGTH: 600
<212> TYPE: DNA
<213> ORGANISM: Artificial Sequence
<220> FEATURE:
<223> OTHER INFORMATION: Immunogen consensus nucleic acid sequence 10

<400> SEQUENCE: 19

atggactgga cctggattct gttcctggtg gccgctgcca caagagtgca cagcaacgcc      60

ctgcggagac tgcccgtgat ctgcagcttc ctggtgtttc tggtgttcag caacgtgctg     120

tgcttccggg gcaacaacgg ccacaacagc agcagcagcc tgtacaacgg cagccagttc     180

atcgagcagc tgaacaacag cttcaccagc gcctttctgg aaagccagag catgaacaag     240

atcggcgacg acctggccga gacaatcagc aacgagctgg tgtccgtgct gcagaagaac     300

agccccacct tcctggaaag cagcttcgac atcaagagcg aagtgaagaa acacgccaag     360

agcatgctga aagaactgat caaagtgggc ctgcccagct tcgagaatct ggtcgccgag     420

aacgtgaagc cccccaaggt ggaccctgcc acatacggca tcatcgtgcc cgtgctgacc     480

agcctgttca acaaggtgga gacagccgtg ggcgccaagg tgtccgacga gatctggaac     540

tacaacagcc ccgacgtgtc cgagagcgag gaaagcctga gcgacgactt cttcgactga     600
```

<210> SEQ ID NO 20
<211> LENGTH: 199
<212> TYPE: PRT
<213> ORGANISM: Artificial Sequence
<220> FEATURE:
<223> OTHER INFORMATION: Immunogen consensus amino acid sequence 10

<400> SEQUENCE: 20

```
Met Asp Trp Thr Trp Ile Leu Phe Leu Val Ala Ala Ala Thr Arg Val
1               5                   10                  15

His Ser Asn Ala Leu Arg Arg Leu Pro Val Ile Cys Ser Phe Leu Val
            20                  25                  30

Phe Leu Val Phe Ser Asn Val Leu Cys Phe Arg Gly Asn Asn Gly His
        35                  40                  45

Asn Ser Ser Ser Ser Leu Tyr Asn Gly Ser Gln Phe Ile Glu Gln Leu
    50                  55                  60

Asn Asn Ser Phe Thr Ser Ala Phe Leu Glu Ser Gln Ser Met Asn Lys
65                  70                  75                  80

Ile Gly Asp Asp Leu Ala Glu Thr Ile Ser Asn Glu Leu Val Ser Val
                85                  90                  95

Leu Gln Lys Asn Ser Pro Thr Phe Leu Glu Ser Ser Phe Asp Ile Lys
            100                 105                 110

Ser Glu Val Lys Lys His Ala Lys Ser Met Leu Lys Glu Leu Ile Lys
        115                 120                 125

Val Gly Leu Pro Ser Phe Glu Asn Leu Val Ala Glu Asn Val Lys Pro
    130                 135                 140

Pro Lys Val Asp Pro Ala Thr Tyr Gly Ile Ile Val Pro Val Leu Thr
145                 150                 155                 160

Ser Leu Phe Asn Lys Val Glu Thr Ala Val Gly Ala Lys Val Ser Asp
                165                 170                 175

Glu Ile Trp Asn Tyr Asn Ser Pro Asp Val Ser Glu Ser Glu Glu Ser
            180                 185                 190

Leu Ser Asp Asp Phe Phe Asp
        195
```

<210> SEQ ID NO 21
<211> LENGTH: 1917
<212> TYPE: DNA
<213> ORGANISM: Artificial sequence
<220> FEATURE:
<223> OTHER INFORMATION: Immunogen consensus nucleic acid sequence 11

<400> SEQUENCE: 21

```
atggactgga catggattct gttcctggtg gctgctgcta ctagagtgca ttcaagaaaa      60

ctgtattgcg tgctgctgct gagcgccttc gagttcacct atatgatcaa cttcggaagg     120

ggccagaatt actgggagca cccctatcag aactctgacg tgtaccgacc tattaatgaa     180

caccgggagc atcccaagga gtacgaatat cctctgcacc aggaacatac atatcagcag     240

gaggacagcg gggaggatga aaacactctg cagcacgcct acccaatcga ccatgaagga     300

gctgagccag caccccagga gcagaatctg tttagctcca tcgaaattgt ggagcgcagt     360

aactacatgg gcaatccctg gaccgagtac atggccaagt atgatatcga ggaagtccac     420

gggtccggaa ttcgcgtgga cctgggcgaa gatgccgagg tcgctgggac acagtatcga     480

ctgccttccg gcaaatgccc agtgttcggc aaggggatca ttatcgagaa ctctaatacc     540

acatttctga cccccgtggc cacagggaac cagtacctga aggacggcgg attcgctttt     600

ccccctactg aacccctgat gtctcctatg accctggacg agatgaggca cttctacaag     660
```

```
gataacaaat acgtcaagaa tctggacgag ctgactctgt gctcacgcca tgctggaaac    720

atgatcccag acaacgataa gaacagcaac tacaagtatc ccgcagtgta cgacgataag    780

gacaagaaat gtcacatcct gtatattgcc gctcaggaaa acaatggccc ccggtactgc    840

aacaaagatg agtctaagag aaacagtatg ttctgtttca ggcctgcaaa agacatcagt    900

ttccagaact acacatatct gtcaaagaac gtggtcgata attgggagaa agtgtgcccc    960

agaaagaacc tgcagaatgc taagtttggg ctgtgggtcg acggaaactg cgaagatatc   1020

ccacacgtga atgagttccc cgcaattgac ctgtttgaat gtaacaagct ggtgttcgag   1080

ctgtccgcct ctgatcagcc taagcagtac gagcagcatc tgacagacta tgaaaagatc   1140

aaagagggct ttaagaacaa aaacgcatca atgatcaaga gcgccttcct gccaactggg   1200

gccttcaagg ccgataggta caaaagccac ggaaagggct acaactgggg aaactataat   1260

acagaaactc agaaatgcga gatcttcaat gtcaagccca cctgtctgat caacaattct   1320

agttacatcg ctactaccgc actgtctcat cctattgagg tggaaaacaa ttttccatgc   1380

agtctgtaca aagacgaaat catgaaggag attgaaaggg agagcaaacg catcaagctg   1440

aacgataatg acgatgaggg gaacaagaaa attatcgccc ctcgaatctt catttccgac   1500

gataaagact ctctgaagtg cccttgtgat ccagagatgg tcagtaattc aacctgtcgc   1560

ttctttgtct gcaagtgcgt ggaacggaga gccgaggtga catccaacaa tgaggtggtc   1620

gtgaaagagg aatacaagga cgaatatgcc gatatcccag agcacaagcc cacttacgac   1680

aagatgaaaa ttatcattgc ttcaagcgca gccgtcgccg tgctggctac cattctgatg   1740

gtgtacctgt ataagagaaa aggaaacgcc gaaaaatacg acaagatgga tgagcctcag   1800

gattatggca aaagcaactc ccggaatgac gaaatgctgg accccgaggc tagcttttgg   1860

ggcgaggaaa agagagcatc ccataccacc cccgtcctga tggaaaagcc ttactat      1917
```

```
<210> SEQ ID NO 22
<211> LENGTH: 639
<212> TYPE: PRT
<213> ORGANISM: Artificial Sequence
<220> FEATURE:
<223> OTHER INFORMATION: Immunogen consensus amino acid sequence 11

<400> SEQUENCE: 22

Met Asp Trp Thr Trp Ile Leu Phe Leu Val Ala Ala Ala Thr Arg Val
1               5                   10                  15

His Ser Arg Lys Leu Tyr Cys Val Leu Leu Leu Ser Ala Phe Glu Phe
            20                  25                  30

Thr Tyr Met Ile Asn Phe Gly Arg Gly Gln Asn Tyr Trp Glu His Pro
        35                  40                  45

Tyr Gln Asn Ser Asp Val Tyr Arg Pro Ile Asn Glu His Arg Glu His
    50                  55                  60

Pro Lys Glu Tyr Glu Tyr Pro Leu His Gln Glu His Thr Tyr Gln Gln
65                  70                  75                  80

Glu Asp Ser Gly Glu Asp Glu Asn Thr Leu Gln His Ala Tyr Pro Ile
                85                  90                  95

Asp His Glu Gly Ala Glu Pro Ala Pro Gln Glu Gln Asn Leu Phe Ser
            100                 105                 110

Ser Ile Glu Ile Val Glu Arg Ser Asn Tyr Met Gly Asn Pro Trp Thr
        115                 120                 125

Glu Tyr Met Ala Lys Tyr Asp Ile Glu Glu Val His Gly Ser Gly Ile
    130                 135                 140
```

-continued

```
Arg Val Asp Leu Gly Glu Asp Ala Glu Val Ala Gly Thr Gln Tyr Arg
145                 150                 155                 160

Leu Pro Ser Gly Lys Cys Pro Val Phe Gly Lys Gly Ile Ile Ile Glu
                165                 170                 175

Asn Ser Asn Thr Thr Phe Leu Thr Pro Val Ala Thr Gly Asn Gln Tyr
            180                 185                 190

Leu Lys Asp Gly Gly Phe Ala Phe Pro Pro Thr Glu Pro Leu Met Ser
        195                 200                 205

Pro Met Thr Leu Asp Glu Met Arg His Phe Tyr Lys Asp Asn Lys Tyr
    210                 215                 220

Val Lys Asn Leu Asp Glu Leu Thr Leu Cys Ser Arg His Ala Gly Asn
225                 230                 235                 240

Met Ile Pro Asp Asn Asp Lys Asn Ser Asn Tyr Lys Tyr Pro Ala Val
                245                 250                 255

Tyr Asp Asp Lys Asp Lys Lys Cys His Ile Leu Tyr Ile Ala Ala Gln
            260                 265                 270

Glu Asn Asn Gly Pro Arg Tyr Cys Asn Lys Asp Glu Ser Lys Arg Asn
        275                 280                 285

Ser Met Phe Cys Phe Arg Pro Ala Lys Asp Ile Ser Phe Gln Asn Tyr
    290                 295                 300

Thr Tyr Leu Ser Lys Asn Val Val Asp Asn Trp Glu Lys Val Cys Pro
305                 310                 315                 320

Arg Lys Asn Leu Gln Asn Ala Lys Phe Gly Leu Trp Val Asp Gly Asn
                325                 330                 335

Cys Glu Asp Ile Pro His Val Asn Glu Phe Pro Ala Ile Asp Leu Phe
            340                 345                 350

Glu Cys Asn Lys Leu Val Phe Glu Leu Ser Ala Ser Asp Gln Pro Lys
        355                 360                 365

Gln Tyr Glu Gln His Leu Thr Asp Tyr Glu Lys Ile Lys Glu Gly Phe
    370                 375                 380

Lys Asn Lys Asn Ala Ser Met Ile Lys Ser Ala Phe Leu Pro Thr Gly
385                 390                 395                 400

Ala Phe Lys Ala Asp Arg Tyr Lys Ser His Gly Lys Gly Tyr Asn Trp
                405                 410                 415

Gly Asn Tyr Asn Thr Glu Thr Gln Lys Cys Glu Ile Phe Asn Val Lys
            420                 425                 430

Pro Thr Cys Leu Ile Asn Asn Ser Ser Tyr Ile Ala Thr Thr Ala Leu
        435                 440                 445

Ser His Pro Ile Glu Val Glu Asn Asn Phe Pro Cys Ser Leu Tyr Lys
    450                 455                 460

Asp Glu Ile Met Lys Glu Ile Glu Arg Glu Ser Lys Arg Ile Lys Leu
465                 470                 475                 480

Asn Asp Asn Asp Asp Glu Gly Asn Lys Lys Ile Ile Ala Pro Arg Ile
                485                 490                 495

Phe Ile Ser Asp Asp Lys Asp Ser Leu Lys Cys Pro Cys Asp Pro Glu
            500                 505                 510

Met Val Ser Asn Ser Thr Cys Arg Phe Phe Val Cys Lys Cys Val Glu
        515                 520                 525

Arg Arg Ala Glu Val Thr Ser Asn Asn Glu Val Val Val Lys Glu Glu
    530                 535                 540

Tyr Lys Asp Glu Tyr Ala Asp Ile Pro Glu His Lys Pro Thr Tyr Asp
545                 550                 555                 560
```

-continued

```
Lys Met Lys Ile Ile Ile Ala Ser Ser Ala Ala Val Ala Val Leu Ala
                565                 570                 575

Thr Ile Leu Met Val Tyr Leu Tyr Lys Arg Lys Gly Asn Ala Glu Lys
            580                 585                 590

Tyr Asp Lys Met Asp Glu Pro Gln Asp Tyr Gly Lys Ser Asn Ser Arg
        595                 600                 605

Asn Asp Glu Met Leu Asp Pro Glu Ala Ser Phe Trp Gly Glu Glu Lys
    610                 615                 620

Arg Ala Ser His Thr Thr Pro Val Leu Met Glu Lys Pro Tyr Tyr
625                 630                 635


<210> SEQ ID NO 23
<211> LENGTH: 1134
<212> TYPE: DNA
<213> ORGANISM: Artificial Sequence
<220> FEATURE:
<223> OTHER INFORMATION: Immunogen consensus nucleic acid sequence 12

<400> SEQUENCE: 23

atggactgga cctggattct gttcctggtg gccgctgcca cacgggtgca cagcatgcgg      60

aagctggcta tcctgagcgt gtccagcttc ctgttcgtgg aggccctgtt ccaagagtac     120

cagtgctacg gcagcagcag caacacaaga gtgctgaacg agctgaacta cgacaacgcc     180

ggcaccaacc tgtacaacga gctggaaatg aactactacg gcaagcagga aaactggtac     240

agcctgaaga agaacagccg gtccctgggc gagaacgacg acggcaacaa caacaacggc     300

gacaacggca gagagggcaa ggacgaggac aagcgggatg gcaacaacga ggacaacgag     360

aagctgcgga agcccaagca caagaagctg aagcagcccg gcgacggcaa ccccgacccc     420

aacgccaacc ccaacgtgga ccccaatgcc aatcctaatg tcgatcccaa cgctaaccca     480

aatgtcgacc ctaacgcaaa tcctaacgcc aatcccaatg caaaccctaa tgccaaccca     540

aatgctaatc caaacgcaaa ccccaatgct aaccccaacg ctaaccctaa tgcaaatcca     600

aatgccaacc ccaacgccaa cccaaacgcc aatcccaacg ctaatcctaa cgctaacccc     660

aacgccaatc ctaacgccaa cccaaacgct aacccaaatg ccaaccccaa tgcaaatcct     720

aatgctaatc ctaacgctaa tccaaatgca aatccaaaca agaacaacca gggcaacggc     780

cagggccaca acatgcccaa cgaccccaac cggaacgtgg acgagaatgc caatgccaac     840

aacgccgtga agaacaacaa caatgaggaa cccagcgaca agcacatcga gcagtacctc     900

aagaagatcc agaacagcct gagcaccgag tggagcccct gtagcgtgac ctgcggcaac     960

ggcatccaag tccggatcaa gcccggcagc gccaacaagc ccaaggacga gctggattac    1020

gagaacgaca tcgagaagaa aatctgcaag atggaaaagt gcagcagcgt gttcaacgtg    1080

gtcaacagca gcatcggcct gatcatggtg ctgagctttc tgttcctcaa ctga          1134


<210> SEQ ID NO 24
<211> LENGTH: 377
<212> TYPE: PRT
<213> ORGANISM: Artificial Sequence
<220> FEATURE:
<223> OTHER INFORMATION: Immunogen consensus amino acid sequence 12

<400> SEQUENCE: 24

Met Asp Trp Thr Trp Ile Leu Phe Leu Val Ala Ala Ala Thr Arg Val
1               5                   10                  15

His Ser Met Arg Lys Leu Ala Ile Leu Ser Val Ser Ser Phe Leu Phe
            20                  25                  30
```

```
Val Glu Ala Leu Phe Gln Glu Tyr Gln Cys Tyr Gly Ser Ser Ser Asn
        35                  40                  45

Thr Arg Val Leu Asn Glu Leu Asn Tyr Asp Asn Ala Gly Thr Asn Leu
    50                  55                  60

Tyr Asn Glu Leu Glu Met Asn Tyr Tyr Gly Lys Gln Glu Asn Trp Tyr
65                  70                  75                  80

Ser Leu Lys Lys Asn Ser Arg Ser Leu Gly Glu Asn Asp Asp Gly Asn
                85                  90                  95

Asn Asn Asn Gly Asp Asn Gly Arg Glu Gly Lys Asp Glu Asp Lys Arg
            100                 105                 110

Asp Gly Asn Asn Glu Asp Asn Glu Lys Leu Arg Lys Pro Lys His Lys
        115                 120                 125

Lys Leu Lys Gln Pro Gly Asp Gly Asn Pro Asp Pro Asn Ala Asn Pro
    130                 135                 140

Asn Val Asp Pro Asn Ala Asn Pro Asn Val Asp Pro Asn Ala Asn Pro
145                 150                 155                 160

Asn Val Asp Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Ala Asn Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Lys Asn Asn
                245                 250                 255

Gln Gly Asn Gly Gln Gly His Asn Met Pro Asn Asp Pro Asn Arg Asn
            260                 265                 270

Val Asp Glu Asn Ala Asn Ala Asn Asn Ala Val Lys Asn Asn Asn Asn
        275                 280                 285

Glu Glu Pro Ser Asp Lys His Ile Glu Gln Tyr Leu Lys Lys Ile Gln
    290                 295                 300

Asn Ser Leu Ser Thr Glu Trp Ser Pro Cys Ser Val Thr Cys Gly Asn
305                 310                 315                 320

Gly Ile Gln Val Arg Ile Lys Pro Gly Ser Ala Asn Lys Pro Lys Asp
                325                 330                 335

Glu Leu Asp Tyr Glu Asn Asp Ile Glu Lys Lys Ile Cys Lys Met Glu
            340                 345                 350

Lys Cys Ser Ser Val Phe Asn Val Val Asn Ser Ser Ile Gly Leu Ile
        355                 360                 365

Met Val Leu Ser Phe Leu Phe Leu Asn
    370                 375
```

<210> SEQ ID NO 25
<211> LENGTH: 1317
<212> TYPE: DNA
<213> ORGANISM: Artificial Sequence
<220> FEATURE:
<223> OTHER INFORMATION: Immunogen consensus nucleic acid sequence 13

<400> SEQUENCE: 25

```
atggactgga cctggattct gttcctggtg gccgctgcca cacgggtgca cagcatgcgg      60

aagctggcta tcctgagcgt gtccagcttc ctgttcgtgg aggccctgtt ccaagagtac     120
```

-continued

```
cagtgctacg gcagcagcag caacacaaga gtgctgaacg agctgaacta cgacaacgcc    180

ggcaccaacc tgtacaacga gctggaaatg aactactacg gcaagcagga aaactggtac    240

agcctgaaga agaacagccg gtccctgggc gagaacgacg acggcaacaa caacaacggc    300

gacaacggca gagagggcaa ggacgaggac aagcgggatg gcaacaacga ggacaacgag    360

aagctgcgga agcccaagca caagaagctg aagcagcccg gcgacggcaa ccccgacccc    420

aacgccaacc ccaacgtgga ccccaatgcc aatcctaatg tcgatcccaa cgctaaccca    480

aatgtcgacc ctaacgcaaa tcctaacgcc aatcccaatg caaaccctaa tgccaaccca    540

aatgctaatc caaacgcaaa ccccaatgct aaccccaacg ctaaccctaa tgcaaatcca    600

aatgccaacc ccaacgccaa cccaaacgcc aatcccaacg ctaatcctaa cgctaacccc    660

aacgccaatc ctaacgccaa cccaaacgct aacccaaatg ccaaccccaa tgcaaatcct    720

aatgctaatc ctaacgctaa tccaaatgca aatccaaacg ctaatcctaa tgccaaccct    780

aacgcaaacc ccaacgcaaa tccaaatgct aacccaaatg caaatcccaa cgccaatcca    840

aacgcaaatc caaatgccaa tcctaatgca aaccctaatg caaatcccaa tgctaatcct    900

aatgctaatc caaacaagaa caaccagggc aacggccagg gccacaacat gcccaacgac    960

cccaaccgga acgtggacga gaatgccaat gccaacaacg ccgtgaagaa caacaacaat   1020

gaggaaccca gcgacaagca catcgagcag tacctcaaga agatccagaa cagcctgagc   1080

accgagtgga gcccctgtag cgtgacctgc ggcaacggca tccaagtccg gatcaagccc   1140

ggcagcgcca acaagcccaa ggacgagctg gattacgaga acgacatcga gaagaaaatc   1200

tgcaagatgg aaaagtgcag cagcgtgttc aacgtggtca acagcagcat cggcctgatc   1260

atggtgctga gctttctgtt cctcaactac ccctacgacg tgcccgacta cgcctga      1317
```

<210> SEQ ID NO 26
<211> LENGTH: 438
<212> TYPE: PRT
<213> ORGANISM: Artificial Sequence
<220> FEATURE:
<223> OTHER INFORMATION: Immunogen consensus amino acid sequence 13

<400> SEQUENCE: 26

```
Met Asp Trp Thr Trp Ile Leu Phe Leu Val Ala Ala Ala Thr Arg Val
1               5                   10                  15

His Ser Met Arg Lys Leu Ala Ile Leu Ser Val Ser Ser Phe Leu Phe
            20                  25                  30

Val Glu Ala Leu Phe Gln Glu Tyr Gln Cys Tyr Gly Ser Ser Ser Asn
        35                  40                  45

Thr Arg Val Leu Asn Glu Leu Asn Tyr Asp Asn Ala Gly Thr Asn Leu
    50                  55                  60

Tyr Asn Glu Leu Glu Met Asn Tyr Tyr Gly Lys Gln Glu Asn Trp Tyr
65                  70                  75                  80

Ser Leu Lys Lys Asn Ser Arg Ser Leu Gly Glu Asn Asp Asp Gly Asn
                85                  90                  95

Asn Asn Asn Gly Asp Asn Gly Arg Glu Gly Lys Asp Glu Asp Lys Arg
            100                 105                 110

Asp Gly Asn Asn Glu Asp Asn Glu Lys Leu Arg Lys Pro Lys His Lys
        115                 120                 125

Lys Leu Lys Gln Pro Gly Asp Gly Asn Pro Asp Pro Asn Ala Asn Pro
    130                 135                 140

Asn Val Asp Pro Asn Ala Asn Pro Asn Val Asp Pro Asn Ala Asn Pro
```

```
145                 150                 155                 160

Asn Val Asp Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Ala Asn Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Ala Asn Pro Asn Ala Asn Pro Asn Ala Asn Pro Asn Ala Asn Pro
        275                 280                 285

Asn Ala Asn Pro Asn Ala Asn Pro Asn Ala Asn Pro Asn Ala Asn Pro
    290                 295                 300

Asn Lys Asn Asn Gln Gly Asn Gly Gln Gly His Asn Met Pro Asn Asp
305                 310                 315                 320

Pro Asn Arg Asn Val Asp Glu Asn Ala Asn Ala Asn Asn Ala Val Lys
                325                 330                 335

Asn Asn Asn Asn Glu Glu Pro Ser Asp Lys His Ile Glu Gln Tyr Leu
            340                 345                 350

Lys Lys Ile Gln Asn Ser Leu Ser Thr Glu Trp Ser Pro Cys Ser Val
        355                 360                 365

Thr Cys Gly Asn Gly Ile Gln Val Arg Ile Lys Pro Gly Ser Ala Asn
    370                 375                 380

Lys Pro Lys Asp Glu Leu Asp Tyr Glu Asn Asp Ile Glu Lys Lys Ile
385                 390                 395                 400

Cys Lys Met Glu Lys Cys Ser Ser Val Phe Asn Val Val Asn Ser Ser
                405                 410                 415

Ile Gly Leu Ile Met Val Leu Ser Phe Leu Phe Leu Asn Tyr Pro Tyr
            420                 425                 430

Asp Val Pro Asp Tyr Ala
        435


<210> SEQ ID NO 27
<211> LENGTH: 1779
<212> TYPE: DNA
<213> ORGANISM: Artificial Sequence
<220> FEATURE:
<223> OTHER INFORMATION: Immunogen consensus nucleic acid sequence 14

<400> SEQUENCE: 27

atggactgga cctggattct gttcctcgtc gcagctgcca ccagagtgca cagcaagcac      60

atcctgtaca tcagcttcta cttcatcctg gtgaacctgc tgatcttcca catcaacggc     120

aagatcatca agaacagcga gaaggacgag atcatcaaaa gcaacctgcg gagcggcagc     180

agcaacagcc ggaaccggat caacgaggaa aagcacgaga agaaacacgt gctgagccac     240

aacagctacg aaaagaccaa gaacaatgag aacaacaagt tcttcgacaa ggacaaagaa     300

ctgaccatga gcaacgtgaa gaacgtgtcc cagaccaact tcaagagcct gctgcggaac     360

ctgggcgtga gcgagaacat cttcctgaaa gagaacaagc tgaacaaaga gggcaagctg     420
```

```
atcgagcaca tcatcaacga cgacgacgat aagaagaagt acatcaaggg ccaggacgag    480

aaccggcagg aagatctgga agagaaggcc gccaaagaga cactgcaggg ccagcagagc    540

gacctggaac aggaacggct ggccaaagaa aagctgcagg aacagcagtc cgacagcgag    600

caggaaagac tggctaaaga gaaactccaa gagcagcagt ctgacttgga gcaggaacgc    660

ctcgcaaaag agaagttgca agagcaacag tccgatctgg aacaagagcg cctcgctaaa    720

gaaaaacttc aggaacaaca gagcgatttg gagcaagagc ggagagccaa agagaaattg    780

caggaacaac aatctgacct cgaacaggaa agaagggcca aagagaagct tcaagaacaa    840

caaagtgacc ttgagcaaga gaggcgggct aaagaaaaat tgcaagaaca gcagcgggat    900

ctcgaacagc ggaaggccga caccaagaag aacctggaac ggaagaaaga acacggcgac    960

gtgctggccg aggacctgta cggcagactg gaaatccccg ccatcgagct gcccagcgag   1020

aacgagcggg gctactacat cccccaccag agcagcctgc cccaggacaa ccggggcaac   1080

agcagagaca gcaaagagat cagcatcatc gagaaaacaa accgggagag catcaccacc   1140

aacgtggagg gcagacggga catccacaag ggccacctgg aagaaaagaa ggacggcagc   1200

atcaagcccg agcagaaaga ggacaagagc gccgacatcc agaaccacac cctggaaacc   1260

gtgaacatca gcgacgtgaa cgacttccag atcagcaagt acgaggatga gatcagcgcc   1320

gagtacgacg acagcctgat cgacgaggaa gaggacgacg aggacctgga cgagttcaag   1380

cccatcgtgc agtacgacaa cttccaggac gaggaaaaca tcggcatcta caaagagctg   1440

gaagatctga tcgagaagaa cgagaacctg gatgatctgg acgagggcat cgagaagtcc   1500

agcgaggaac tgagcgagga aaagatcaag aagggcaaga agtacgagaa aactaaggac   1560

aacaacttca agcccaacga caagagcctg tacgatgagc acatcaagaa gtacaaaaac   1620

gacaaacagg tgaacaaaga aaaagagaag ttcatcaagt ccctgttcca catcttcgac   1680

ggcgacaacg agatcctgca gatcgtggat gagctgtccg aggacatcac caagtacttc   1740

atgaagctgt accccctacga cgtgcccgac tacgcctga                          1779
```

```
<210> SEQ ID NO 28
<211> LENGTH: 591
<212> TYPE: PRT
<213> ORGANISM: Artificial Sequence
<220> FEATURE:
<223> OTHER INFORMATION: Immunogen consensus amino acid sequence 14

<400> SEQUENCE: 28

Met Asp Trp Thr Trp Ile Leu Phe Leu Val Ala Ala Ala Thr Arg Val
1               5                   10                  15

His Ser Lys His Ile Leu Tyr Ile Ser Phe Tyr Phe Ile Leu Val Asn
            20                  25                  30

Leu Leu Ile Phe His Ile Asn Gly Lys Ile Ile Lys Asn Ser Glu Lys
        35                  40                  45

Asp Glu Ile Ile Lys Ser Asn Leu Arg Ser Gly Ser Ser Asn Ser Arg
    50                  55                  60

Asn Arg Ile Asn Glu Glu Lys His Glu Lys Lys His Val Leu Ser His
65                  70                  75                  80

Asn Ser Tyr Glu Lys Thr Lys Asn Asn Glu Asn Asn Lys Phe Phe Asp
                85                  90                  95

Lys Lys Glu Leu Thr Met Ser Asn Val Lys Asn Val Ser Gln Thr Asn
            100                 105                 110

Phe Lys Ser Leu Leu Arg Asn Leu Gly Val Ser Glu Asn Ile Phe Leu
```

-continued

```
        115                 120                 125

Lys Glu Asn Lys Leu Asn Lys Glu Gly Lys Leu Ile Glu His Ile Ile
    130                 135                 140

Asn Asp Asp Asp Asp Lys Lys Lys Tyr Ile Lys Gly Gln Asp Glu Asn
145                 150                 155                 160

Arg Gln Glu Asp Leu Glu Glu Lys Ala Ala Lys Glu Thr Leu Gln Gly
                165                 170                 175

Gln Gln Ser Asp Leu Glu Gln Glu Arg Leu Ala Lys Glu Lys Leu Gln
            180                 185                 190

Glu Gln Gln Ser Asp Ser Glu Gln Glu Arg Leu Ala Lys Glu Lys Leu
        195                 200                 205

Gln Glu Gln Gln Ser Asp Leu Glu Gln Glu Arg Leu Ala Lys Glu Lys
    210                 215                 220

Leu Gln Glu Gln Gln Ser Asp Leu Glu Gln Glu Arg Leu Ala Lys Glu
225                 230                 235                 240

Lys Leu Gln Glu Gln Gln Ser Asp Leu Glu Gln Glu Arg Arg Ala Lys
                245                 250                 255

Glu Lys Leu Gln Glu Gln Gln Ser Asp Leu Glu Gln Glu Arg Arg Ala
            260                 265                 270

Lys Glu Lys Leu Gln Glu Gln Gln Ser Asp Leu Glu Gln Glu Arg Arg
        275                 280                 285

Ala Lys Glu Lys Leu Gln Glu Gln Gln Arg Asp Leu Glu Gln Arg Lys
    290                 295                 300

Ala Asp Thr Lys Lys Asn Leu Glu Arg Lys Lys Glu His Gly Asp Val
305                 310                 315                 320

Leu Ala Glu Asp Leu Tyr Gly Arg Leu Glu Ile Pro Ala Ile Glu Leu
                325                 330                 335

Pro Ser Glu Asn Glu Arg Gly Tyr Tyr Ile Pro His Gln Ser Ser Leu
            340                 345                 350

Pro Gln Asp Asn Arg Gly Asn Ser Arg Asp Ser Lys Glu Ile Ser Ile
        355                 360                 365

Ile Glu Lys Thr Asn Arg Glu Ser Ile Thr Thr Asn Val Glu Gly Arg
    370                 375                 380

Arg Asp Ile His Lys Gly His Leu Glu Glu Lys Lys Asp Gly Ser Ile
385                 390                 395                 400

Lys Pro Glu Gln Lys Glu Asp Lys Ser Ala Asp Ile Gln Asn His Thr
                405                 410                 415

Leu Glu Thr Val Asn Ile Ser Asp Val Asn Asp Phe Gln Ile Ser Lys
            420                 425                 430

Tyr Glu Asp Glu Ile Ser Ala Glu Tyr Asp Asp Ser Leu Ile Asp Glu
        435                 440                 445

Glu Glu Asp Asp Glu Asp Leu Asp Glu Phe Lys Pro Ile Val Gln Tyr
    450                 455                 460

Asp Asn Phe Gln Asp Glu Glu Asn Ile Gly Ile Tyr Lys Glu Leu Glu
465                 470                 475                 480

Asp Leu Ile Glu Lys Asn Glu Asn Leu Asp Asp Leu Asp Glu Gly Ile
                485                 490                 495

Glu Lys Ser Ser Glu Glu Leu Ser Glu Glu Lys Ile Lys Lys Gly Lys
            500                 505                 510

Lys Tyr Glu Lys Thr Lys Asp Asn Asn Phe Lys Pro Asn Asp Lys Ser
        515                 520                 525

Leu Tyr Asp Glu His Ile Lys Lys Tyr Lys Asn Asp Lys Gln Val Asn
    530                 535                 540
```

-continued

```
Lys Glu Lys Glu Lys Phe Ile Lys Ser Leu Phe His Ile Phe Asp Gly
545                 550                 555                 560

Asp Asn Glu Ile Leu Gln Ile Val Asp Glu Leu Ser Glu Asp Ile Thr
                565                 570                 575

Lys Tyr Phe Met Lys Leu Tyr Pro Tyr Asp Val Pro Asp Tyr Ala
            580                 585                 590
```

<210> SEQ ID NO 29
<211> LENGTH: 1758
<212> TYPE: DNA
<213> ORGANISM: Artificial Sequence
<220> FEATURE:
<223> OTHER INFORMATION: Immunogen consensus nucleic acid sequence 15

<400> SEQUENCE: 29

```
atggactgga cctggattct gttcctggtg gccgctgcta caagagtgca cagcaaccac     60

ctgggcaacg tgaagtacct ggtgatcgtg ttcctgatct tcttcgacct gtttctggtg    120

aacggccggg acgtgcagaa caacatcgtg gacgagatca agtaccggga ggaagtgtgc    180

aacgacgagg tggacctgta cctgctgatg gactgcagcg gcagcatcag acggcacaac    240

tgggtgaacc acgccgtgcc cctggccatg aagctgatcc agcagctgaa cctgaacgag    300

aacgccatcc acctgtacgt gaacgacttc agcaacaacg ccaaagagat catccggctg    360

cacagcgacg ccagcaagaa caaagagaag gccctgatca tcatcaagag cctgctgagc    420

accaacctgc cctacggccg gaccaacctg tctgacgctc tgctgcaggt gcggaagcac    480

ctgaacgacc ggatcaaccg ggagaacgcc aaccagctgg tggtgatcct gaccgacggc    540

atccccgaca gcatccagga cagcctgaaa gagagccgga agctgaacga cagaggcgtg    600

aagatcgccg tgttcggcat cggccagggc atcaacgtgg ccttcaacag attcctggtg    660

ggctgtcacc ccagcgacgg caagtgcaac ctgtacgccg acagcgcctg ggagaacgtg    720

aagaatgtga tcggcccctt catgaaggcc gtgtgcgtgg aggtggagaa aaccgccagc    780

tgcggcgtgt gggatgagtg gagcccctgc agcgtgacct gtggcaaggg caccagaagc    840

cggaagcggg agatcctgca cgagggctgc accagcgagc tgcaggaaca gtgcgaagag    900

gaacggtgcc cccccaagag ggaacccctg gacgtgcccc acgagcccga ggacgaccag    960

cccagaccca gaggcgacaa cttcgccgtg gagaagcccg aggaaaacat catcgacaac   1020

aacccccagg aacccagccc caaccctgag gaaggcaagg gcgagaaccc caacggcttc   1080

gacctggacg agaaccccga gaatcccccc aaccccgaca tccccgagca ggaacccaac   1140

atccctgagg acagcgagaa agaggtgccc agcgacgtcc ccaagaatcc cgaggatgac   1200

cgggaagaga acttcgacat ccccaagaag cctgagaaca agcacgacaa ccagaacaac   1260

ctgcccaacg acaagagcga ccggtacatc ccctacagcc ccctgccccc caaggtgctg   1320

gacaacgagc ggaagcagag cgacccccag agccaggaca acaacggcaa ccggcacgtg   1380

cccaacagcg aggaccggga gacaagaccc cacggccgga acaacgagaa ccggtcctac   1440

aaccggaagt acaacgacac ccccaagcac cccgagcggg aggaacacga gaaacccgac   1500

aacaacaaga agaagggcgg cagcgacaac aagtacaaga ttgccggcgg aatcgctggc   1560

ggactggccc tgctggcttg tgccggcctg gcctacaagt ttgtggtgcc tggcgccgct   1620

acaccttatg ccggcgagcc tgccccctttt gacgagacac tgggcgaaga ggacaaggac   1680

ctggatgagc ccgagcagtt ccggctgccc gaagagaacg agtggaacta cccctacgac   1740

gtgcccgact acgcctga                                                 1758
```

<210> SEQ ID NO 30
<211> LENGTH: 585
<212> TYPE: PRT
<213> ORGANISM: Artificial Sequence
<220> FEATURE:
<223> OTHER INFORMATION: Immunogen consensus amino acid sequence 15

<400> SEQUENCE: 30

```
Met Asp Trp Thr Trp Ile Leu Phe Leu Val Ala Ala Ala Thr Arg Val
1               5                   10                  15

His Ser Asn His Leu Gly Asn Val Lys Tyr Leu Val Ile Val Phe Leu
            20                  25                  30

Ile Phe Phe Asp Leu Phe Leu Val Asn Gly Arg Asp Val Gln Asn Asn
        35                  40                  45

Ile Val Asp Glu Ile Lys Tyr Arg Glu Glu Val Cys Asn Asp Glu Val
    50                  55                  60

Asp Leu Tyr Leu Leu Met Asp Cys Ser Gly Ser Ile Arg Arg His Asn
65                  70                  75                  80

Trp Val Asn His Ala Val Pro Leu Ala Met Lys Leu Ile Gln Gln Leu
                85                  90                  95

Asn Leu Asn Glu Asn Ala Ile His Leu Tyr Val Asn Asp Phe Ser Asn
            100                 105                 110

Asn Ala Lys Glu Ile Ile Arg Leu His Ser Asp Ala Ser Lys Asn Lys
        115                 120                 125

Glu Lys Ala Leu Ile Ile Ile Lys Ser Leu Leu Ser Thr Asn Leu Pro
    130                 135                 140

Tyr Gly Arg Thr Asn Leu Ser Asp Ala Leu Leu Gln Val Arg Lys His
145                 150                 155                 160

Leu Asn Asp Arg Ile Asn Arg Glu Asn Ala Asn Gln Leu Val Val Ile
                165                 170                 175

Leu Thr Asp Gly Ile Pro Asp Ser Ile Gln Asp Ser Leu Lys Glu Ser
            180                 185                 190

Arg Lys Leu Asn Asp Arg Gly Val Lys Ile Ala Val Phe Gly Ile Gly
        195                 200                 205

Gln Gly Ile Asn Val Ala Phe Asn Arg Phe Leu Val Gly Cys His Pro
    210                 215                 220

Ser Asp Gly Lys Cys Asn Leu Tyr Ala Asp Ser Ala Trp Glu Asn Val
225                 230                 235                 240

Lys Asn Val Ile Gly Pro Phe Met Lys Ala Val Cys Val Glu Val Glu
                245                 250                 255

Lys Thr Ala Ser Cys Gly Val Trp Asp Glu Trp Ser Pro Cys Ser Val
            260                 265                 270

Thr Cys Gly Lys Gly Thr Arg Ser Arg Lys Arg Glu Ile Leu His Glu
        275                 280                 285

Gly Cys Thr Ser Glu Leu Gln Glu Gln Cys Glu Glu Glu Arg Cys Pro
    290                 295                 300

Pro Lys Arg Glu Pro Leu Asp Val Pro His Glu Pro Glu Asp Asp Gln
305                 310                 315                 320

Pro Arg Pro Arg Gly Asp Asn Phe Ala Val Glu Lys Pro Glu Glu Asn
                325                 330                 335

Ile Ile Asp Asn Asn Pro Gln Glu Pro Ser Pro Asn Pro Glu Glu Gly
            340                 345                 350

Lys Gly Glu Asn Pro Asn Gly Phe Asp Leu Asp Glu Asn Pro Glu Asn
        355                 360                 365
```

```
Pro Pro Asn Pro Asp Ile Pro Glu Gln Glu Pro Asn Ile Pro Glu Asp
    370                 375                 380

Ser Glu Lys Glu Val Pro Ser Asp Val Pro Lys Asn Pro Glu Asp Asp
385                 390                 395                 400

Arg Glu Glu Asn Phe Asp Ile Pro Lys Lys Pro Glu Asn Lys His Asp
                405                 410                 415

Asn Gln Asn Asn Leu Pro Asn Asp Lys Ser Asp Arg Tyr Ile Pro Tyr
            420                 425                 430

Ser Pro Leu Pro Pro Lys Val Leu Asp Asn Glu Arg Lys Gln Ser Asp
        435                 440                 445

Pro Gln Ser Gln Asp Asn Asn Gly Asn Arg His Val Pro Asn Ser Glu
    450                 455                 460

Asp Arg Glu Thr Arg Pro His Gly Arg Asn Asn Glu Asn Arg Ser Tyr
465                 470                 475                 480

Asn Arg Lys Tyr Asn Asp Thr Pro Lys His Pro Glu Arg Glu Glu His
                485                 490                 495

Glu Lys Pro Asp Asn Asn Lys Lys Lys Gly Gly Ser Asp Asn Lys Tyr
            500                 505                 510

Lys Ile Ala Gly Gly Ile Ala Gly Gly Leu Ala Leu Leu Ala Cys Ala
        515                 520                 525

Gly Leu Ala Tyr Lys Phe Val Val Pro Gly Ala Ala Thr Pro Tyr Ala
    530                 535                 540

Gly Glu Pro Ala Pro Phe Asp Glu Thr Leu Gly Glu Glu Asp Lys Asp
545                 550                 555                 560

Leu Asp Glu Pro Glu Gln Phe Arg Leu Pro Glu Glu Asn Glu Trp Asn
                565                 570                 575

Tyr Pro Tyr Asp Val Pro Asp Tyr Ala
            580                 585


<210> SEQ ID NO 31
<211> LENGTH: 627
<212> TYPE: DNA
<213> ORGANISM: Artificial Sequence
<220> FEATURE:
<223> OTHER INFORMATION: Immunogen consensus nucleic acid sequence 16

<400> SEQUENCE: 31

atggactgga cctggattct gttcctggtg gccgctgcca caagagtgca cagcaacgcc     60

ctgcggagac tgcccgtgat ctgcagcttc ctggtgtttc tggtgttcag caacgtgctg    120

tgcttccggg gcaacaacgg ccacaacagc agcagcagcc tgtacaacgg cagccagttc    180

atcgagcagc tgaacaacag cttcaccagc gcctttctgg aaagccagag catgaacaag    240

atcggcgacg acctggccga gacaatcagc aacgagctgg tgtccgtgct gcagaagaac    300

agccccacct tcctggaaag cagcttcgac atcaagagcg aagtgaagaa acacgccaag    360

agcatgctga aagaactgat caaagtgggc ctgcccagct tcgagaatct ggtcgccgag    420

aacgtgaagc cccccaaggt ggaccctgcc acatacggca tcatcgtgcc cgtgctgacc    480

agcctgttca acaaggtgga gacagccgtg ggcgccaagg tgtccgacga gatctggaac    540

tacaacagcc ccgacgtgtc cgagagcgag gaaagcctga gcgacgactt cttcgactac    600

ccctacgacg tgcccgacta cgcctga                                        627


<210> SEQ ID NO 32
<211> LENGTH: 208
<212> TYPE: PRT
```

<213> ORGANISM: Artificial Sequence
<220> FEATURE:
<223> OTHER INFORMATION: Immunogen consensus amino acid sequence 16

<400> SEQUENCE: 32

```
Met Asp Trp Thr Trp Ile Leu Phe Leu Val Ala Ala Ala Thr Arg Val
1               5                   10                  15

His Ser Asn Ala Leu Arg Arg Leu Pro Val Ile Cys Ser Phe Leu Val
            20                  25                  30

Phe Leu Val Phe Ser Asn Val Leu Cys Phe Arg Gly Asn Asn Gly His
        35                  40                  45

Asn Ser Ser Ser Ser Leu Tyr Asn Gly Ser Gln Phe Ile Glu Gln Leu
    50                  55                  60

Asn Asn Ser Phe Thr Ser Ala Phe Leu Glu Ser Gln Ser Met Asn Lys
65                  70                  75                  80

Ile Gly Asp Asp Leu Ala Glu Thr Ile Ser Asn Glu Leu Val Ser Val
                85                  90                  95

Leu Gln Lys Asn Ser Pro Thr Phe Leu Glu Ser Ser Phe Asp Ile Lys
            100                 105                 110

Ser Glu Val Lys Lys His Ala Lys Ser Met Leu Lys Glu Leu Ile Lys
        115                 120                 125

Val Gly Leu Pro Ser Phe Glu Asn Leu Val Ala Glu Asn Val Lys Pro
    130                 135                 140

Pro Lys Val Asp Pro Ala Thr Tyr Gly Ile Ile Val Pro Val Leu Thr
145                 150                 155                 160

Ser Leu Phe Asn Lys Val Glu Thr Ala Val Gly Ala Lys Val Ser Asp
                165                 170                 175

Glu Ile Trp Asn Tyr Asn Ser Pro Asp Val Ser Glu Ser Glu Glu Ser
            180                 185                 190

Leu Ser Asp Asp Phe Phe Asp Tyr Pro Tyr Asp Val Pro Asp Tyr Ala
        195                 200                 205
```

<210> SEQ ID NO 33
<211> LENGTH: 1944
<212> TYPE: DNA
<213> ORGANISM: Artificial Sequence
<220> FEATURE:
<223> OTHER INFORMATION: Immunogen consensus nucleic acid sequence 17

<400> SEQUENCE: 33

```
atggactgga catggattct gttcctggtg gctgctgcta ctagagtgca ttcaagaaaa     60

ctgtattgcg tgctgctgct gagcgccttc gagttcacct atatgatcaa cttcggaagg    120

ggccagaatt actgggagca cccctatcag aactctgacg tgtaccgacc tattaatgaa    180

caccgggagc atcccaagga gtacgaatat cctctgcacc aggaacatac atatcagcag    240

gaggacagcg gggaggatga aaacactctg cagcacgcct acccaatcga ccatgaagga    300

gctgagccag caccccagga gcagaatctg tttagctcca tcgaaattgt ggagcgcagt    360

aactacatgg gcaatccctg gaccgagtac atggccaagt atgatatcga ggaagtccac    420

gggtccggaa ttcgcgtgga cctgggcgaa gatgccgagg tcgctgggac acagtatcga    480

ctgccttccg gcaaatgccc agtgttcggc aaggggatca ttatcgagaa ctctaatacc    540

acatttctga cccccgtggc cacagggaac cagtacctga aggacggcgg attcgctttt    600

ccccctactg aacccctgat gtctcctatg accctggacg agatgaggca cttctacaag    660

gataacaaat acgtcaagaa tctggacgag ctgactctgt gctcacgcca tgctggaaac    720
```

-continued

```
atgatcccag acaacgataa gaacagcaac tacaagtatc ccgcagtgta cgacgataag    780
gacaagaaat gtcacatcct gtatattgcc gctcaggaaa acaatggccc ccggtactgc    840
aacaaagatg agtctaagag aaacagtatg ttctgtttca ggcctgcaaa agacatcagt    900
ttccagaact acacatatct gtcaaagaac gtggtcgata attgggagaa agtgtgcccc    960
agaaagaacc tgcagaatgc taagtttggg ctgtgggtcg acggaaactg cgaagatatc   1020
ccacacgtga atgagttccc cgcaattgac ctgtttgaat gtaacaagct ggtgttcgag   1080
ctgtccgcct ctgatcagcc taagcagtac gagcagcatc tgacagacta tgaaaagatc   1140
aaagagggct ttaagaacaa aaacgcatca atgatcaaga gcgccttcct gccaactggg   1200
gccttcaagg ccgataggta caaaagccac ggaaagggct acaactgggg aaactataat   1260
acagaaactc agaaatgcga gatcttcaat gtcaagccca cctgtctgat caacaattct   1320
agttacatcg ctactaccgc actgtctcat cctattgagg tggaaaacaa ttttccatgc   1380
agtctgtaca aagacgaaat catgaaggag attgaaaggg agagcaaacg catcaagctg   1440
aacgataatg acgatgaggg gaacaagaaa attatcgccc ctcgaatctt catttccgac   1500
gataaagact ctctgaagtg cccttgtgat ccagagatgg tcagtaattc aacctgtcgc   1560
ttctttgtct gcaagtgcgt ggaacggaga gccgaggtga catccaacaa tgaggtggtc   1620
gtgaaagagg aatacaagga cgaatatgcc gatatcccag agcacaagcc cacttacgac   1680
aagatgaaaa ttatcattgc ttcaagcgca gccgtcgccg tgctggctac cattctgatg   1740
gtgtacctgt ataagagaaa aggaaacgcc gaaaaatacg acaagatgga tgagcctcag   1800
gattatggca aaagcaactc ccggaatgac gaaatgctgg accccgaggc tagcttttgg   1860
ggcgaggaaa agagagcatc ccataccacc cccgtcctga tggaaaagcc ttactattac   1920
ccctacgatg tgcccgatta cgca                                          1944
```

<210> SEQ ID NO 34
<211> LENGTH: 648
<212> TYPE: PRT
<213> ORGANISM: Artificial Sequence
<220> FEATURE:
<223> OTHER INFORMATION: Immunogen consensus amino acid sequence 17

<400> SEQUENCE: 34

```
Met Asp Trp Thr Trp Ile Leu Phe Leu Val Ala Ala Ala Thr Arg Val
1               5                   10                  15

His Ser Arg Lys Leu Tyr Cys Val Leu Leu Leu Ser Ala Phe Glu Phe
            20                  25                  30

Thr Tyr Met Ile Asn Phe Gly Arg Gly Gln Asn Tyr Trp Glu His Pro
        35                  40                  45

Tyr Gln Asn Ser Asp Val Tyr Arg Pro Ile Asn Glu His Arg Glu His
    50                  55                  60

Pro Lys Glu Tyr Glu Tyr Pro Leu His Gln Glu His Thr Tyr Gln Gln
65                  70                  75                  80

Glu Asp Ser Gly Glu Asp Glu Asn Thr Leu Gln His Ala Tyr Pro Ile
                85                  90                  95

Asp His Glu Gly Ala Glu Pro Ala Pro Gln Glu Gln Asn Leu Phe Ser
            100                 105                 110

Ser Ile Glu Ile Val Glu Arg Ser Asn Tyr Met Gly Asn Pro Trp Thr
        115                 120                 125

Glu Tyr Met Ala Lys Tyr Asp Ile Glu Glu Val His Gly Ser Gly Ile
    130                 135                 140
```

-continued

```
Arg Val Asp Leu Gly Glu Asp Ala Glu Val Ala Gly Thr Gln Tyr Arg
145                 150                 155                 160

Leu Pro Ser Gly Lys Cys Pro Val Phe Gly Lys Gly Ile Ile Ile Glu
                165                 170                 175

Asn Ser Asn Thr Thr Phe Leu Thr Pro Val Ala Thr Gly Asn Gln Tyr
            180                 185                 190

Leu Lys Asp Gly Gly Phe Ala Phe Pro Pro Thr Glu Pro Leu Met Ser
        195                 200                 205

Pro Met Thr Leu Asp Glu Met Arg His Phe Tyr Lys Asp Asn Lys Tyr
    210                 215                 220

Val Lys Asn Leu Asp Glu Leu Thr Leu Cys Ser Arg His Ala Gly Asn
225                 230                 235                 240

Met Ile Pro Asp Asn Asp Lys Asn Ser Asn Tyr Lys Tyr Pro Ala Val
                245                 250                 255

Tyr Asp Asp Lys Asp Lys Lys Cys His Ile Leu Tyr Ile Ala Ala Gln
            260                 265                 270

Glu Asn Asn Gly Pro Arg Tyr Cys Asn Lys Asp Glu Ser Lys Arg Asn
        275                 280                 285

Ser Met Phe Cys Phe Arg Pro Ala Lys Asp Ile Ser Phe Gln Asn Tyr
    290                 295                 300

Thr Tyr Leu Ser Lys Asn Val Val Asp Asn Trp Glu Lys Val Cys Pro
305                 310                 315                 320

Arg Lys Asn Leu Gln Asn Ala Lys Phe Gly Leu Trp Val Asp Gly Asn
                325                 330                 335

Cys Glu Asp Ile Pro His Val Asn Glu Phe Pro Ala Ile Asp Leu Phe
            340                 345                 350

Glu Cys Asn Lys Leu Val Phe Glu Leu Ser Ala Ser Asp Gln Pro Lys
        355                 360                 365

Gln Tyr Glu Gln His Leu Thr Asp Tyr Glu Lys Ile Lys Glu Gly Phe
    370                 375                 380

Lys Asn Lys Asn Ala Ser Met Ile Lys Ser Ala Phe Leu Pro Thr Gly
385                 390                 395                 400

Ala Phe Lys Ala Asp Arg Tyr Lys Ser His Gly Lys Gly Tyr Asn Trp
                405                 410                 415

Gly Asn Tyr Asn Thr Glu Thr Gln Lys Cys Glu Ile Phe Asn Val Lys
            420                 425                 430

Pro Thr Cys Leu Ile Asn Asn Ser Ser Tyr Ile Ala Thr Thr Ala Leu
        435                 440                 445

Ser His Pro Ile Glu Val Glu Asn Asn Phe Pro Cys Ser Leu Tyr Lys
    450                 455                 460

Asp Glu Ile Met Lys Glu Ile Glu Arg Glu Ser Lys Arg Ile Lys Leu
465                 470                 475                 480

Asn Asp Asn Asp Asp Glu Gly Asn Lys Lys Ile Ile Ala Pro Arg Ile
                485                 490                 495

Phe Ile Ser Asp Asp Lys Asp Ser Leu Lys Cys Pro Cys Asp Pro Glu
            500                 505                 510

Met Val Ser Asn Ser Thr Cys Arg Phe Phe Val Cys Lys Cys Val Glu
        515                 520                 525

Arg Arg Ala Glu Val Thr Ser Asn Asn Glu Val Val Val Lys Glu Glu
    530                 535                 540

Tyr Lys Asp Glu Tyr Ala Asp Ile Pro Glu His Lys Pro Thr Tyr Asp
545                 550                 555                 560

Lys Met Lys Ile Ile Ile Ala Ser Ser Ala Ala Val Ala Val Leu Ala
```

```
            565                 570                 575

Thr Ile Leu Met Val Tyr Leu Tyr Lys Arg Lys Gly Asn Ala Glu Lys
        580                 585                 590

Tyr Asp Lys Met Asp Glu Pro Gln Asp Tyr Gly Lys Ser Asn Ser Arg
    595                 600                 605

Asn Asp Glu Met Leu Asp Pro Glu Ala Ser Phe Trp Gly Glu Glu Lys
    610                 615                 620

Arg Ala Ser His Thr Thr Pro Val Leu Met Glu Lys Pro Tyr Tyr Tyr
625                 630                 635                 640

Pro Tyr Asp Val Pro Asp Tyr Ala
            645
```

<210> SEQ ID NO 35
<211> LENGTH: 1161
<212> TYPE: DNA
<213> ORGANISM: Artificial Sequence
<220> FEATURE:
<223> OTHER INFORMATION: Immunogen consensus nucleic acid sequence 18

<400> SEQUENCE: 35

```
atggactgga cctggattct gttcctggtg gccgctgcca cacgggtgca cagcatgcgg     60

aagctggcta tcctgagcgt gtccagcttc ctgttcgtgg aggccctgtt ccaagagtac    120

cagtgctacg gcagcagcag caacacaaga gtgctgaacg agctgaacta cgacaacgcc    180

ggcaccaacc tgtacaacga gctggaaatg aactactacg gcaagcagga aaactggtac    240

agcctgaaga agaacagccg gtccctgggc gagaacgacg acggcaacaa caacaacggc    300

gacaacggca gagagggcaa ggacgaggac aagcgggatg gcaacaacga ggacaacgag    360

aagctgcgga agcccaagca caagaagctg aagcagcccg gcgacggcaa ccccgacccc    420

aacgccaacc ccaacgtgga ccccaatgcc aatcctaatg tcgatcccaa cgctaaccca    480

aatgtcgacc ctaacgcaaa tcctaacgcc aatcccaatg caaaccctaa tgccaaccca    540

aatgctaatc caaacgcaaa ccccaatgct aaccccaacg ctaaccctaa tgcaaatcca    600

aatgccaacc ccaacgccaa cccaaacgcc aatcccaacg ctaatcctaa cgctaacccc    660

aacgccaatc ctaacgccaa cccaaacgct aacccaaatg ccaaccccaa tgcaaatcct    720

aatgctaatc ctaacgctaa tccaaatgca aatccaaaca agaacaacca gggcaacggc    780

cagggccaca acatgcccaa cgaccccaac cggaacgtgg acgagaatgc caatgccaac    840

aacgccgtga agaacaacaa caatgaggaa cccagcgaca agcacatcga gcagtacctc    900

aagaagatcc agaacagcct gagcaccgag tggagcccct gtagcgtgac ctgcggcaac    960

ggcatccaag tccggatcaa gcccggcagc gccaacaagc ccaaggacga gctggattac   1020

gagaacgaca tcgagaagaa aatctgcaag atggaaaagt gcagcagcgt gttcaacgtg   1080

gtcaacagca gcatcggcct gatcatggtg ctgagctttc tgttcctcaa ctacccctac   1140

gacgtgcccg actacgcctg a                                             1161
```

<210> SEQ ID NO 36
<211> LENGTH: 386
<212> TYPE: PRT
<213> ORGANISM: Artificial Sequence
<220> FEATURE:
<223> OTHER INFORMATION: Immunogen consensus amino acid sequence 18

<400> SEQUENCE: 36

```
Met Asp Trp Thr Trp Ile Leu Phe Leu Val Ala Ala Ala Thr Arg Val
1               5                   10                  15
```

-continued

```
His Ser Met Arg Lys Leu Ala Ile Leu Ser Val Ser Ser Phe Leu Phe
            20                  25                  30

Val Glu Ala Leu Phe Gln Glu Tyr Gln Cys Tyr Gly Ser Ser Ser Asn
        35                  40                  45

Thr Arg Val Leu Asn Glu Leu Asn Tyr Asp Asn Ala Gly Thr Asn Leu
    50                  55                  60

Tyr Asn Glu Leu Glu Met Asn Tyr Tyr Gly Lys Gln Glu Asn Trp Tyr
65                  70                  75                  80

Ser Leu Lys Lys Asn Ser Arg Ser Leu Gly Glu Asn Asp Asp Gly Asn
                85                  90                  95

Asn Asn Asn Gly Asp Asn Gly Arg Glu Gly Lys Asp Glu Asp Lys Arg
            100                 105                 110

Asp Gly Asn Asn Glu Asp Asn Glu Lys Leu Arg Lys Pro Lys His Lys
        115                 120                 125

Lys Leu Lys Gln Pro Gly Asp Gly Asn Pro Asp Pro Asn Ala Asn Pro
    130                 135                 140

Asn Val Asp Pro Asn Ala Asn Pro Asn Val Asp Pro Asn Ala Asn Pro
145                 150                 155                 160

Asn Val Asp Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Ala Asn Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Lys Asn Asn
                245                 250                 255

Gln Gly Asn Gly Gln Gly His Asn Met Pro Asn Asp Pro Asn Arg Asn
            260                 265                 270

Val Asp Glu Asn Ala Asn Ala Asn Asn Ala Val Lys Asn Asn Asn Asn
        275                 280                 285

Glu Glu Pro Ser Asp Lys His Ile Glu Gln Tyr Leu Lys Lys Ile Gln
    290                 295                 300

Asn Ser Leu Ser Thr Glu Trp Ser Pro Cys Ser Val Thr Cys Gly Asn
305                 310                 315                 320

Gly Ile Gln Val Arg Ile Lys Pro Gly Ser Ala Asn Lys Pro Lys Asp
                325                 330                 335

Glu Leu Asp Tyr Glu Asn Asp Ile Glu Lys Lys Ile Cys Lys Met Glu
            340                 345                 350

Lys Cys Ser Ser Val Phe Asn Val Val Asn Ser Ser Ile Gly Leu Ile
        355                 360                 365

Met Val Leu Ser Phe Leu Phe Leu Asn Tyr Pro Tyr Asp Val Pro Asp
    370                 375                 380

Tyr Ala
385
```

<210> SEQ ID NO 37
<211> LENGTH: 3584
<212> TYPE: DNA
<213> ORGANISM: Artificial Sequence
<220> FEATURE:

<223> OTHER INFORMATION: plasmid 1

<400> SEQUENCE: 37
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720
accgagctcg gatccgccac catggactgg acctggattc tgttcctggt ggccgctgcc 780
acaagagtgc acagcaacgc cctgcggaga ctgcccgtga tctgcagctt cctggtgttt 840
ctggtgttca gcaacgtgct gtgcttccgg ggcaacaacg gccacaacag cagcagcagc 900
ctgtacaacg gcagccagtt catcgagcag ctgaacaaca gcttcaccag cgcctttctg 960
gaaagccaga gcatgaacaa gatcggcgac gacctggccg agacaatcag caacgagctg 1020
gtgtccgtgc tgcagaagaa cagccccacc ttcctggaaa gcagcttcga catcaagagc 1080
gaagtgaaga aacacgccaa gagcatgctg aaagaactga tcaaagtggg cctgcccagc 1140
ttcgagaatc tggtcgccga gaacgtgaag ccccccaagg tggaccctgc cacatacggc 1200
atcatcgtgc ccgtgctgac cagcctgttc aacaaggtgg agacagccgt gggcgccaag 1260
gtgtccgacg agatctggaa ctacaacagc cccgacgtgt ccgagagcga ggaaagcctg 1320
agcgacgact tcttcgacta cccctacgac gtgcccgact acgcctgatg actcgagtct 1380
agagggcccg tttaaacccg ctgatcagcc tcgactgtgc cttctagttg ccagccatct 1440
gttgtttgcc cctcccccgt gccttccttg accctggaag gtgccactcc cactgtcctt 1500
tcctaataaa atgaggaaat tgcatcgcat tgtctgagta ggtgtcattc tattctgggg 1560
ggtggggtgg ggcaggacag caagggggag gattgggaag acaatagcag gcatgctggg 1620
gatgcggtgg gctctatggc ttctactggg cggttttatg gacagcaagc gaaccggaat 1680
tgccagctgg ggcgccctct ggtaaggttg ggaagccctg caaagtaaac tggatggctt 1740
tcttgccgcc aaggatctga tggcgcaggg gatcaagctc tgatcaagag acaggatgag 1800
gatcgtttcg catgattgaa caagatggat tgcacgcagg ttctccggcc gcttgggtgg 1860
agaggctatt cggctatgac tgggcacaac agacaatcgg ctgctctgat gccgccgtgt 1920
tccggctgtc agcgcagggg cgcccggttc tttttgtcaa gaccgacctg tccggtgccc 1980
tgaatgaact gcaagacgag gcagcgcggc tatcgtggct ggccacgacg ggcgttcctt 2040
gcgcagctgt gctcgacgtt gtcactgaag cgggaaggga ctggctgcta ttgggcgaag 2100
tgccggggca ggatctcctg tcatctcacc ttgctcctgc cgagaaagta tccatcatgg 2160
ctgatgcaat gcggcggctg catacgcttg atccggctac ctgcccattc gaccaccaag 2220
cgaaacatcg catcgagcga gcacgtactc ggatggaagc cggtcttgtc gatcaggatg 2280
atctggacga agagcatcag gggctcgcgc cagccgaact gttcgccagg ctcaaggcga 2340
gcatgcccga cggcgaggat ctcgtcgtga cccatggcga tgcctgcttg ccgaatatca 2400
tggtggaaaa tggccgcttt tctggattca tcgactgtgg ccggctgggt gtggcggacc 2460
gctatcagga catagcgttg gctacccgtg atattgctga agagcttggc ggcgaatggg 2520
ctgaccgctt cctcgtgctt tacggtatcg ccgctcccga ttcgcagcgc atcgccttct 2580
atcgccttct tgacgagttc ttctgaatta ttaacgctta caatttcctg atgcggtatt 2640
ttctccttac gcatctgtgc ggtatttcac accgcatcag gtggcacttt tcggggaaat 2700
gtgcgcggaa cccctatttg tttatttttc taaatacatt caaatatgta tccgctcatg 2760
agacaataac cctgataaat gcttcaataa tagcacgtgc taaaacttca tttttaattt 2820
aaaaggatct aggtgaagat cctttttgat aatctcatga ccaaaatccc ttaacgtgag 2880
ttttcgttcc actgagcgtc agaccccgta gaaaagatca aaggatcttc ttgagatcct 2940 tttttctgc gcgtaatctg ctgcttgcaa acaaaaaaac caccgctacc agcggtggtt 3000
tgtttgccgg atcaagagct accaactctt tttccgaagg taactggctt cagcagagcg 3060
cagataccaa atactgttct tctagtgtag ccgtagttag gccaccactt caagaactct 3120
gtagcaccgc ctacatacct cgctctgcta atcctgttac cagtggctgc tgccagtggc 3180
gataagtcgt gtcttaccgg gttggactca agacgatagt taccggataa ggcgcagcgg 3240
tcgggctgaa cggggggttc gtgcacacag cccagcttgg agcgaacgac ctacaccgaa 3300
ctgagatacc tacagcgtga gctatgagaa agcgccacgc ttcccgaagg gagaaaggcg 3360
gacaggtatc cggtaagcgg cagggtcgga acaggagagc gcacgaggga gcttccaggg 3420
ggaaacgcct ggtatcttta tagtcctgtc gggtttcgcc acctctgact tgagcgtcga 3480
tttttgtgat gctcgtcagg ggggcggagc ctatggaaaa acgccagcaa cgcggccttt 3540
ttacggttcc tggccttttg ctggcctttt gctcacatgt tctt 3584

<210> SEQ ID NO 38
<211> LENGTH: 4274
<212> TYPE: DNA
<213> ORGANISM: Artificial Sequence
<220> FEATURE:
<223> OTHER INFORMATION: plasmid 2

<400> SEQUENCE: 38
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720

-continued

```
accgagctcg gatccgccac catggactgg acctggattc tgttcctggt ggccgctgcc    780
acacgggtgc acagcatgcg gaagctggct atcctgagcg tgtccagctt cctgttcgtg    840
gaggccctgt tccaagagta ccagtgctac ggcagcagca gcaacacaag agtgctgaac    900
gagctgaact acgacaacgc cggcaccaac ctgtacaacg agctggaaat gaactactac    960
ggcaagcagg aaaactggta cagcctgaag aagaacagcc ggtccctggg cgagaacgac   1020
gacggcaaca acaacaacgg cgacaacggc agagagggca aggacgagga caagcgggat   1080
ggcaacaacg aggacaacga gaagctgcgg aagcccaagc acaagaagct gaagcagccc   1140
ggcgacggca accccgaccc caacgccaac cccaacgtgg accccaatgc caatcctaat   1200
gtcgatccca acgctaaccc aaatgtcgac cctaacgcaa atcctaacgc caatcccaat   1260
gcaaacccta atgccaaccc aaatgctaat ccaaacgcaa accccaatgc taaccccaac   1320
gctaacccta atgcaaatcc aaatgccaac cccaacgcca acccaaacgc caatcccaac   1380
gctaatccta acgctaaccc caacgccaat cctaacgcca acccaaacgc taacccaaat   1440
gccaacccca atgcaaatcc taatgctaat cctaacgcta atccaaatgc aaatccaaac   1500
gctaatccta atgccaaccc taacgcaaac cccaacgcaa atccaaatgc taacccaaat   1560
gcaaatccca acgccaatcc aaacgcaaat ccaaatgcca atcctaatgc aaaccctaat   1620
gcaaatccca atgctaatcc taatgctaat ccaaacaaga acaaccaggg caacggccag   1680
ggccacaaca tgcccaacga ccccaaccgg aacgtggacg agaatgccaa tgccaacaac   1740
gccgtgaaga acaacaacaa tgaggaaccc agcgacaagc acatcgagca gtacctcaag   1800
aagatccaga acagcctgag caccgagtgg agcccctgta gcgtgacctg cggcaacggc   1860
atccaagtcc ggatcaagcc cggcagcgcc aacaagccca aggacgagct ggattacgag   1920
aacgacatcg agaagaaaat ctgcaagatg gaaaagtgca gcagcgtgtt caacgtggtc   1980
aacagcagca tcggcctgat catggtgctg agctttctgt tcctcaacta cccctacgac   2040
gtgcccgact acgcctgatg actcgagtct agagggcccg tttaaacccg ctgatcagcc   2100
tcgactgtgc cttctagttg ccagccatct gttgtttgcc cctcccccgt gccttccttg   2160
accctggaag gtgccactcc cactgtcctt tcctaataaa atgaggaaat tgcatcgcat   2220
tgtctgagta ggtgtcattc tattctgggg ggtggggtgg ggcaggacag caagggggag   2280
gattgggaag acaatagcag gcatgctggg gatgcggtgg gctctatggc ttctactggg   2340
cggttttatg gacagcaagc gaaccggaat tgccagctgg ggcgccctct ggtaaggttg   2400
ggaagccctg caaagtaaac tggatggctt tcttgccgcc aaggatctga tggcgcaggg   2460
gatcaagctc tgatcaagag acaggatgag gatcgtttcg catgattgaa caagatggat   2520
tgcacgcagg ttctccggcc gcttgggtgg agaggctatt cggctatgac tgggcacaac   2580
agacaatcgg ctgctctgat gccgccgtgt tccggctgtc agcgcagggg cgcccggttc   2640
tttttgtcaa gaccgacctg tccggtgccc tgaatgaact gcaagacgag gcagcgcggc   2700
tatcgtggct ggccacgacg ggcgttcctt gcgcagctgt gctcgacgtt gtcactgaag   2760
cgggaaggga ctggctgcta ttgggcgaag tgccggggca ggatctcctg tcatctcacc   2820
ttgctcctgc cgagaaagta tccatcatgg ctgatgcaat gcggcggctg catacgcttg   2880
atccggctac ctgcccattc gaccaccaag cgaaacatcg catcgagcga gcacgtactc   2940
ggatggaagc cggtcttgtc gatcaggatg atctggacga agagcatcag gggctcgcgc   3000
cagccgaact gttcgccagg ctcaaggcga gcatgcccga cggcgaggat ctcgtcgtga   3060
cccatggcga tgcctgcttg ccgaatatca tggtggaaaa tggccgcttt tctggattca   3120
```

-continued tcgactgtgg ccggctgggt gtggcggacc gctatcagga catagcgttg gctacccgtg 3180
atattgctga agagcttggc ggcgaatggg ctgaccgctt cctcgtgctt tacggtatcg 3240
ccgctcccga ttcgcagcgc atcgccttct atcgccttct tgacgagttc ttctgaatta 3300
ttaacgctta caatttcctg atgcggtatt ttctccttac gcatctgtgc ggtatttcac 3360
accgcatcag gtggcacttt tcggggaaat gtgcgcggaa cccctatttg tttatttttc 3420
taaatacatt caaatatgta tccgctcatg agacaataac cctgataaat gcttcaataa 3480
tagcacgtgc taaaacttca tttttaattt aaaaggatct aggtgaagat cctttttgat 3540
aatctcatga ccaaaatccc ttaacgtgag ttttcgttcc actgagcgtc agaccccgta 3600
gaaaagatca aaggatcttc ttgagatcct ttttttctgc gcgtaatctg ctgcttgcaa 3660
acaaaaaaac caccgctacc agcggtggtt tgtttgccgg atcaagagct accaactctt 3720
tttccgaagg taactggctt cagcagagcg cagataccaa atactgttct tctagtgtag 3780
ccgtagttag gccaccactt caagaactct gtagcaccgc ctacatacct cgctctgcta 3840
atcctgttac cagtggctgc tgccagtggc gataagtcgt gtcttaccgg gttggactca 3900
agacgatagt taccggataa ggcgcagcgg tcgggctgaa cggggggttc gtgcacacag 3960
cccagcttgg agcgaacgac ctacaccgaa ctgagatacc tacagcgtga gctatgagaa 4020
agcgccacgc ttcccgaagg gagaaaggcg gacaggtatc cggtaagcgg cagggtcgga 4080
acaggagagc gcacgaggga gcttccaggg ggaaacgcct ggtatcttta tagtcctgtc 4140
gggtttcgcc acctctgact tgagcgtcga tttttgtgat gctcgtcagg ggggcggagc 4200
ctatggaaaa acgccagcaa cgcggccttt ttacggttcc tggccttttg ctggcctttt 4260
gctcacatgt tctt 4274

<210> SEQ ID NO 39
<211> LENGTH: 4736
<212> TYPE: DNA
<213> ORGANISM: Artificial Sequence
<220> FEATURE:
<223> OTHER INFORMATION: plasmid 3

<400> SEQUENCE: 39
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540
aaaatgtcgt aacaactccg ccccattgac gcaaatgggc ggtaggcgtg tacggtggga 600
ggtctatata agcagagctc tctggctaac tagagaaccc actgcttact ggcttatcga 660
aattaatacg actcactata gggagaccca agctggctag cgtttaaact taagcttggt 720
accgagctcg gatccgccac catggactgg acctggattc tgttcctcgt cgcagctgcc 780
accagagtgc acagcaagca catcctgtac atcagcttct acttcatcct ggtgaacctg 840

-continued

```
ctgatcttcc acatcaacgg caagatcatc aagaacagcg agaaggacga gatcatcaaa    900
agcaacctgc ggagcggcag cagcaacagc cggaaccgga tcaacgagga aaagcacgag    960
aagaaacacg tgctgagcca caacagctac gaaaagacca agaacaatga gaacaacaag   1020
ttcttcgaca aggacaaaga actgaccatg agcaacgtga agaacgtgtc ccagaccaac   1080
ttcaagagcc tgctgcggaa cctgggcgtg agcgagaaca tcttcctgaa agagaacaag   1140
ctgaacaaag agggcaagct gatcgagcac atcatcaacg acgacgacga taagaagaag   1200
tacatcaagg gccaggacga gaaccggcag gaagatctgg aagagaaggc cgccaaagag   1260
acactgcagg gccagcagag cgacctggaa caggaacggc tggccaaaga aaagctgcag   1320
gaacagcagt ccgacagcga gcaggaaaga ctggctaaag agaaactcca agagcagcag   1380
tctgacttgg agcaggaacg cctcgcaaaa gagaagttgc aagagcaaca gtccgatctg   1440
gaacaagagc gcctcgctaa agaaaaactt caggaacaac agagcgattt ggagcaagag   1500
cggagagcca aagagaaatt gcaggaacaa caatctgacc tcgaacagga aagaagggcc   1560
aaagagaagc ttcaagaaca acaaagtgac cttgagcaag agaggcgggc taaagaaaaa   1620
ttgcaagaac agcagcggga tctcgaacag cggaaggccg acaccaagaa gaacctggaa   1680
cggaagaaag aacacggcga cgtgctggcc gaggacctgt acggcagact ggaaatcccc   1740
gccatcgagc tgcccagcga gaacgagcgg ggctactaca tcccccacca gagcagcctg   1800
ccccaggaca accggggcaa cagcagagac agcaaagaga tcagcatcat cgagaaaaca   1860
aaccgggaga gcatcaccac caacgtggag ggcagacggg acatccacaa gggccacctg   1920
gaagaaaaga aggacggcag catcaagccc gagcagaaag aggacaagag cgccgacatc   1980
cagaaccaca ccctggaaac cgtgaacatc agcgacgtga acgacttcca gatcagcaag   2040
tacgaggatg agatcagcgc cgagtacgac gacagcctga tcgacgagga agaggacgac   2100
gaggacctgg acgagttcaa gcccatcgtg cagtacgaca acttccagga cgaggaaaac   2160
atcggcatct acaaagagct ggaagatctg atcgagaaga acgagaacct ggatgatctg   2220
gacgagggca tcgagaagtc cagcgaggaa ctgagcgagg aaaagatcaa gaagggcaag   2280
aagtacgaga aaactaagga caacaacttc aagcccaacg acaagagcct gtacgatgag   2340
cacatcaaga agtacaaaaa cgacaaacag gtgaacaaag aaaaagagaa gttcatcaag   2400
tccctgttcc acatcttcga cggcgacaac gagatcctgc agatcgtgga tgagctgtcc   2460
gaggacatca ccaagtactt catgaagctg tacccctacg acgtgcccga ctacgcctga   2520
tgactcgagt ctagagggcc cgtttaaacc cgctgatcag cctcgactgt gccttctagt   2580
tgccagccat ctgttgtttg cccctccccc gtgccttcct tgaccctgga aggtgccact   2640
cccactgtcc tttcctaata aaatgaggaa attgcatcgc attgtctgag taggtgtcat   2700
tctattctgg ggggtggggt ggggcaggac agcaaggggg aggattggga agacaatagc   2760
aggcatgctg gggatgcggt gggctctatg gcttctactg ggcggtttta tggacagcaa   2820
gcgaaccgga attgccagct ggggcgccct ctggtaaggt tgggaagccc tgcaaagtaa   2880
actggatggc tttcttgccg ccaaggatct gatggcgcag gggatcaagc tctgatcaag   2940
agacaggatg aggatcgttt cgcatgattg aacaagatgg attgcacgca ggttctccgg   3000
ccgcttgggt ggagaggcta ttcggctatg actgggcaca acagacaatc ggctgctctg   3060
atgccgccgt gttccggctg tcagcgcagg ggcgcccggt tctttttgtc aagaccgacc   3120
tgtccggtgc cctgaatgaa ctgcaagacg aggcagcgcg gctatcgtgg ctggccacga   3180
cgggcgttcc ttgcgcagct gtgctcgacg ttgtcactga agcgggaagg gactggctgc   3240
```

tattgggcga agtgccgggg caggatctcc tgtcatctca ccttgctcct gccgagaaag 3300
tatccatcat ggctgatgca atgcggcggc tgcatacgct tgatccggct acctgcccat 3360
tcgaccacca agcgaaacat cgcatcgagc gagcacgtac tcggatggaa gccggtcttg 3420
tcgatcagga tgatctggac gaagagcatc aggggctcgc gccagccgaa ctgttcgcca 3480
ggctcaaggc gagcatgccc gacggcgagg atctcgtcgt gacccatggc gatgcctgct 3540
tgccgaatat catggtggaa aatggccgct tttctggatt catcgactgt ggccggctgg 3600
gtgtggcgga ccgctatcag gacatagcgt tggctacccg tgatattgct gaagagcttg 3660
gcggcgaatg ggctgaccgc ttcctcgtgc tttacggtat cgccgctccc gattcgcagc 3720
gcatcgcctt ctatcgcctt cttgacgagt tcttctgaat tattaacgct tacaatttcc 3780
tgatgcggta ttttctcctt acgcatctgt gcggtatttc acaccgcatc aggtggcact 3840
tttcggggaa atgtgcgcgg aacccctatt tgtttatttt tctaaataca ttcaaatatg 3900
tatccgctca tgagacaata accctgataa atgcttcaat aatagcacgt gctaaaactt 3960
catttttaat ttaaaaggat ctaggtgaag atcctttttg ataatctcat gaccaaaatc 4020
ccttaacgtg agttttcgtt ccactgagcg tcagaccccg tagaaaagat caaaggatct 4080
tcttgagatc ctttttttct gcgcgtaatc tgctgcttgc aaacaaaaaa accaccgcta 4140
ccagcggtgg tttgtttgcc ggatcaagag ctaccaactc tttttccgaa ggtaactggc 4200
ttcagcagag cgcagatacc aaatactgtt cttctagtgt agccgtagtt aggccaccac 4260
ttcaagaact ctgtagcacc gcctacatac ctcgctctgc taatcctgtt accagtggct 4320
gctgccagtg gcgataagtc gtgtcttacc gggttggact caagacgata gttaccggat 4380
aaggcgcagc ggtcgggctg aacggggggt tcgtgcacac agcccagctt ggagcgaacg 4440
acctacaccg aactgagata cctacagcgt gagctatgag aaagcgccac gcttcccgaa 4500
gggagaaagg cggacaggta tccggtaagc ggcagggtcg gaacaggaga gcgcacgagg 4560
gagcttccag ggggaaacgc ctggtatctt tatagtcctg tcgggtttcg ccacctctga 4620
cttgagcgtc gatttttgtg atgctcgtca ggggggcgga gcctatggaa aaacgccagc 4680
aacgcggcct ttttacggtt cctggccttt tgctggcctt ttgctcacat gttctt 4736

<210> SEQ ID NO 40
<211> LENGTH: 4715
<212> TYPE: DNA
<213> ORGANISM: Artificial Sequence
<220> FEATURE:
<223> OTHER INFORMATION: plasmid 4

<400> SEQUENCE: 40
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240
gtatttacgg taaactgccc acttggcagt acatcaagtg tatcatatgc caagtacgcc 300
ccctattgac gtcaatgacg gtaaatggcc cgcctggcat tatgcccagt acatgacctt 360
atgggacttt cctacttggc agtacatcta cgtattagtc atcgctatta ccatggtgat 420
gcggttttgg cagtacatca atgggcgtgg atagcggttt gactcacggg gatttccaag 480
tctccacccc attgacgtca atgggagttt gttttggcac caaaatcaac gggactttcc 540

-continued

```
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggattc tgttcctggt ggccgctgct    780
acaagagtgc acagcaacca cctgggcaac gtgaagtacc tggtgatcgt gttcctgatc    840
ttcttcgacc tgtttctggt gaacggccgg gacgtgcaga acaacatcgt ggacgagatc    900
aagtaccggg aggaagtgtg caacgacgag gtggacctgt acctgctgat ggactgcagc    960
ggcagcatca gacggcacaa ctgggtgaac cacgccgtgc ccctggccat gaagctgatc   1020
cagcagctga acctgaacga gaacgccatc cacctgtacg tgaacgactt cagcaacaac   1080
gccaaagaga tcatccggct gcacagcgac gccagcaaga acaaagagaa ggccctgatc   1140
atcatcaaga gcctgctgag caccaacctg ccctacggcc ggaccaacct gtctgacgct   1200
ctgctgcagg tgcggaagca cctgaacgac cggatcaacc gggagaacgc caaccagctg   1260
gtggtgatcc tgaccgacgg catccccgac agcatccagg acagcctgaa agagagccgg   1320
aagctgaacg acagaggcgt gaagatcgcc gtgttcggca tcggccaggg catcaacgtg   1380
gccttcaaca gattcctggt gggctgtcac ccccagcgacg gcaagtgcaa cctgtacgcc   1440
gacagcgcct gggagaacgt gaagaatgtg atcggcccct tcatgaaggc cgtgtgcgtg   1500
gaggtggaga aaaccgccag ctgcggcgtg tgggatgagt ggagcccctg cagcgtgacc   1560
tgtggcaagg gcaccagaag ccggaagcgg gagatcctgc acgagggctg caccagcgag   1620
ctgcaggaac agtgcgaaga ggaacggtgc ccccccaaga gggaacccct ggacgtgccc   1680
cacgagcccg aggacgacca gcccagaccc agaggcgaca acttcgccgt ggagaagccc   1740
gaggaaaaca tcatcgacaa caacccccag gaacccagcc ccaaccctga ggaaggcaag   1800
ggcgagaacc ccaacggctt cgacctggac gagaaccccg agaatccccc caaccccgac   1860
atccccgagc aggaacccaa catccctgag gacagcgaga aagaggtgcc cagcgacgtc   1920
cccaagaatc ccgaggatga ccgggaagag aacttcgaca tccccaagaa gcctgagaac   1980
aagcacgaca accagaacaa cctgcccaac gacaagagcg accggtacat cccctacagc   2040
cccctgcccc ccaaggtgct ggacaacgag cggaagcaga gcgaccccca gagccaggac   2100
aacaacggca accggcacgt gcccaacagc gaggaccggg agacaagacc ccacggccgg   2160
aacaacgaga accggtccta caaccggaag tacaacgaca cccccaagca ccccgagcgg   2220
gaggaacacg agaaacccga caacaacaag aagaagggcg gcagcgacaa caagtacaag   2280
attgccggcg gaatcgctgg cggactggcc ctgctggctt gtgccggcct ggcctacaag   2340
tttgtggtgc ctggcgccgc tacaccttat gccggcgagc ctgccccctt tgacgagaca   2400
ctgggcgaag aggacaagga cctggatgag cccgagcagt tccggctgcc cgaagagaac   2460
gagtggaact accccctacga cgtgcccgac tacgcctgat gactcgagtc tagagggccc   2520
gtttaaaccc gctgatcagc ctcgactgtg ccttctagtt gccagccatc tgttgtttgc   2580
ccctcccccg tgccttcctt gaccctggaa ggtgccactc ccactgtcct ttcctaataa   2640
aatgaggaaa ttgcatcgca ttgtctgagt aggtgtcatt ctattctggg gggtggggtg   2700
gggcaggaca gcaaggggga ggattgggaa gacaatagca ggcatgctgg ggatgcggtg   2760
ggctctatgg cttctactgg gcggttttat ggacagcaag cgaaccggaa ttgccagctg   2820
ggcgcccctc tggtaaggtt gggaagccct gcaaagtaaa ctggatggct ttcttgccgc   2880
caaggatctg atggcgcagg ggatcaagct ctgatcaaga gacaggatga ggatcgtttc   2940
```

gcatgattga acaagatgga ttgcacgcag gttctccggc cgcttgggtg gagaggctat 3000
tcggctatga ctgggcacaa cagacaatcg gctgctctga tgccgccgtg ttccggctgt 3060
cagcgcaggg gcgcccggtt ctttttgtca agaccgacct gtccggtgcc ctgaatgaac 3120
tgcaagacga ggcagcgcgg ctatcgtggc tggccacgac gggcgttcct tgcgcagctg 3180
tgctcgacgt tgtcactgaa gcgggaaggg actggctgct attgggcgaa gtgccggggc 3240
aggatctcct gtcatctcac cttgctcctg ccgagaaagt atccatcatg gctgatgcaa 3300
tgcggcggct gcatacgctt gatccggcta cctgcccatt cgaccaccaa gcgaaacatc 3360
gcatcgagcg agcacgtact cggatggaag ccggtcttgt cgatcaggat gatctggacg 3420
aagagcatca ggggctcgcg ccagccgaac tgttcgccag gctcaaggcg agcatgcccg 3480
acggcgagga tctcgtcgtg acccatggcg atgcctgctt gccgaatatc atggtggaaa 3540
atggccgctt ttctggattc atcgactgtg gccggctggg tgtggcggac cgctatcagg 3600
acatagcgtt ggctacccgt gatattgctg aagagcttgg cggcgaatgg gctgaccgct 3660
tcctcgtgct ttacggtatc gccgctcccg attcgcagcg catcgccttc tatcgccttc 3720
ttgacgagtt cttctgaatt attaacgctt acaatttcct gatgcggtat tttctcctta 3780
cgcatctgtg cggtatttca caccgcatca ggtggcactt ttcggggaaa tgtgcgcgga 3840
acccctattt gtttattttt ctaaatacat tcaaatatgt atccgctcat gagacaataa 3900
ccctgataaa tgcttcaata atagcacgtg ctaaaacttc atttttaatt taaaaggatc 3960
taggtgaaga tcctttttga taatctcatg accaaaatcc cttaacgtga gttttcgttc 4020
cactgagcgt cagaccccgt agaaaagatc aaaggatctt cttgagatcc tttttttctg 4080
cgcgtaatct gctgcttgca aacaaaaaaa ccaccgctac cagcggtggt ttgtttgccg 4140
gatcaagagc taccaactct ttttccgaag gtaactggct tcagcagagc gcagatacca 4200
aatactgttc ttctagtgta gccgtagtta ggccaccact tcaagaactc tgtagcaccg 4260
cctacatacc tcgctctgct aatcctgtta ccagtggctg ctgccagtgg cgataagtcg 4320
tgtcttaccg ggttggactc aagacgatag ttaccggata aggcgcagcg gtcgggctga 4380
acggggggtt cgtgcacaca gcccagcttg gagcgaacga cctacaccga actgagatac 4440
ctacagcgtg agctatgaga aagcgccacg cttcccgaag ggagaaaggc ggacaggtat 4500
ccggtaagcg gcagggtcgg aacaggagag cgcacgaggg agcttccagg gggaaacgcc 4560
tggtatcttt atagtcctgt cgggtttcgc cacctctgac ttgagcgtcg atttttgtga 4620
tgctcgtcag gggggcggag cctatggaaa aacgccagca acgcggcctt tttacggttc 4680
ctggcctttt gctggccttt tgctcacatg ttctt 4715

<210> SEQ ID NO 41
<211> LENGTH: 4118
<212> TYPE: DNA
<213> ORGANISM: Artificial Sequence
<220> FEATURE:
<223> OTHER INFORMATION: plasmid 5

<400> SEQUENCE: 41
gctgcttcgc gatgtacggg ccagatatac gcgttgacat tgattattga ctagttatta 60
atagtaatca attacggggt cattagttca tagcccatat atggagttcc gcgttacata 120
acttacggta aatggcccgc ctggctgacc gcccaacgac ccccgcccat tgacgtcaat 180
aatgacgtat gttcccatag taacgccaat agggactttc cattgacgtc aatgggtgga 240

-continued

```
gtatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggattc tgttcctggt ggccgctgcc    780
acacgggtgc acagcatgcg gaagctggct atcctgagcg tgtccagctt cctgttcgtg    840
gaggccctgt tccaagagta ccagtgctac ggcagcagca gcaacacaag agtgctgaac    900
gagctgaact acgacaacgc cggcaccaac ctgtacaacg agctggaaat gaactactac    960
ggcaagcagg aaaactggta cagcctgaag aagaacagcc ggtccctggg cgagaacgac   1020
gacggcaaca acaacaacgg cgacaacggc agagagggca aggacgagga caagcgggat   1080
ggcaacaacg aggacaacga gaagctgcgg aagcccaagc acaagaagct gaagcagccc   1140
ggcgacggca accccgaccc caacgccaac cccaacgtgg accccaatgc caatcctaat   1200
gtcgatccca acgctaaccc aaatgtcgac cctaacgcaa atcctaacgc caatcccaat   1260
gcaaacccta atgccaaccc aaatgctaat ccaaacgcaa accccaatgc taaccccaac   1320
gctaacccta atgcaaatcc aaatgccaac cccaacgcca acccaaacgc caatcccaac   1380
gctaatccta acgctaaccc caacgccaat cctaacgcca acccaaacgc taacccaaat   1440
gccaacccca atgcaaatcc taatgctaat cctaacgcta atccaaatgc aaatccaaac   1500
aagaacaacc agggcaacgg ccagggccac aacatgccca acgaccccaa ccggaacgtg   1560
gacgagaatg ccaatgccaa caacgccgtg aagaacaaca acaatgagga acccagcgac   1620
aagcacatcg agcagtacct caagaagatc cagaacagcc tgagcaccga gtggagcccc   1680
tgtagcgtga cctgcggcaa cggcatccaa gtccggatca agcccggcag cgccaacaag   1740
cccaaggacg agctggatta cgagaacgac atcgagaaga aaatctgcaa gatggaaaag   1800
tgcagcagcg tgttcaacgt ggtcaacagc agcatcggcc tgatcatggt gctgagcttt   1860
ctgttcctca actaccccta cgacgtgccc gactacgcct gatgactcga gtctagaggg   1920
cccgtttaaa cccgctgatc agcctcgact gtgccttcta gttgccagcc atctgttgtt   1980
tgcccctccc ccgtgccttc cttgaccctg gaaggtgcca ctcccactgt cctttcctaa   2040
taaaatgagg aaattgcatc gcattgtctg agtaggtgtc attctattct ggggggtggg   2100
gtggggcagg acagcaaggg ggaggattgg gaagacaata gcaggcatgc tggggatgcg   2160
gtgggctcta tggcttctac tgggcggttt tatggacagc aagcgaaccg gaattgccag   2220
ctggggcgcc ctctggtaag gttgggaagc cctgcaaagt aaactggatg gctttcttgc   2280
cgccaaggat ctgatggcgc aggggatcaa gctctgatca agagacagga tgaggatcgt   2340
ttcgcatgat tgaacaagat ggattgcacg caggttctcc ggccgcttgg gtggagaggc   2400
tattcggcta tgactgggca caacagacaa tcggctgctc tgatgccgcc gtgttccggc   2460
tgtcagcgca ggggcgcccg gttctttttg tcaagaccga cctgtccggt gccctgaatg   2520
aactgcaaga cgaggcagcg cggctatcgt ggctggccac gacgggcgtt ccttgcgcag   2580
ctgtgctcga cgttgtcact gaagcgggaa gggactggct gctattgggc gaagtgccgg   2640
```

ggcaggatct cctgtcatct caccttgctc ctgccgagaa agtatccatc atggctgatg 2700
caatgcggcg gctgcatacg cttgatccgg ctacctgccc attcgaccac caagcgaaac 2760
atcgcatcga gcgagcacgt actcggatgg aagccggtct tgtcgatcag gatgatctgg 2820
acgaagagca tcaggggctc gcgccagccg aactgttcgc caggctcaag gcgagcatgc 2880
ccgacggcga ggatctcgtc gtgacccatg gcgatgcctg cttgccgaat atcatggtgg 2940
aaaatggccg cttttctgga ttcatcgact gtggccggct gggtgtggcg gaccgctatc 3000
aggacatagc gttggctacc cgtgatattg ctgaagagct tggcggcgaa tgggctgacc 3060
gcttcctcgt gctttacggt atcgccgctc ccgattcgca gcgcatcgcc ttctatcgcc 3120
ttcttgacga gttcttctga attattaacg cttacaattt cctgatgcgg tattttctcc 3180
ttacgcatct gtgcggtatt tcacaccgca tcaggtggca cttttcgggg aaatgtgcgc 3240
ggaaccccta tttgtttatt tttctaaata cattcaaata tgtatccgct catgagacaa 3300
taaccctgat aaatgcttca ataatagcac gtgctaaaac ttcattttta atttaaaagg 3360
atctaggtga agatcctttt tgataatctc atgaccaaaa tcccttaacg tgagttttcg 3420
ttccactgag cgtcagaccc cgtagaaaag atcaaaggat cttcttgaga tccttttttt 3480
ctgcgcgtaa tctgctgctt gcaaacaaaa aaaccaccgc taccagcggt ggtttgtttg 3540
ccggatcaag agctaccaac tctttttccg aaggtaactg gcttcagcag agcgcagata 3600
ccaaatactg ttcttctagt gtagccgtag ttaggccacc acttcaagaa ctctgtagca 3660
ccgcctacat acctcgctct gctaatcctg ttaccagtgg ctgctgccag tggcgataag 3720
tcgtgtctta ccgggttgga ctcaagacga tagttaccgg ataaggcgca gcggtcgggc 3780
tgaacggggg gttcgtgcac acagcccagc ttggagcgaa cgacctacac cgaactgaga 3840
tacctacagc gtgagctatg agaaagcgcc acgcttcccg aagggagaaa ggcggacagg 3900
tatccggtaa gcggcagggt cggaacagga gagcgcacga gggagcttcc agggggaaac 3960
gcctggtatc tttatagtcc tgtcgggttt cgccacctct gacttgagcg tcgatttttg 4020
tgatgctcgt caggggggcg gagcctatgg aaaaacgcca gcaacgcggc ctttttacgg 4080
ttcctggcct tttgctggcc ttttgctcac atgttctt 4118

<210> SEQ ID NO 42
<211> LENGTH: 18
<212> TYPE: PRT
<213> ORGANISM: Artificial Sequence
<220> FEATURE:
<223> OTHER INFORMATION: Immunogen amino acid sequence #19

<400> SEQUENCE: 42

Met Asp Trp Thr Trp Ile Leu Phe Leu Val Ala Ala Ala Thr Arg Val
1 5 10 15

His Ser